(12) United States Patent  (10) Patent No.: US 7,393,865 B2
Beaton et al.  (45) Date of Patent: Jul. 1, 2008

(54) SLEEP INDUCING COMPOUNDS AND METHODS RELATING THERETO

(75) Inventors: Graham Beaton, Poway, CA (US); Wilna (Willy) J Moree, San Diego, CA (US); Florence Jovic, La Jolla, CA (US); Timothy Coon, Carlsbad, CA (US); Jinghua Yu, San Marcos, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 554 days.

(21) Appl. No.: 11/156,252

(22) Filed: Jun. 17, 2005

(65) Prior Publication Data

US 2006/0014797 A1 Jan. 19, 2006

Related U.S. Application Data

(60) Provisional application No. 60/580,639, filed on Jun. 17, 2004.

(51) Int. Cl.
 A61K 31/44 (2006.01)
 A61K 31/425 (2006.01)
 A61K 31/381 (2006.01)
 C07D 277/20 (2006.01)
 C07D 333/52 (2006.01)
 C07D 409/06 (2006.01)

(52) U.S. Cl. .................. 514/337; 546/268.1; 546/279.1; 546/280.4; 546/281.1; 548/146; 548/202; 549/29; 549/49; 514/336; 514/365; 514/438; 514/4.43

(58) Field of Classification Search .............. 546/268.1, 546/279.7, 280.4, 281.1; 548/146, 202; 549/29, 549/49; 514/336, 337, 365, 438, 443, 444

See application file for complete search history.

(56) References Cited

U.S. PATENT DOCUMENTS

| 2,947,756 A | 8/1960 | Huebner et al. ............. 260/296 |
| 3,105,836 A | 10/1963 | Huebner et al. ............. 260/296 |
| 3,931,229 A | 1/1976 | Zinnes et al. ........ 260/326.12 R |
| 4,654,352 A | 3/1987 | Ray ........................... 514/324 |
| 5,250,565 A | 10/1993 | Brooks et al. ............... 514/443 |

FOREIGN PATENT DOCUMENTS

| DE | 1 100 619 | 3/1961 |
| DE | 1 199 781 | 9/1965 |
| DE | 1 203 277 | 10/1965 |
| EP | 0 527 687 A2 | 2/1993 |
| EP | 0 721 938 A1 | 7/1996 |
| EP | 0 745 583 A1 | 12/1996 |
| EP | 0 926 145 A1 | 6/1999 |
| JP | 61-134371 | 6/1986 |
| WO | WO 99/58495 | 11/1999 |
| WO | WO 99/58496 | 11/1999 |
| WO | WO 00/69432 | 11/2000 |
| WO | WO 01/07436 A2 | 2/2001 |
| WO | WO 01/83472 A1 | 11/2001 |
| WO | WO 2005/097093 A1 | 10/2005 |

OTHER PUBLICATIONS

Chemical Abstracts, Database Accession No. 1972:46081, 1972.
Chemical Abstracts, Database Accession No. 1989:483971, 1989.

*Primary Examiner*—Golam M. M. Shameem
(74) *Attorney, Agent, or Firm*—Seed IP Law Group PLLC

(57) ABSTRACT

Compounds having the following structure (I):

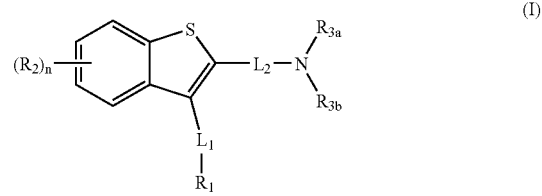

including stereoisomers, prodrugs, and pharmaceutically acceptable salts, esters and solvates thereof, wherein $R_1$, $R_2$, $R_{3a}$, $R_{3b}$, $L_1$, $L_2$ and n are as defined herein. Such compounds generally function as $H_1$ receptor ligands, and thus have utility as sleep inducing agents. Pharmaceutical compositions containing a compound of structure (I), as well as methods relating to the use thereof, are also disclosed.

16 Claims, No Drawings

SLEEP INDUCING COMPOUNDS AND METHODS RELATING THERETO

CROSS-REFERENCE TO RELATED APPLICATION

This application claims the benefit of U.S. Provisional Application No. 60/580,639 filed Jun. 17, 2004, which is hereby incorporated by reference in its entirety.

BACKGROUND OF THE INVENTION

1. Field of the Invention

This invention relates generally to sleep inducing compounds, as well as to methods for induction of sleep by administration of one or more of such compounds to an animal in need thereof.

2. Description of the Related Art

Most people experience, at least transiently and often chronically, problems with sleep. Insomnia occurs at all ages with half of all adults in the United States affected at times (The Gallup Organization, *Sleep in America: A National Survey of U.S. Adults*, The National Sleep Foundation, Washington, D.C., 1995). Insomnia compromises feelings of wellbeing and judgment and performance at tasks requiring alertness (Gillin, *Postgrad Med.* 1992; 92: 157-160). Significantly, inadequate sleep correlates with increased morbidity and mortality (Zammit et al, *Sleep* 1999; 22: S379-85).

In a clinical setting, insomnia may be classified as transient, short-term, or chronic, with durations of a few days, a few weeks, or long-term, respectively (Chessor, *Sleep* 2000; 22: 237-41). Common etiologies for transient insomnia include acute illness, social stress, jet lag, and work shift changes. Short-term insomnias can be caused by grief, stress, and substance exposure. Chronic insomnias can be associated with underlying disease, depression, psychophysiologic conditions, chronic stress, bereavement, substance exposure, and a variety of primary sleep disorders including sleep apnea, periodic limb movement disorder, restless leg syndrome, narcolepsy and hypersomnia. The primary task of the physician is to identify the specific etiology of the insomnia and prescribe a causally specific therapeutic intervention (Pary et al, *Postgrad Med.* 1996; 100: 195-210).

The categories of drugs used as sedative-hypnotics in the United States (Wang et al., *Drug Disposition and Pharmacokinetics* 2003; 37: 10-29) include barbiturates, the benzodiazepine hypnotics, benzodiazepine nonhypnotics, benzodiazepine receptor agonists, antidepressants, antipsychotics, miscellaneous compounds including chloral hydrate, and the antihistamines.

With regard to the antihistamines, histamine enjoys a variety of important chemical messenger roles, having activity toward at least four histamine receptors (i.e., $H_1$-$H_4$) and regulatory function in the nervous, gastrointestinal and immune systems. The antihistamines are reversible competitive ligands of the histamine $H_1$ receptor, and have been categorized over the years as first-, second-, or third-generation classes differentiated by chemical structure and refinement of action. Specifically, first-generation antihistamines such as diphenhydramine, chlorpheniramine, clemastine, hydroxyzine and triprolidine provide $H_1$ receptor blockade, but have significant side effects including sedation, CNS dysfunction due to leakage into the CNS, and anticholinergic adverse effects. In response, the second-generation or so-called "nonsedating" antihistamines, including astemizole, terfenadine, loratadine, cetirizine and fexofenadine, were developed. These compounds have reduced CNS impact and additional antiallergic properties, including inhibition of mast cell degranulation. Desloratadine, a metabolite of loratadine, has been categorized as a third-generation antihistamine (McClellan & Jarvis, *Drugs* 2001; 61: 789-796), and has direct effects on inflammatory mediators such as inhibition of intracellular adhesion molecule-1 (ICAM-1) expression by nasal epithelium. The importance of histamine in sleep regulation is evidenced by the hypnotic effects of certain histamine receptor ligands (Mignot et al., *Nature Neuroscience Supplement;* 5: 1071-1075), particularly the older generation molecules.

While significant advances have been made in the field of sleep initiation and prolongation, there continues to be a need in the art for compounds that are effective as sedative and hypnotic agents, especially for compounds with clinical application to the treatment of insomnia. In particular, there remains a need for compounds having improved selectivity, a quicker onset of action, a shorter half-life and/or the ability to penetrate the CNS. The present invention fulfills these needs and other needs, and provides further related advantages.

BRIEF SUMMARY OF THE INVENTION

In brief, this invention is directed to compounds having the following general structure (I):

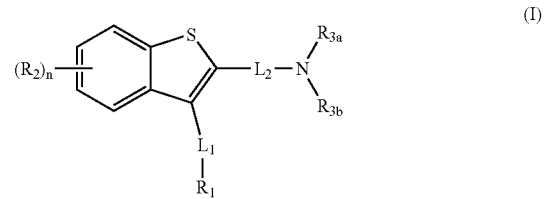

(I)

including stereoisomers, prodrugs and pharmaceutically acceptable salts, esters and solvates thereof, wherein $R_1$, $R_2$, $R_{3a}$, $R_{3b}$, $L_1$, $L_2$ and n are as defined below.

The compounds of this invention may have utility over a wide range of therapeutic applications and may be used to treat a variety of disorders or illnesses. Accordingly, and in another embodiment, methods are disclosed for inhibiting one or more histamine receptors, such as the histamine $H_1$ receptor. In other embodiments, methods are disclosed for treating one or more of a variety of diseases or conditions associated with histamine receptors, including (but not limited to) sleep disorders.

The methods of this invention generally involve administering an effective amount of one or more compounds of this invention, typically in the form of a pharmaceutical composition, to an animal (also referred to here as a "patient", including a human) in need thereof. Accordingly, in still another embodiment, compositions are disclosed containing one or more compounds of this invention in combination with a pharmaceutically acceptable carrier and/or diluent.

These and other aspects of the invention will be apparent upon reference to the following detailed description. To this end, various references are set forth herein which describe in more detail certain procedures, compounds and/or compositions, and are hereby incorporated by reference in their entirety.

DETAILED DESCRIPTION OF THE INVENTION

As noted above, this invention is generally directed to compounds having the following structure (I):

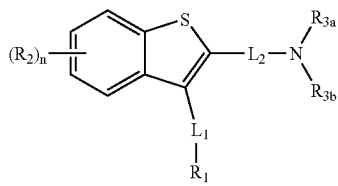

(I)

including stereoisomers, prodrugs and pharmaceutically acceptable salts, esters and solvates thereof, wherein:

$R_1$ is aryl, substituted aryl, heterocycle, substituted heterocycle, alkyl, substituted alkyl, —O-(alkyl) or —O-(substituted alkyl);

$L_1$ and $L_2$ are the same or different and are independently alkanediyl or substituted alkanediyl;

$R_2$ is, at each occurrence, the same or different and independently alkyl, substituted alkyl, alkoxy, substituted alkoxy, cyano, halogen, hydroxyl or —$NR_{4a}R_{4b}$;

n is 0, 1 or 2 and represents the number of $R_2$ groups;

$R_{3a}$ and $R_{3b}$ are the same or different and are independently hydrogen, alkyl or substituted alkyl, or $R_{3a}$ and $R_{3b}$ together with the nitrogen to which they are attached form a heterocycle or a substituted heterocycle; and $R_{4a}$ and $R_{4b}$ are the same or different and are independently hydrogen, alkyl or substituted alkyl.

As used herein, the above terms have the following meaning:

"Alkyl" means a straight chain or branched, noncyclic or cyclic, unsaturated or saturated hydrocarbon containing from 1 to 10 carbon atoms, while the term "lower alkyl" has the same meaning as alkyl but contains from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —$CH_2$-cyclopropyl, —$CH_2$-cyclobutyl, —$CH_2$-cyclopentyl, —$CH_2$-cyclohexyl, and the like; while unsaturated cyclic alkyls include cyclopentenyl and cyclohexenyl, and the like. Cyclic alkyls, also referred to as "homocyclic rings," and include di- and poly-homocyclic rings such as decalin and adamantyl. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like.

"Alkoxy" means an alkyl moiety attached through an oxygen bridge (i.e., —O-alkyl), such as —O-methyl (i.e., methoxy), —O-ethyl (i.e., ethoxy), and the like.

"Thioalkyl" means an alkyl moiety attached through a sulfur bridge (i.e., —S-alkyl) such as —S-methyl, —S-ethyl, and the like.

"Alkanediyl" means a divalent alkyl from which two hydrogen atoms are taken from the same carbon atom or from different carbon atoms. In the case of a saturated alkyl, representative moieties include (but are not limited to) —$CH_2$—, —$CH(CH_3)$—, —$CH_2CH_2$—, —$CH_2CH_2CH_2$—, —CH ($CH_3$)$CH_2$—, -cyclopentane-, -cyclohexane-, -cycloheptane-, and the like. In the case of an unsaturated alkyl, representative moieties include (but are not limited to)

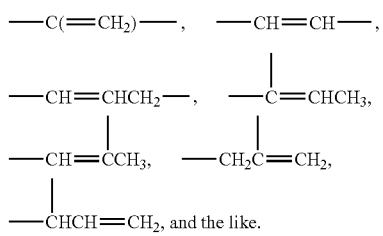

"Aryl" means an aromatic carbocyclic moiety such as phenyl or naphthyl.

"Arylalkyl" means an alkyl having at least one alkyl hydrogen atom replaced with an aryl moiety, such as benzyl (i.e., —$CH_2$-phenyl), —$CH_2$-(1- or 2-naphthyl), —$(CH_2)_2$-phenyl, —$(CH_2)_3$-phenyl, —CH(phenyl)$_2$, and the like.

"Aryloxy" means an aromatic carbocyclic moiety such as phenyl or naphthyl attached through an oxygen bridge (i.e., —O-aryl) such as —O-phenyl, —O-naphthyl, and the like.

"Heteroaryl" means an aromatic heterocycle ring of 5- to 10-members and having at least one heteroatom selected from nitrogen, oxygen and sulfur, and containing at least 1 carbon atom, including both mono- and bicyclic ring systems. Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —$CH_2$-pyridinyl, —$CH_2$-pyrimidinyl, and the like.

"Heterocycle" (also referred to herein as a "heterocycle ring") means a 5- to 7-membered monocyclic, or 7- to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperizinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —$CH_2$-morpholinyl, and the like.

The term "substituted" as used herein means any of the above groups (i.e., alkyl, alkanediyl, aryl, arylalkyl, heteroaryl, heteroarylalkyl, heterocycle or heterocyclealkyl) wherein at least one hydrogen atom is replaced with a substituent. In the case of an oxo substituent (=O") two hydrogen atoms are replaced. "Substituents" within the context of this invention include halogen, hydroxy, oxo, cyano, nitro, amino, alkylamino, dialkylamino, alkyl, alkoxy, thioalkyl, haloalkyl, hydroxyalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, —NR$_a$R$_b$, —NR$_a$C(=O)R$_b$, —NR$_a$C(=O)NR$_a$R$_b$, —NR$_a$C(=O)OR$_b$, —NR$_a$SO$_2$R$_b$, —OR$_a$, —C(=O)R$_a$, —C(=O)OR$_a$, —C(=O)NR$_a$R$_b$, —OC(=O)NR$_a$R$_b$, —SH, —SR$_a$, —SOR$_a$, —S(=O)$_2$R$_a$, —OS(=O)$_2$R$_a$, —S(=O)$_2$OR$_a$, wherein R$_a$ and R$_b$ are the same or different and independently hydrogen, alkyl, haloalkyl, substituted alkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl.

"Halogen" means fluoro, chloro, bromo and iodo.

"Haloalkyl" means an alkyl having at least one hydrogen atom replaced with halogen, such as trifluoromethyl and the like. Haloalkyl is a specific embodiment of substituted alkyl, wherein alkyl is substituted with one or more halogen atoms.

"Hydroxyalkyl" means an alkyl substituted with at least one hydroxyl group.

In one embodiment, R$_1$ is aryl, substituted aryl, heteroaryl or substituted heteroaryl. In this context, representative compounds include (but are not limited to) the following structure (II-1) when R$_1$ is phenyl and L$_1$ is —C(=O)—; structure (II-2) when R$_1$ is 4-fluorophenyl and L$_1$ is ethane-1,1-diyl; structure (III-1) when R$_1$ is 2-pyridyl; and structure (III-2) when R$_1$ is pyrazyl:

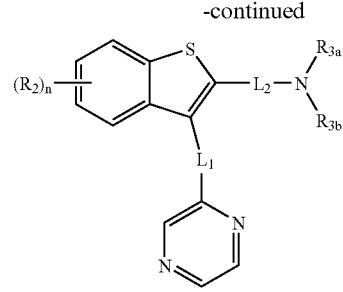
(II-1)

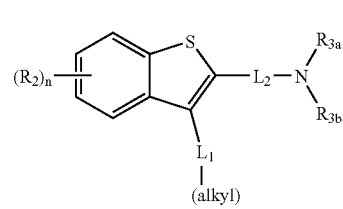
(II-2)

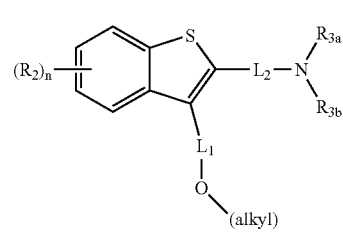
(III-1)

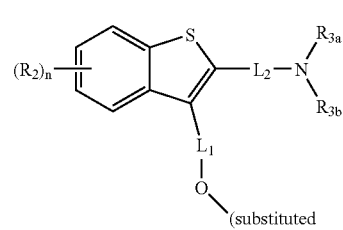
(III-2)

In another embodiment, R$_1$ is alkyl, —O-(alkyl) or —O-(substituted alkyl), as represented by the following structures (IV-1), (IV-2) and (IV-3), respectively:

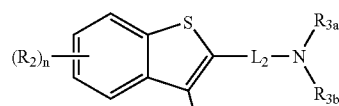
(IV-1)

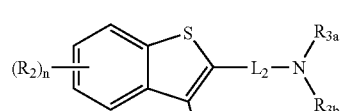
(IV-2)

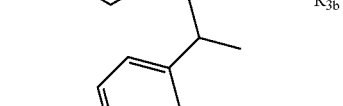
(IV-3)

In another embodiment of the invention, L$_1$ is alkanediyl such as one of the following divalent saturated alkyls: —CH$_2$— as represented by structure (V-1); —CH(CH$_3$)— as represented by structure (V-2); or —C(CH$_3$)$_2$— as represented by structure (V-3).

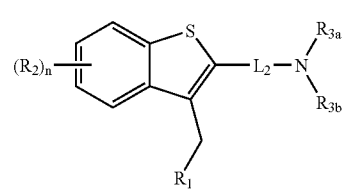
(V-1)

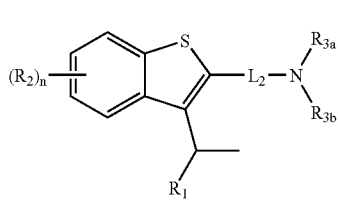
(V-2)

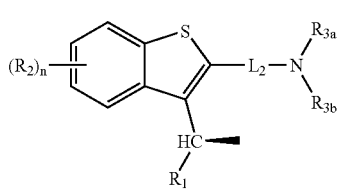
(VI-1)

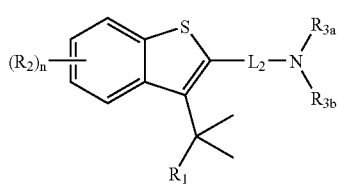
(V-3)

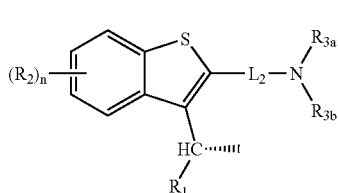
(VI-2)

In still another embodiment, $L_1$ is alkanediyl such as —C(=CH$_2$)— as represented by structure (V-4):

In another embodiment, $L_2$ is alkanediyl such as —CH$_2$— or —CH$_2$CH$_2$—, and compounds of this invention have the following structures (VII-1) or (VII-2), respectively.

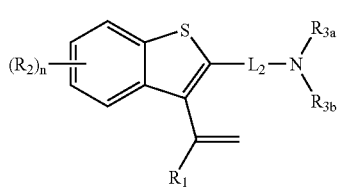
(V-4)

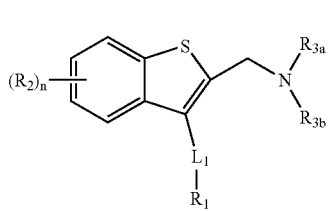
(VII-1)

In yet another embodiment, $L_1$ is substituted alkanediyl such as —C(=O)— as represented by structure (V-5), or —CH(OH)— as represented by structure (V-6):

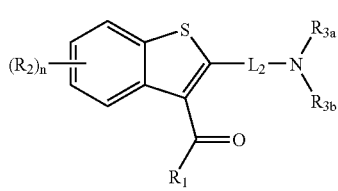
(V-5)

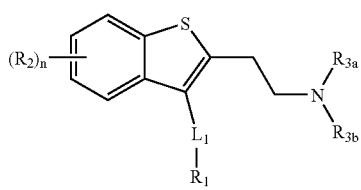
(VII-2)

In a further embodiment, $R_{3a}$ and $R_{3b}$ are the same or different and independently hydrogen, alkyl or substituted alkyl.

In another embodiment, $R_{3a}$ and $R_{3b}$ together with the nitrogen to which they are attached form a heterocycle which is optionally mono- or di-substituted with alkyl or substituted alkyl (in the case of a di-substitution, the alkyl or substituted alkyl moieties may be the same or different). Compounds of this embodiment include, for example, compounds of structures (VIII-1) and (VIII-2), wherein R represents 0, 1 or 2 alkyl or substituted alkyl subsituents, and m is 2, 3, 4 or 5.

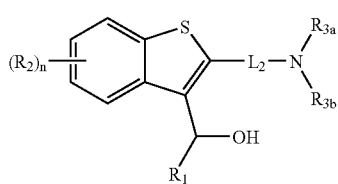
(V-6)

In another embodiment, one or more of the carbon atoms bridging the benzothiophene moiety and the $R_1$ group may be a chiral center. For example, in the case of structure (V-2) above, the bridging carbon atom is chiral when $R_1$ is a moiety other than hydrogen or methyl, as represented by the following structures (VI-1) and (VI-2):

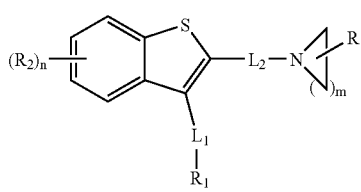
(VIII-1)

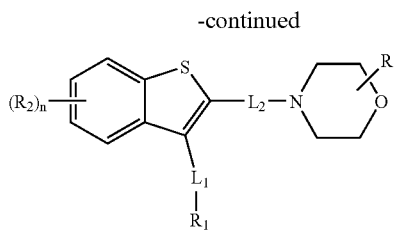

(VIII-2)

In one embodiment R₂ is a lower alkyl, such as, for example, methyl, ethyl, propyl, isopropyl, butyl or sec-butyl. In one such embodiment, R₂ is methyl. In another embodiment R₂ is a lower alkoxy, such as, for example, methoxy, ethoxy, propoxy, isopropoxy or butoxy. In one such embodiment, R₂ is methoxy.

Representative compounds of the present invention include the following compounds:

[2-(2-Dimethylamino-ethyl)-benzo[b]thiophen-3-yl]-(4-fluoro-phenyl)-methanone (Compound 3-1);
{2-[3-(4-Fluoro-benzyl)-benzo[b]thiophen-2-yl]-ethyl}-dimethyl-amine (Compound 3-2);
1-[2-(2-Dimethylamino-ethyl)-benzo[b]thiophen-3-yl]-1-(4-fluoro-phenyl)-ethanol (Compound 3-3);
(2-{3-[1-(4-Fluoro-phenyl)-ethyl]-benzo[b]thiophen-2-yl}-ethyl)-dimethyl-amine (Compound 3-4);
[2-(2-Dimethylamino-ethyl)-benzo[b]thiophen-3-yl]-phenyl-methanone (Compound 3-5);
Dimethyl-{2-[3-(4-methyl-benzyl)-benzo[b]thiophen-2-yl]-ethyl}-amine (Compound 3-6);
[2-(2-Dimethylamino-ethyl)-6-methyl-benzo[b]thiophen-3-yl]-pyridin-2-yl-methanone (Compound 4-1);
Dimethyl-{2-[6-methyl-3-(1-pyridin-2-yl-ethyl)-benzo[b]thiophen-2-yl]-ethyl}-amine (Compound 4-2);
Dimethyl-{2-[6-methyl-3-((R)-1-pyridin-2-yl-ethyl)-benzo[b]thiophen-2-yl]-ethyl}-amine (Compound 4-3);
Dimethyl-{2-[6-methyl-3-((S)-1-pyridin-2-yl-ethyl)-benzo[b]thiophen-2-yl]-ethyl}-amine (Compound 4-4);
1-[2-(2-Dimethylamino-ethyl)-6-methyl-benzo[b]thiophen-3-yl]-1-pyridin-2-yl-ethanol (Compound 4-5);
Dimethyl-{2-[6-methyl-3-(1-pyridin-2-yl-vinyl)-benzo[b]thiophen-2-yl]-ethyl}-amine (Compound 4-6);
[2-(2-Dimethylamino-ethyl)-benzo[b]thiophen-3-yl]-pyridin-2-yl-methanone (Compound 5-1);
Dimethyl-(2-{3-[1-(4-methyl-pyridin-2-yl)-vinyl]-benzo[b]thiophen-2-yl}-ethyl)-amine (Compound 5-2);
Dimethyl-(2-{3-[1-(4-methyl-pyridin-2-yl)-ethyl]-benzo[b]thiophen-2-yl}-ethyl)-amine (Compound 5-3);
1-[2-(2-Dimethylamino-ethyl)-benzo[b]thiophen-3-yl]-1-pyridin-2-yl-ethanol (Compound 6-1);
Dimethyl-{2-[3-(1-pyridin-2-yl-vinyl)-benzo[b]thiophen-2-yl]-ethyl}-amine (Compound 6-2);
Dimethyl-{2-[3-(1-pyridin-2-yl-ethyl)-benzo[b]thiophen-2-yl]-ethyl}-amine (Compound 6-3);
Dimethyl-{2-[3-(1-pyridin-3-yl-vinyl)-benzo[b]thiophen-2-yl]-ethyl}-amine (Compound 6-4);
Dimethyl-{2-[3-(1-pyridin-4-yl-vinyl)-benzo[b]thiophen-2-yl]-ethyl}-amine (Compound 6-5);
Dimethyl-{2-[3-(1-pyridin-3-yl-ethyl)-benzo[b]thiophen-2-yl]-ethyl}-amine (Compound 6-6);
Dimethyl-{2-[3-(1-pyridin-4-yl-ethyl)-benzo[b]thiophen-2-yl]-ethyl}-amine (Compound 6-7);
Dimethyl-{2-[3-((R)-1-pyridin-3-yl-ethyl)-benzo[b]thiophen-2-yl]-ethyl}-amine (Compound 6-8);
Dimethyl-{2-[3-((S)-1-pyridin-3-yl-ethyl)-benzo[b]thiophen-2-yl]-ethyl}-amine (Compound 6-9);
Dimethyl-(2-{3-[1-(3-methoxy-pyridin-2-yl)-ethyl]-benzo[b]thiophen-2-yl}-ethyl)-amine (Compound 6-10);
Dimethyl-(2-{3-[(R)-1-(3-methyl-pyridin-2-yl)-ethyl]-benzo[b]thiophen-2-yl}-ethyl)-amine (Compound 6-11);
Dimethyl-(2-{3-[(S)-1-(3-methyl-pyridin-2-yl)-ethyl]-benzo[b]thiophen-2-yl}-ethyl)-amine (Compound 6-12);
1-[2-(2-Dimethylamino-ethyl)-benzo[b]thiophen-3-yl]-1-(5-fluoro-pyridin-2-yl)-ethanol (Compound 7-1);
(2-{3-[1-(5-Fluoro-pyridin-2-yl)-vinyl]-benzo[b]thiophen-2-yl}-ethyl)-dimethyl-amine (Compound 7-2);
(2-{3-[1-(5-Fluoro-pyridin-2-yl)-ethyl]-benzo[b]thiophen-2-yl}-ethyl)-dimethyl-amine (Compound 7-3);
(2-{3-[(R)-1-(5-Fluoro-pyridin-2-yl)-ethyl]-benzo[b]thiophen-2-yl}-ethyl)-dimethyl-amine (Compound 7-4);
(2-{3-[(S)-1-(5-Fluoro-pyridin-2-yl)-ethyl]-benzo[b]thiophen-2-yl}-ethyl)-dimethyl-amine (Compound 7-5);
1-[2-(2-Dimethylamino-ethyl)-benzo[b]thiophen-3-yl]-1-thiazol-2-yl-ethanol (Compound 8-1);
Dimethyl-{2-[3-(1-thiazol-2-yl-vinyl)-benzo[b]thiophen-2-yl]-ethyl}-amine (Compound 8-2);
Dimethyl-{2-[3-(1-thiazol-2-yl-ethyl)-benzo[b]thiophen-2-yl]-ethyl}-amine (Compound 8-3);
Methyl-{2-[3-(1-pyridin-2-yl-ethyl)-benzo[b]thiophen-2-yl]-ethyl}-amine (Compound 9-1);
Methyl-propyl-{2-[3-(1-pyridin-2-yl-ethyl)-benzo[b]thiophen-2-yl]-ethyl}-amine (Compound 9-2);
1-[2-(2-Dimethylamino-ethyl)-benzo[b]thiophen-3-yl]-1-(6-methyl-pyridin-3-yl)-ethanol (Compound 10-1);
Dimethyl-(2-{3-[1-(6-methyl-pyridin-3-yl)-vinyl]-benzo[b]thiophen-2-yl}-ethyl)-amine (Compound 10-2);
Dimethyl-(2-{3-[1-(6-methyl-pyridin-3-yl)-ethyl]-benzo[b]thiophen-2-yl}-ethyl)-amine (Compound 10-3);
1-[2-(2-Dimethylamino-ethyl)-benzo[b]thiophen-3-yl]-1-pyrazin-2-yl-ethanol (Compound 11-1);
Dimethyl-{2-[3-(1-pyrazin-2-yl-ethyl)-benzo[b]thiophen-2-yl]-ethyl}-amine (Compound 11-2);
Dimethyl-{2-[3-((R)-1-pyrazin-2-yl-ethyl)-benzo[b]thiophen-2-yl]-ethyl}-amine (Compound 11-3);
Dimethyl-{2-[3-((S)-1-pyrazin-2-yl-ethyl)-benzo[b]thiophen-2-yl]-ethyl}-amine (Compound 11-4);
Dimethyl-{2-[3-((S)-1-pyridin-2-yl-ethyl)-benzo[b]thiophen-2-yl]-ethyl}-amine (Compound 12-1);
Dimethyl-{2-[3-((R)-1-pyridin-2-yl-ethyl)-benzo[b]thiophen-2-yl]-ethyl}-amine (Compound 12-2);
[2-(2-Dimethylamino-ethyl)-benzo[b]thiophen-3-yl]-pyridin-2-yl-methanol (Compound 13-1);
[2-(2-Dimethylamino-ethyl)-benzo[b]thiophen-3-yl]-pyrimidin-5-yl-methanol (Compound 13-2);
Dimethyl-[2-(3-pyridin-2-ylmethyl-benzo[b]thiophen-2-yl)-ethyl]-amine (Compound 13-3);
Dimethyl-[2-(3-pyrimidin-5-ylmethyl-benzo[b]thiophen-2-yl)-ethyl]-amine (Compound 13-4);
Dimethyl-[2-(3-thiazol-2-ylmethyl-benzo[b]thiophen-2-yl)-ethyl]-amine (Compound 13-5);
Dimethyl-[2-(3-thiazol-4-ylmethyl-benzo[b]thiophen-2-yl)-ethyl]-amine (Compound 13-6);
{2-[3-(3-Methoxy-pyridin-2-ylmethyl)-benzo[b]thiophen-2-yl]-ethyl}-dimethyl-amine (Compound 13-7);
6-[2-(2-Dimethylamino-ethyl)-benzo[b]thiophen-3-ylmethyl]-pyridin-2-ol (Compound 13-8);
Dimethyl-[2-(3-pyrazin-2-ylmethyl-benzo[b]thiophen-2-yl)-ethyl]-amine (Compound 13-9);
[2-(3-Furan-2-ylmethyl-benzo[b]thiophen-2-yl)-ethyl]-dimethyl-amine (Compound 13-10);
Dimethyl-{2-[3-(3-methyl-3H-imidazol-4-ylmethyl)-benzo[b]thiophen-2-yl]-ethyl}-amine (Compound 13-11);

Dimethyl-[2-(3-[1,2,3]thiadiazol-5-ylmethyl-benzo[b]
thiophen-2-yl)-ethyl]-amine (Compound 13-12);
{2-[3-(2,5-Dimethyl-2H-pyrazol-3-ylmethyl)-benzo[b]
thiophen-2-yl]-ethyl}-dimethyl-amine (Compound 13-13);
{2-[3-(4-Chloro-1-methyl-1H-pyrazol-3-ylmethyl)-benzo
[b]thiophen-2-yl]-ethyl}-dimethyl-amine (Compound 13-14);
Dimethyl-{2-[3-(1-methyl-1H-imidazol-2-ylmethyl)-benzo
[b]thiophen-2-yl]-ethyl}-amine (Compound 13-15);
[2-(2-Dimethylamino-ethyl)-benzo[b]thiophen-3-yl]-thiazol-4-yl-methanol (Compound 14-1);
[2-(2-Dimethylamino-ethyl)-benzo[b]thiophen-3-yl]-thiazol-4-yl-methanone (Compound 14-2);
[2-(2-Pyrrolidin-1-yl-ethyl)-benzo[b]thiophen-3-yl]-thiazol-4-yl-methanone (Compound 14-3);
[2-(2-Dimethylamino-ethyl)-benzo[b]thiophen-3-yl]-thiazol-5-yl-methanone (Compound 14-4);
[2-(2-Dimethylamino-ethyl)-benzo[b]thiophen-3-yl]-2-methoxy-pyridin-3-yl-methanone (Compound 14-5);
2-(2-Dimethylamino-ethyl)-benzo[b]thiophen-3-yl]-2-fluoro-pyridin-3-yl-methanone (Compound 14-6);
2-(2-Dimethylamino-ethyl)-benzo[b]thiophen-3-yl]-2-methoxy-pyridin-6-yl-methanone (Compound 14-7);
2-(2-Dimethylamino-ethyl)-benzo[b]thiophen-3-yl]-2-fluoro-pyridin-6-yl-methanone (Compound 14-8);
2-(2-Dimethylamino-ethyl)-benzo[b]thiophen-3-yl]-4-methoxy-pyridin-3-yl-methanone (Compound 14-9);
2-(2-Dimethylamino-ethyl)-benzo[b]thiophen-3-yl]-3-fluoro-pyridin-2-yl-methanone (Compound 14-10);
(2-{3-[1-(6-Methoxy-pyridin-2-yl)-vinyl]-benzo[b]
thiophen-2-yl}-ethyl)-dimethyl-amine (Compound 15-1);
(2-{3-[1-(6-Methoxy-pyridin-2-yl)-ethyl]-benzo[b]
thiophen-2-yl}-ethyl)-dimethyl-amine (Compound 15-2);
(2-{3-[1-(6-fluoro-pyridin-2-yl)-vinyl]-benzo[b]thiophen-2-yl}-ethyl)-dimethyl-amine (Compound 15-3);
Dimethyl-(2-{3-[1-(2-methoxy-pyridin-3-yl)-ethyl]-benzo
[b]thiophen-2-yl}-ethyl)-amine (Compound 15-4);
Dimethyl-(2-{3-[(R)-1-(2-methoxy-pyridin-3-yl)-ethyl]-benzo[b]thiophen-2-yl}-ethyl)-amine (Compound 15-5);
Dimethyl-(2-{3-[(S)-1-(2-methoxy-pyridin-3-yl)-ethyl]-benzo[b]thiophen-2-yl}-ethyl)-amine (Compound 15-6);
Dimethyl-(2-{3-[1-(2-fluoro-pyridin-3-yl)-ethyl]-benzo[b]
thiophen-2-yl}-ethyl)-amine (Compound 15-7);
Dimethyl-(2-{3-[(R)-1-(2-fluoro-pyridin-3-yl)-ethyl]-benzo
[b]thiophen-2-yl}-ethyl)-amine (Compound 15-8);
Dimethyl-(2-{3-[(S)-1-(2-fluoro-pyridin-3-yl)-ethyl]-benzo
[b]thiophen-2-yl}-ethyl)-amine (Compound 15-9);
1-[2-(2-Dimethylamino-ethyl)-benzo[b]thiophen-3-yl]-1-thiazol-4-yl-ethanol (Compound 16-1);
Dimethyl-{2-[3-(1-thiazol-4-yl-ethyl)-benzo[b]thiophen-2-yl]-ethyl}-amine (Compound 16-2);
Dimethyl-{2-[3-((R)-1-thiazol-4-yl-ethyl)-benzo[b]
thiophen-2-yl]-ethyl}-amine (Compound 16-3);
Dimethyl-{2-[3-((R)-1-thiazol-4-yl-ethyl)-benzo[b]
thiophen-2-yl]-ethyl}-amine (Compound 16-4);
(2-{3-[1-(4-Methoxy-pyridin-3-yl)-ethyl]-benzo[b]
thiophen-2-yl}-ethyl)-dimethyl-amine (Compound 16-5);
(2-{3-[1-(4-Hydroxy-pyridin-3-yl)-ethyl]-benzo[b]
thiophen-2-yl}-ethyl)-dimethyl-amine (Compound 16-6);
1-[2-(2-Dimethylamino-ethyl)-benzo[b]thiophen-3-yl]-1-thiazol-5-yl-ethanol (Compound 17-1);
Dimethyl-{2-[3-(1-thiazol-5-yl-ethyl)-benzo[b]thiophen-2-yl]-ethyl}-amine (Compound 17-2);
Dimethyl-{2-[3-((R)-1-thiazol-5-yl-ethyl)-benzo[b]
thiophen-2-yl]-ethyl}-amine (Compound 17-3);

Dimethyl-{2-[3-((S)-1-thiazol-5-yl-ethyl)-benzo[b]
thiophen-2-yl]-ethyl}-amine (Compound 17-4);
1-[2-(2-Dimethylamino-ethyl)-benzo[b]thiophen-3-yl]-1-(3-fluoro-pyridin-2-yl)-ethanol (Compound 18-1);
(2-{3-[1-(3-Fluoro-pyridin-2-yl)-vinyl]-benzo[b]thiophen-2-yl)}-ethyl)-dimethyl-amine (Compound 18-2);
(2-{3-[1-(3-Fluoro-pyridin-2-yl)-ethyl]-benzo[b]thiophen-2-yl}-ethyl)-dimethyl-amine (Compound 18-3);
(2-{3-[(R)-1-(3-Fluoro-pyridin-2-yl)-ethyl]-benzo[b]
thiophen-2-yl}-ethyl)-dimethyl-amine (Compound 18-4);
(2-{3-[(S)-1-(3-Fluoro-pyridin-2-yl)-ethyl]-benzo[b]
thiophen-2-yl}-ethyl)-dimethyl-amine (Compound 18-5);
[2-(2-Pyrrolidin-1-yl-ethyl)-benzo[b]thiophen-3-yl]-thiazol-4-yl-methanone (Compound 19-1);
1-[2-(2-Pyrrolidin-1-yl-ethyl)-benzo[b]thiophen-3-yl]-1-thiazol-4-yl-ethanol (Compound 19-2);
4-{1-[2-(2-Pyrrolidin-1-yl-ethyl)-benzo[b]thiophen-3-yl]-vinyl}-thiazole (Compound 19-3);
4-{1-[2-(2-Pyrrolidin-1-yl-ethyl)-benzo[b]thiophen-3-yl]-ethyl}-thiazole (Compound 19-4);
4-{(R)-1-[2-(2-Pyrrolidin-1-yl-ethyl)-benzo[b]thiophen-3-yl]-ethyl}-thiazole (Compound 19-5);
4-{(S)-1-[2-(2-Pyrrolidin-1-yl-ethyl)-benzo[b]thiophen-3-yl]-ethyl}-thiazole (Compound 19-6);
2-{1-[2-(2-Pyrrolidin-1-yl-ethyl)-benzo[b]thiophen-3-yl]-ethyl}-pyridine (Compound 20-1);
2-{(S)-1-[2-(2-Pyrrolidin-1-yl-ethyl)-benzo[b]thiophen-3-yl]-ethyl}-pyridine (Compound 20-2);
2-{(R)-1-[2-(2-Pyrrolidin-1-yl-ethyl)-benzo[b]thiophen-3-yl]-ethyl}-pyridine (Compound 20-3);
2-(1-{2-[2-(2,5-Dihydro-pyrrol-1-yl)-ethyl]-benzo[b]
thiophen-3-yl}-ethyl)-pyridine (Compound 20-4);
4-{2-[3-(1-Pyridin-2-yl-ethyl)-benzo[b]thiophen-2-yl]-ethyl}-morpholine (Compound 20-5);
1-{2-[3-(1-Pyridin-2-yl-ethyl)-benzo[b]thiophen-2-yl]-ethyl}-pyrrolidin-3-ol (Compound 20-6);
2-{1-[2-(2-Azetidin-1-yl-ethyl)-benzo[b]thiophen-3-yl]-ethyl}-pyridine (Compound 20-7);
2-{(R)-1-[2-(2-Azetidin-1-yl-ethyl)-benzo[b]thiophen-3-yl]-ethyl}-pyridine (Compound 20-8);
2-{(S)-1-[2-(2-Azetidin-1-yl-ethyl)-benzo[b]thiophen-3-yl]-ethyl}-pyridine (Compound 20-9);
Methyl-{2-[3-((R)-1-pyridin-2-yl-ethyl)-benzo[b]thiophen-2-yl]-ethyl}-amine (Compound 21-1);
1-[2-(2-Dimethylamino-ethyl)-benzo[b]thiophen-3-yl]-2-methoxy-ethanone (Compound 22-1);
{2-[3-(2-Methoxy-ethyl)-benzo[b]thiophen-2-yl]-ethyl}-dimethyl-amine (Compound 22-2);
1-[2-(2-Dimethylamino-ethyl)-benzo[b]thiophen-3-yl]-propan-2-ol (Compound 23-1);
{2-[3-(2-Methoxy-propyl)-benzo[b]thiophen-2-yl]-ethyl}-dimethyl-amine (Compound 23-2);
[2-(2-Dimethylamino-ethyl)-benzo[b]thiophen-3-yl]-(2-fluoro-pyridin-3-yl)-methanol (Compound 24-1);
{2-[3-(2-Fluoro-pyridin-3-ylmethyl)-benzo[b]thiophen-2-yl]-ethyl}-dimethyl-amine (Compound 24-2);
(2-Chloro-pyridin-3-yl)-[2-(2-dimethylamino-ethyl)-benzo
[b]thiophen-3-yl]-methanone (Compound 25-1);
1-(2-Chloro-pyridin-3-yl)-1-[2-(2-dimethylamino-ethyl)-benzo[b]thiophen-3-yl]-ethanol (Compound 25-2);
(2-{3-[1-(2-Chloro-pyridin-3-yl)-vinyl]-benzo[b]thiophen-2-yl}-ethyl)-dimethyl-amine (Compound 25-3);
(2-{3-[1-(2-Chloro-pyridin-3-yl)-ethyl]-benzo[b]thiophen-2-yl}-ethyl)-dimethyl-amine (Compound 25-4);
(2-{3-[(R)-1-(2-Chloro-pyridin-3-yl)-ethyl]-benzo[b]
thiophen-2-yl}-ethyl)-dimethyl-amine (Compound 25-5);
and (2-{3-[(S)-1-(2-Chloro-pyridin-3-yl)-ethyl]-benzo[b]
thiophen-2-yl}-ethyl)-dimethyl-amine (Compound 25-6).

Representative compounds of the present invention also include the following compounds and their respective enantiomers:

2-((R)-1-{2-[2-(3-Fluoro-azetidin-1-yl)-ethyl]-benzo[b]
thiophen-3-yl}-ethyl)-pyridine;
2-((R)-1-{2-[2-(3-Fluoro-azetidin-1-yl)-ethyl]-benzo[b]
thiophen-3-yl}-ethyl)-3-methoxy-pyridine;
3-Fluoro-2-((R)-1-{2-[2-(3-fluoro-azetidin-1-yl)-ethyl]-
benzo[b]thiophen-3-yl}-ethyl)-pyridine;
3-((S)-1-{2-[2-(3-Fluoro-azetidin-1-yl)-ethyl]-benzo[b]
thiophen-3-yl}-ethyl)-2-methoxy-pyridine;
2-Fluoro-3-((S)-1-{2-[2-(3-fluoro-azetidin-1-yl)-ethyl]-
benzo[b]thiophen-3-yl}-ethyl)-pyridine;
4-((R)-1-{2-[2-(3-Fluoro-azetidin-1-yl)-ethyl]-benzo[b]
thiophen-3-yl}-ethyl)-thiazole;
1-{2-[3-((R)-1-Pyridin-2-yl-ethyl)-benzo[b]thiophen-2-yl]-
ethyl}-azetidin-3-ol;
1-(2-{3-[(R)-1-(3-Methoxy-pyridin-2-yl)-ethyl]-benzo[b]
thiophen-2-yl}-ethyl)-azetidin-3-ol;
1-(2-{3-[(R)-1-(3-Fluoro-pyridin-2-yl)-ethyl]-benzo[b]
thiophen-2-yl}-ethyl)-azetidin -3-ol;
1-(2-{3-[(S)-1-(2-Methoxy-pyridin-3-yl)-ethyl]-benzo[b]
thiophen-2-yl}-ethyl)-azetidin-3-ol;
1-(2-{3-[(S)-1-(2-Fluoro-pyridin-3-yl)-ethyl]-benzo[b]
thiophen-2-yl}-ethyl)-azetidin-3-ol;
1-{2-[3-((R)-1-Thiazol-4-yl-ethyl)-benzo[b]thiophen-2-yl]-
ethyl}-azetidin-3-ol;
2-((R)-1-{2-[2-(3-Methoxy-azetidin-1-yl)-ethyl]-benzo[b]
thiophen-3-yl}-ethyl)-pyridine;
3-Methoxy-2-((R)-1-{2-[2-(3-methoxy-azetidin-1-yl)-
ethyl]-benzo[b]thiophen-3-yl}-ethyl)-pyridine;
3-Fluoro-2-((R)-1-{2-[2-(3-methoxy-azetidin-1-yl)-ethyl]-
benzo[b]thiophen-3-yl}-ethyl)-pyridine;
2-Fluoro-3-((S)-1-{2-[2-(3-methoxy-azetidin-1-yl)-ethyl]-
benzo[b]thiophen-3-yl}-ethyl)-pyridine;
2-Methoxy-3-((S)-1-{2-[2-(3-methoxy-azetidin-1-yl)-
ethyl]-benzo[b]thiophen-3-yl}-ethyl)-pyridine;
4-((R)-1-{2-[2-(3-Methoxy-azetidin-1-yl)-ethyl]-benzo[b]
thiophen-3-yl}-ethyl)-thiazole;
4-((R)-1-{2-[2-(3-Fluoro-pyrrolidin-1-yl)-ethyl]-benzo[b]
thiophen-3-yl}-ethyl)-thiazole;
2-((R)-1-{2-[2-(3-Fluoro-pyrrolidin-1-yl)-ethyl]-benzo[b]
thiophen-3-yl}-ethyl)-pyridine;
2-((R)-1-{2-[2-(3-Fluoro-pyrrolidin-1-yl)-ethyl]-benzo[b]
thiophen-3-yl}-ethyl)-3-methoxy-pyridine;
3-Fluoro-2-((R)-1-{2-[2-(3-fluoro-pyrrolidin-1-yl)-ethyl]-
benzo[b]thiophen-3-yl}-ethyl)-pyridine;
3-((S)-1-{2-[2-(3-Fluoro-pyrrolidin-1-yl)-ethyl]-benzo[b]
thiophen-3-yl}-ethyl)-2-methoxy-pyridine;
2-Fluoro-3-((S)-1-{2-[2-(3-fluoro-pyrrolidin-1-yl)-ethyl]-
benzo[b]thiophen-3-yl}-ethyl)-pyridine;
2-Fluoro-3-{(S)-1-[2-(2-thiazolidin-3-yl-ethyl)-benzo[b]
thiophen-3-yl]-ethyl}-pyridine;
2-Methoxy-3-{(S)-1-[2-(2-thiazolidin-3-yl-ethyl)-benzo[b]
thiophen-3-yl]-ethyl}-pyridine;
3-Methoxy-2-{(R)-1-[2-(2-thiazolidin-3-yl-ethyl)-benzo[b]
thiophen-3-yl]-ethyl}-pyridine;
3-Fluoro-2-{(R)-1-[2-(2-thiazolidin-3-yl-ethyl)-benzo[b]
thiophen-3-yl]-ethyl}-pyridine; and
4-{(R)-1-[2-(2-Thiazolidin-3-yl-ethyl)-benzo[b]thiophen-3-
yl]-ethyl}-thiazole.

The compounds of the present invention may generally be utilized as the free base. Alternatively, the compounds of this invention may be used in the form of acid addition salts. In cases where compounds of the present invention contain acidic groups, they may be used either as the free acid or base addition salt. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the acid anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the compounds of structure (I). Further, in the case of a carboxylic acid (—COOH), esters may be employed, such as methyl esters, ethyl esters, and the like.

With regard to stereoisomers, the compounds of structure (I) may have chiral centers and may occur as racemates, racemic mixtures and as individual enantiomers or diastereomers. All such isomeric forms are included within the present invention, including mixtures thereof. Compounds of structure (I) may also possess axial chirality, which may result in atropisomers. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

The compounds of this invention may be prepared by known organic synthesis techniques, including the general schemes set forth below and as described in more detail in the Examples.

Reaction Scheme 1

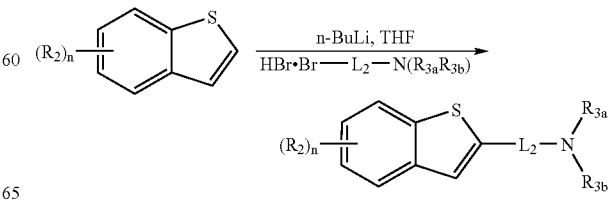

Substitution at the 2-position of the benzothiophene nucleus is available to the aminoalkylbromide hydrobromide in the presence of n-BuLi in anhydrous THF in cases where the alkyl functionality is ethyl or a higher homolog.

Reaction Scheme 2

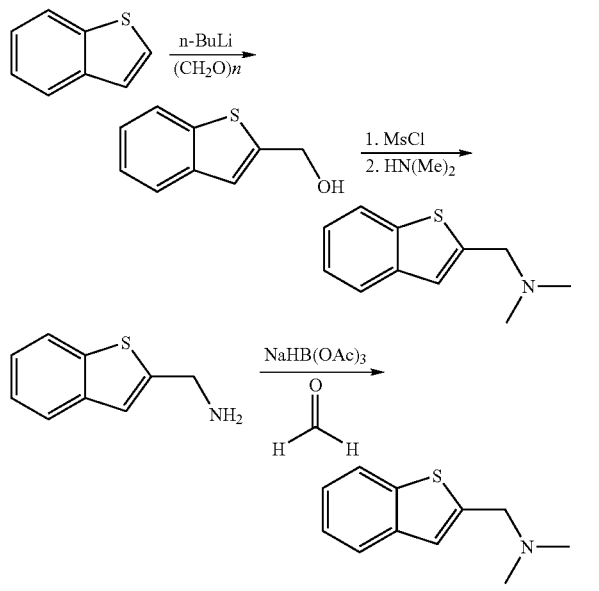

Introduction of $L_2$ as the methylene can proceed via multiple routes, as for example the reaction of n-BuLi/$(CH_2O)_n$ with the benzothiophene and subsequent reaction of the mesylated intermediate with $HN(Me)_2$, or the reaction of the aminomethylbenzothiophene with $NaHB(OAc)_3$ and an appropriate aldehyde such as formaldehyde above.

Reaction Scheme 3

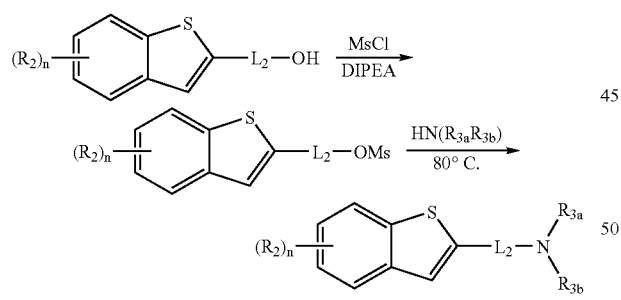

The route from the alcohol to the 2-substituted aminoalkylbenzothiophene is generally available, proceeding from the alcohol through a mesylated intermediate with subsequent amination.

Reaction Scheme 4

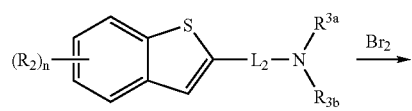

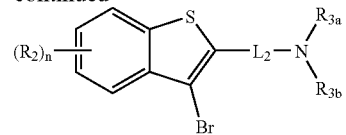

The 3-bromo compound, an intermediate in the synthesis of compounds of the invention, is afforded by reaction of $Br_2$ with the substituted aminoalkylbenzothiophene.

Reaction Scheme 5

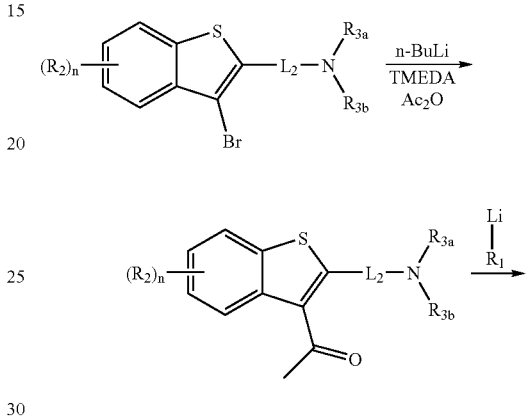

The 3-bromo compound above reacts with n-BuLi, TMEDA, and $Ac_2O$ to form the ethanone. The ethanone reacts with the lithiated (optionally) substituted aryl or heteroaryl $R_1$ which compound is generated in situ by reaction of the brominated $R_1$ with n-BuLi in anhydrous solution at low temperature. Addition of $R_1$ gives the alcohol, which can be dehydrated to the vinyl compound, as for example with $H_2SO_4$. The vinyl compound can be reduced, for example with catalytic hydrogenation.

Reaction Scheme 6

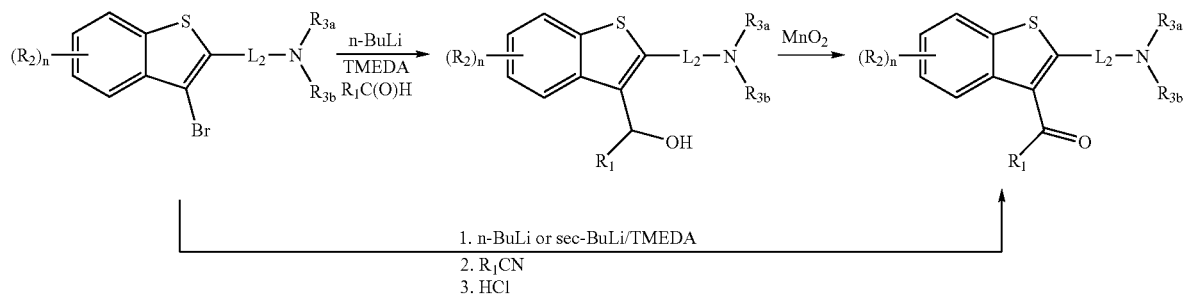

The 3-bromo compound above reacts with n-BuLi, TMEDA and an aldehyde to form the alcohol. The alcohol can be oxidized to the ketone with, for example, manganese (IV)oxide. Alternatively, the bromo compound can be reacted with n- or sec-BuLi in the presence of TMEDA followed by addition of a nitrile and subsequent hydrolysis to the ketone.

Reaction Scheme 7

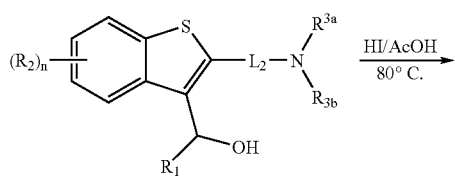

-continued

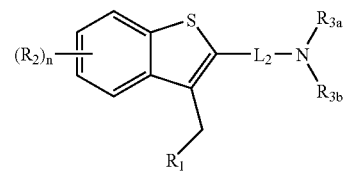

The alcohol intermediate can be deoxgenated using hydro iodic acid in the presence of acetic acid.

Reaction Scheme 8

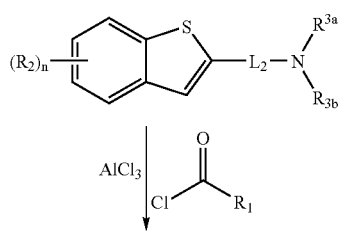

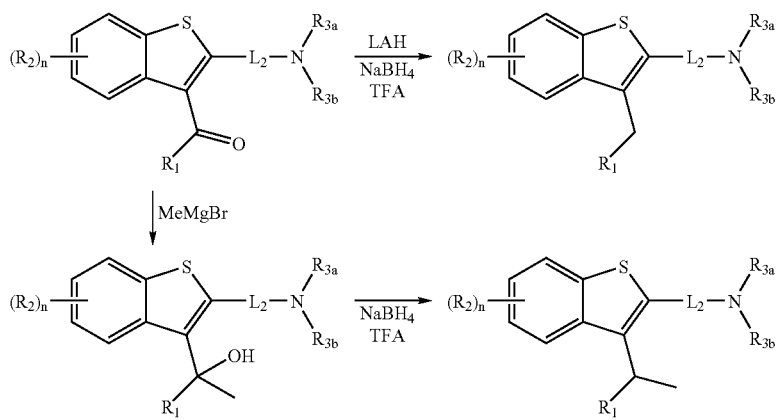

Another synthetic route to substitution at the 3-position of benzothiophene employs the AlCl₃ mediated substitution reaction with the acyl chloride to give the ketone. The ketone can be reduced in a multistep reaction employing LAH in THF followed by NaBH₄ in TFA. Alternatively, the ketone can be alkylated in a Grignard reaction to the alcohol which can be reduced, as for example with NaBH₄ in TFA.

Reaction Scheme 9

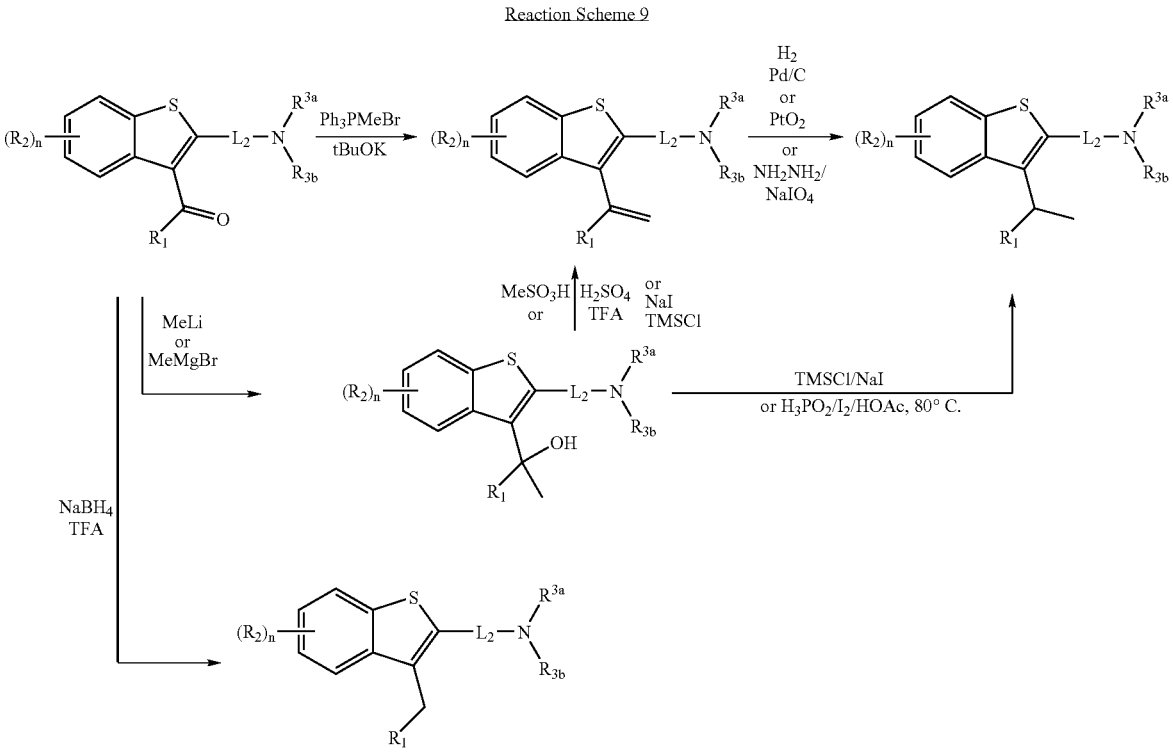

The ketone intermediate can undergo a Wittig reaction to generate the corresponding vinyl compound. The vinyl compound can also be prepared by addition of methyl lithium or methyl grignard to the ketone generating the alcohol intermediate followed by dehydration with reagents such as methylsulfonic acid, sulfuric acid in trifluoro acetic acid or sodium iodide in the presence of trimethyl silyl chloride. The vinyl compound can be reduced by catalytic hydrogenation or by hydrazine in the presence of sodium periodate. Alternatively, the hydroxyl intermediate can be directly deoxgenated by sodium iodide in the presence of trimethylsilyl chloride or hypophosporus acid and iodine in acetic acid. The ketone intermediate can also be fully reduced to the alkyl compound by sodium borohydride in TFA.

Reaction Scheme 10

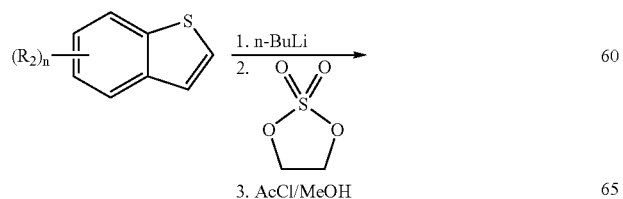

-continued

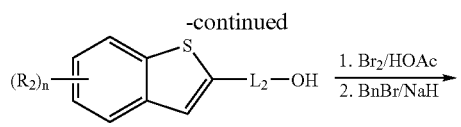

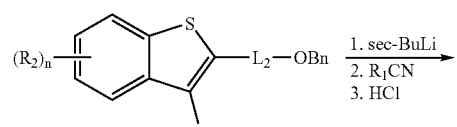

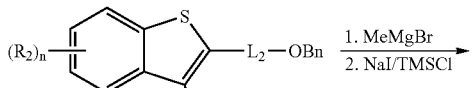

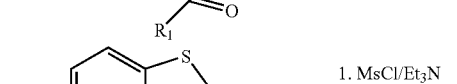

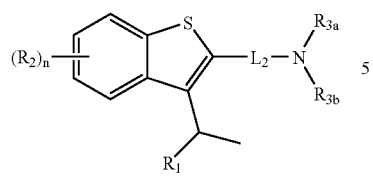

The amine substituents can be varied using the reaction sequence shown above. Benzothiophene, optionally substituted in the 4-7 position, can be reacted with n-Butyl lithium and [1,3,2]Dioxathiolane 2,2-dioxide. The formed sulfate can be hydrolyzed to the alcohol using hydrogen chloride generated by acetyl chloride in MeOH. Subsequent bromination using Bromine in acetic acid followed by protection of the alcohol with a benzyl group can generate the OBenzyl bromo compound. Lithiation of the bromo OBenzyl compound with sec-BuLi followed by reaction with a nitrile and subsequent hydrolysis will generate the ketone. This ketone can be reacted with methyl grignard reagent to generate the alcohol. Treatment of the alcohol with sodium iodide and trimethylsilyl chloride can accomplish the deoxgenation and debenzylation in one step. Subsequent mesylation can be followed by displacement of the mesylate with a variety of amines.

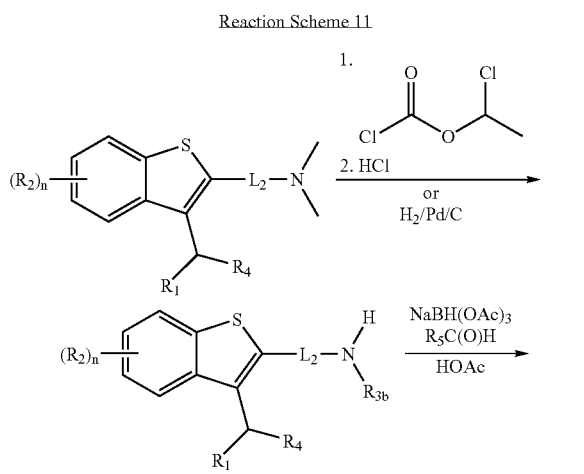

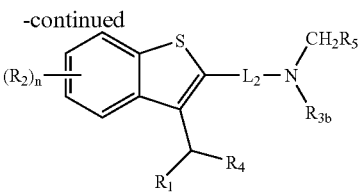

A dimethylamine compound can be reacted with 1-ethylchloroformate followed by treatment with HCl to remove one of the N-methyl substituents. In some instances this transformation can also be accomplished by catalytic hydrogenation. The monomethyl amine compound can be treated with sodium triacetoxy borohydride and an aldehyde or ketone to install different amine substituents.

The bromo compound can be transformed to the corresponding lithio compound with n-BuLi in the presence of TMEDA. Subsequent reaction with optionally substituted epoxide will generate a mixture of addition products. These alcohols can be mesylated and the mesylate group can be displaced with different alkoxy compounds.

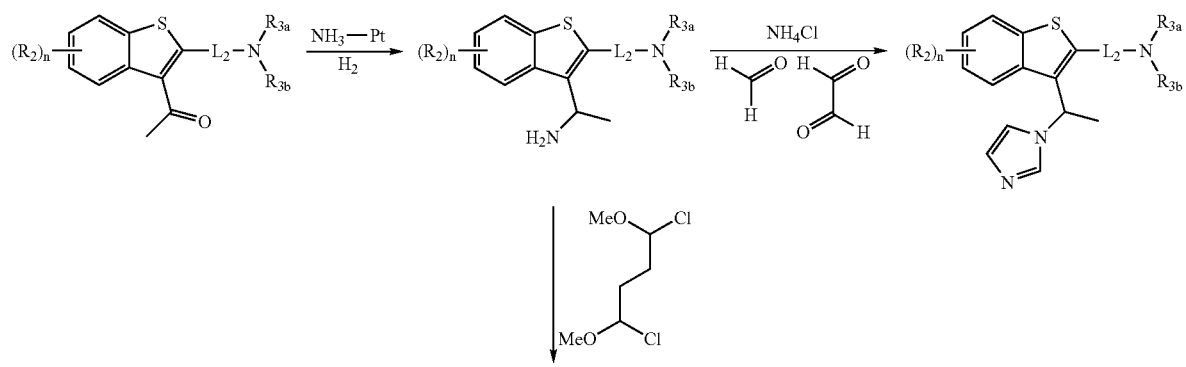

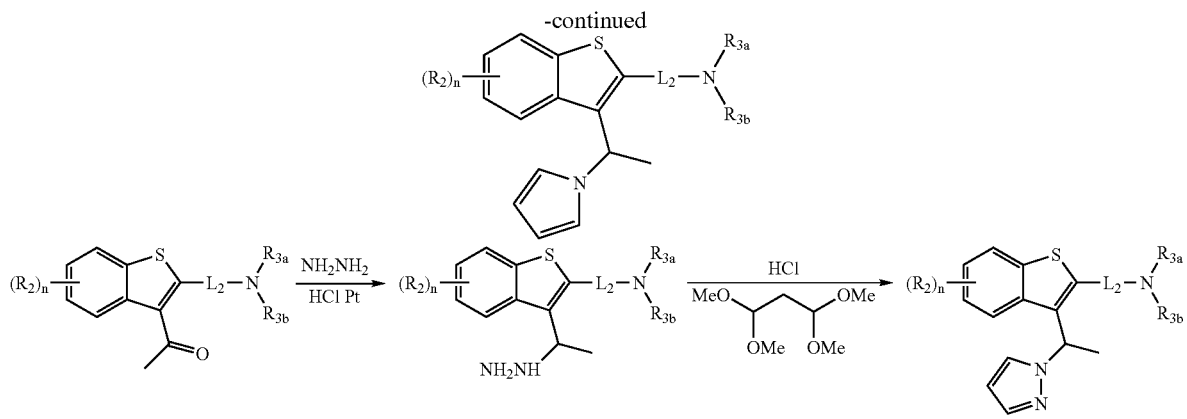

The primary amine can be prepared from the acetyl by reaction with ammonia and reduction with hydrogen in presence of Pt catalyst. It can then be used for the preparation of the pyrrole by reaction with 1,4-dichloro-1,4-dimethoxybutane. The same amine can also be reacted with formaldehyde and glyoxal to generate the imidazole. Hydrazine can be added to the acetyl followed by a reduction with HCl and Pt to generate the hydrazine. Subsequent reaction with 1,1,3,3-tetramethoxypropane allows the preparation of the pyrazole ring.

The compounds of this invention may be evaluated for their ability to bind to histamine receptor ligands, which may be determined by techniques known in this field. For example, Example 26 provides a general procedure for calculating the binding to the histamine $H_1$ receptor by a standard binding assay, while Example 27 provides a general procedure for determining the sedative effects of test compounds employing electroencephalography and electromyography.

As mentioned above, the compounds of this invention generally may be capable of functioning as ligands to one or more histamine receptors, and therefore may be useful in the treatment of a variety of conditions or diseases associated therewith. In this manner, the compounds function by altering or regulating the activity of a histamine receptor, thereby providing a treatment for a condition or disease associated with that receptor. Thus, the compounds of this invention may have utility over a broad range of therapeutic applications, and may be used to treat disorders or illnesses, including (but not limited to) sleep disorders.

Compounds of the present invention may be advantageous as sedative hypnotics as they show one or more enhancements over previously known antihistamines. Some advantages of compounds of the present invention may include an enhanced selectivity profile for $H_1$ receptor relative to other G-protein coupled receptors and other proteins in comparison to other known sedating $H_1$ ligands. Effects on sleep processes are therefore more specific. Compounds of the present invention may also show reduced inhibition of cytochrome $P_{450}$ (CYP) enzymes that potentiate drug interactions as well as other proteins associated with the safety of pharmaceuticals such as the human ether a go-go (hERG) channel. Compounds of the present invention may also show favorable characteristics relative to other known antihistamines including but not limited to improved efficacy, improved quality of sleep, lack of peripheral side effects and optimal pharmacokinetics for use as a sedative.

In another embodiment, pharmaceutical compositions containing one or more compounds of this invention are disclosed. For the purposes of administration, the compounds of the present invention may be formulated as pharmaceutical compositions. Pharmaceutical compositions of the present invention comprise a compound of structure (I) and a pharmaceutically acceptable carrier and/or diluent. The compound is present in the composition in an amount which is effective to treat a particular disorder of interest, and preferably with acceptable toxicity to the patient. Typically, the pharmaceutical composition may include a compound of this invention in an amount ranging from 0.1 mg to 250 mg per dosage depending upon the route of administration, and more typically from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets that contain, in addition to a compound of this invention, dispersing and surface active agents, binders, and lubricants. One skilled in this art may further formulate the compound in an appropriate manner, and in accordance with accepted practices, such as those disclosed in *Remington's Pharmaceutical Sciences,* Gennaro, Ed., Mack Publishing Co., Easton, Pa. 1990.

In another embodiment, the present invention provides a method for treating a condition related to a histamine receptor. Such methods include administration of a compound of the present invention to a warm-blooded animal (including a human) in an amount sufficient to treat the condition. In this context, "treat" includes prophylactic administration. Such methods include systemic administration of compound of this invention, preferably in the form of a pharmaceutical composition as discussed above. As used herein, systemic administration includes oral and parenteral methods of administration. For oral administration, suitable pharmaceutical compositions include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions that may contain buffers, antioxidants, bacteriostats, and other additives commonly employed in such solutions.

The following examples are provided for purposes of illustration and not limitation.

EXAMPLES

Analytical HPLC-MS Method 1

Platform: Agilent 1100 series: equipped with an auto-sampler, an UV detector (220 nM and 254 nM), a MS detector (APCI) and Berger FCM 1200 $CO_2$ pump module;

HPLC column: Berger Pyridine, PYR 60A, 6μ, 4.6×150 mm column;

HPLC gradient: 4.0 mL/minute, 120 bar; from 10% methanol in supercritical $CO_2$ to 60% methanol in supercritical $CO_2$ in 1.67 minutes, maintaining 60% for 1 minute. Methanol has 1.5% water. Backpressure regulated at 140 bar.

Analytical HPLC-MS Method 2

Platform: Agilent 1100 series: equipped with an auto-sampler, an UV detector (220 nM and 254 nM), a MS detector (APCI);

HPLC column: Phenomenex Synergi-Max RP, 2.0×50 mm column;

HPLC gradient: 1.0 mL/minute, from 5% acetonitrile in water to 95% acetonitrile in water in 13.5 minutes, maintaining 95% for 2 minute. Both acetonitrile and water have 0.025% TFA.

Analytical HPLC-MS Method 3

Platform: Agilent 1100 series: equipped with a Gilson 215 auto-sampler/fraction collector, a UV detector (220 nM and 254 nM), and a MS detector (electrospray);

HPLC column: BHK ODS-O/B, 5μ, 4.6×150 mm;

HPLC gradient: 3.6 mL/minute, from 10% acetonitrile in water to 100% acetonitrile in 15 minutes, maintain 100% acetonitrile for 0.50 minutes. Both acetonitrile and water have 0.025% TFA.

Analytical HPLC-MS Method 4

Platform: Agilent 1100 series: equipped with an auto-sampler, an UV detector (220 nM and 254 nM), a MS detector (electrospray);

HPLC column: XTerra MS, $C_{18}$, 5μ, 3.0×250 mm column;

HPLC gradient: 1.0 mL/minute, from 10% acetonitrile in water to 90% acetonitrile in water in 46 minutes, jump to 99% acetonitrile and maintain 99% acetonitrile for 8.04 minutes. Both acetonitrile and water have 0.025% TFA.

HPLC Columns and Gradients

Analytical HPLC columns were BHK laboratories ODS/0/13 30×75 mm, 5 μm, 120 A; the standard gradient was 1 mL/min 10-90% $CH_3CN$ in water over 2 minutes, then 90% $CH_3CN$ for 1 minute. Constant percentage of 0.1% TFA was added.

Prep HPLC Column

YMC AQ, 5 μm, 120 A20, 20×50 mm cartridges

Chiral HPLC

Resolution of Racemic Mixtures through Column Chromatography: Typically the enantiomers were separated using preparative chiral HPLC (columns with an amylose carbamate adsorbent such as Chiralpak®AD and Chiralpak®AS, or a cellulose carbamate adsorbent such as Chiralcel®OD, or a cellulose ether adsorbent such as Chiralcel®OJ) using an isocratic gradient of the following solvents (or a combination thereof): hexanes, isopropyl alcohol, methanol, ethanol, acetonitrile and diethylamine.

Platform: Dionex P680A and P680P pumps, Dionex PAD 100 photodiode array detector, Jasco CD 2095 plus chiral detector, Gilson 215 liquid handler HPLC Columns: Chiral Technologies, Chiralpak AD-H (chiral profiles 1-8), Chiralcel OD-H (chiral profile 9). Analytical Columns are 0.46×25 cm, 5 μm; preparative columns are 2×25 cm, 5 μm.

Isocratic elutant: Flow Rate: 0.3 to 1.0 mL/min for analytical and 8 to 15 mL/min for preparative.

Elutant profile 1: Hexane/isopropyl alcohol 99/1 with 0.1% isopropylamine

Elutant profile 2: Hexane/isopropyl alcohol 97/3 with 0.1% isopropylamine

Elutant profile 3: Hexane/ethyl alcohol 97/3 with 0.1% diethylamine

Elutant profile 4: Hexane/isopropyl alcohol 95/5 with 0.1% diethylamine

Elutant profile 5: Hexane/isopropyl alcohol 85/15 with 0.1% diethylamine

Elutant profile 6: Hexane/ethyl alcohol 95/5 with 0.1% diethylamine

Elutant profile 7: Hexane/ethyl alcohol 9/1 with 0.1% diethylamine

Elutant profile 8: Hexane/isopropyl alcohol 9/1 with 0.1% diethylamine

Elutant profile 9: Methanol with 0.1% diethylamine.

Abbreviations

LDA: Lithium diisopropylamide
THF: Tetrahydrofuran
HPLC: High performance liquid chromatography
TFA: Trifluoroacetic acid
CHO: Chinese hamster ovary
EDCI: 1-(3-dimethylaminopropyl)-3-ethylcarbodiimide hydrochloride
DIEA: Diisopropylethylamine
DIPEA: N,N-Diisopropylethylamine
MsCl: Methanesulfonyl Chloride
LAH: Lithium aluminum hydride
TMEDA: Tetramethylethylenediamine
$t_R$: Retention time

Example 1A

SYNTHESIS OF REAGENT (2-BENZO[B]THIOPHEN-2-YL-ETHYL)-DIMETHYL-AMINE, ROUTE 1

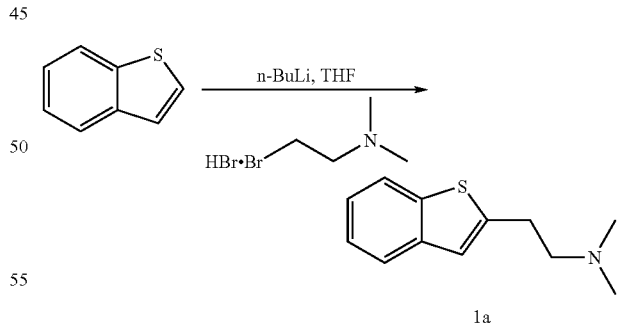

To a cooled (−78° C.) solution of benzothiophene (74.5 mmol) in anhydrous THF (100 mL) was added slowly n-BuLi (82 mmol, 1.6 M in hexanes). The mixture was stirred at −78° C. for 1 hr. β-Dimethylaminoethyl bromide hydrobromide (41 mmol) was added at −78° C. and the temperature was allowed to reach 0° C. over 5 hours. The mixture was quenched in sat. $NH_4Cl$, the pH of the aqueous layer was adjusted to 7-8 with sat. $NaHCO_3$, and the mixture was extracted with EtOAc (4×). The combined organic layers were concentrated and extracted with 1N HCl (3×). The combined HCl layers were made basic with sat. NaHCO₃, extracted with EtOAc (4×), and the combined organic layers were washed with brine, dried over MgSO₄, filtered and concentrated in vacuo to afford Compound 1a (2-Benzo[b]thiophen-2-yl-ethyl)-dimethyl-amine (4.96 g, 65%) as a tan solid; MS (MH⁺)=206.

Example 1B

SYNTHESIS OF REAGENT (2-BENZO[B]THIOPHEN-2-YL-ETHYL)-DIMETHYL-AMINE, ROUTE 2

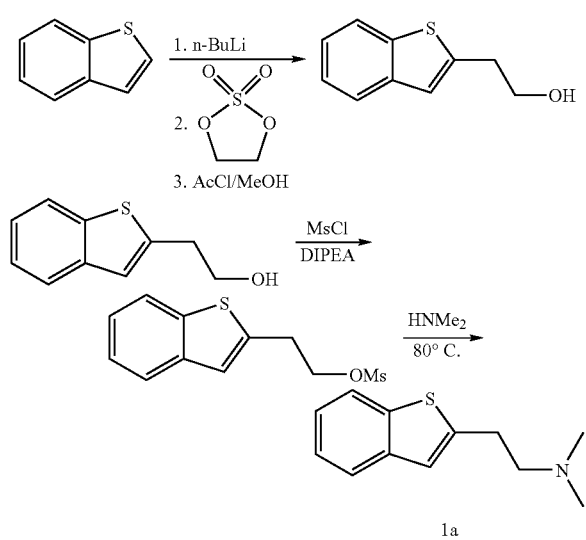

An alternative synthesis for compound 1a follows: Benzo[b]thiophene (20 g, 149 mmol) was dissolved in anhydrous THF (600 mL) and cooled to −50° C. N-BuLi (85 mL, 135 mmol, 1.6M in hexanes) was added and the mixture was stirred for 45 min at −40° C. A solution of [1,3,2]Dioxathiolane 2,2-dioxide (16.8 g, 135 mmol) in THF (100 mL) was added dropwise and the temperature was allowed to slowly reach room temperature, while being stirred overnight. Water and ether were added and the product was extracted with water. The combined water layers were concentrated in vacuo, MeOH and dichloromethane were added and the mixture was again concentrated in vacuo.

In a separate vessel AcCl (70 mL) was slowly added to cooled (0° C.) MeOH (700 mL) and stirred for 15 min. This mixture was cannulated to the residue obtained as described above and stirred for 4 hrs at room temperature. After concentration, EtOAc was added and the mixture was washed with sat. NaHCO₃ and brine, dried (Na₂SO₄), filtered and concentrated in vacuo to generate 19.1 g of 2-Benzo[b]thiophen-2-yl-ethanol as a white solid in 79% yield.

To a solution of 2-benzo[b]thiophen-2-yl-ethanol (16.8 mmol) in CH₂Cl₂ (60 mL) were added DIPEA (33.6 mmol) and mesylchloride (20.2 mmol.) The mixture was stirred for 18 hrs at RT, diluted with CH₂Cl₂, washed with sat. NaHCO₃ (3×), brine (1×), dried (MgSO₄) and concentrated in vacuo to give 4.3 g (99%) of methanesulfonic acid 2-benzo[b]thiophen-2-yl-ethyl ester which was used in the next step without further purification.

To methanesulfonic acid 2-benzo[b]thiophen-2-yl-ethyl ester (2.93 mmol) was added dimethylamine (30 mL, 2M in EtOH) and the mixture was heated in a sealed flask for 2 hrs at 80° C. Monitoring by TLC indicated complete conversion and the mixture was concentrated in vacuo. The residue was dissolved in EtOAc, washed with sat. NaHCO₃ (2×) and subsequently extracted with 1N HCl (3×). The combined HCl layers were made basic with sat. NaHCO₃, extracted with EtOAc (4×) and the combined organic layers were washed with brine, dried over MgSO₄, filtered and concentrated in vacuo to give Compound 1a (2-Benzo[b]thiophen-2-yl-ethyl)-dimethyl-amine (561 mg, 94%) as a tan solid; MS(MH⁺)=206.

In a similar procedure, using pyrrolidine in isopropanol 1-(2-Benzo[b]thiophen-2-yl-ethyl)-pyrrolidine was prepared. MH⁺=232

Example 2

SYNTHESIS OF REAGENT [2-(3-BROMO-BENZO[B]THIOPHEN-2-YL)-ETHYL]-DIMETHYL-AMINE

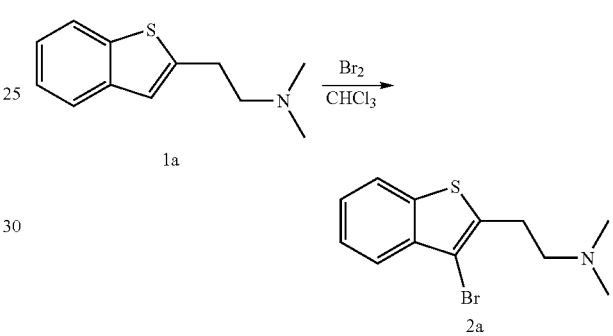

To a cooled solution of Compound 1a (2-Benzo[b]thiophen-2-yl-ethyl)-dimethyl-amine (39 mmol) in chloroform (500 mL) was added Br₂ (43 mmol) dropwise. The mixture was stirred overnight at RT and subsequently washed with sat. NaHCO₃ (3×) and brine, dried (MgSO₄) and concentrated in vacuo. The crude material was purified by silica gel column chromatography in EtOAc to afford [2-(3-Bromo-benzo[b]thiophen-2-yl)-ethyl]-dimethyl-amine, Compound 2a, as an oil (9.6 g, 86%); MS (MH⁺) 283.9.

In a similar procedure 1-[2-(3-Bromo-benzo[b]thiophen-2-yl)-ethyl]-pyrrolidine (MH⁺=311) was prepared in 96% yield, using the eluent EtOAc/hexanes=1/1 with gradient up to EtOAc/hexanes=4/1 for the silica gel column chromatography.

Example 3

SYNTHESIS OF (2-{3-[1-(4-FLUORO-PHENYL)-ETHYL]-BENZO[B]THIOPHEN-2-YL}-ETHYL)-DIMETHYL-AMINE

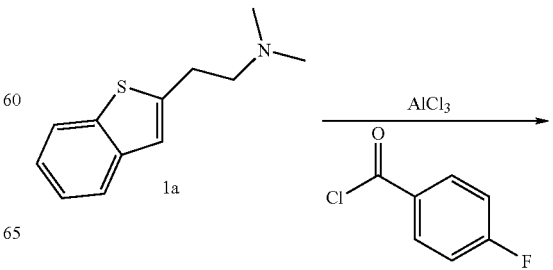

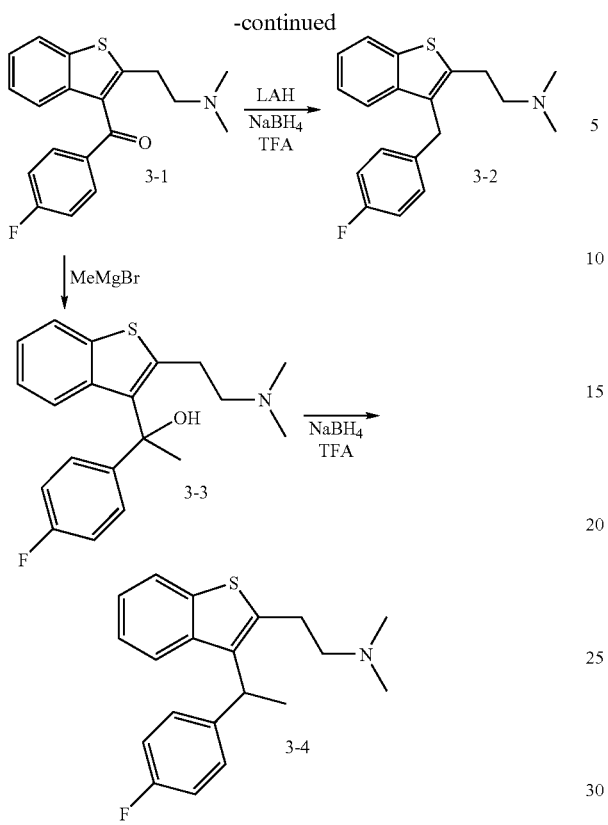

To a solution of (2-Benzo[b]thiophen-2-yl-ethyl)-dimethylamine (Compound 1a, 1.1 mmol) in dichloroethane (1 mL) under $N_2$ at 0° C., p-fluorobenzoyl chloride (1.32 mmol) and aluminum chloride (3.3 mmol, 1M in nitrobenzene) were added. The mixture was warmed to RT and stirred for 5 hrs, quenched in sat. $NaHCO_3$ and extracted with EtOAc (4×). The combined organic layers were washed with brine, dried ($MgSO_4$), filtered and concentrated in vacuo. The residue was purified by silica gel column chromatography in EtOAc with gradient to EtOAc:methanol (99:1) as required. Compound 3-1, [2-(2-Dimethylamino-ethyl)-benzo[b]thiophen-3-yl]-(4-fluoro-phenyl)-methanone, was isolated in 47% yield (170 mg); MS ($MH^+$)=327.8.

A 0° C. slurry of LAH (15 mg, 0.37 mmol) in THF (2 mL) was treated with a solution of Compound 3-1 (40 mg, 0.12 mmol) in THF (2 mL). The reaction was stirred at 0° C. for 2½ hrs for complete conversion as monitored by LC/MS. The reaction was quenched by the sequential addition of $H_2O$ (360 μL), NaOH (1N, 720 μL) and $H_2O$ (360 μL). The organic layer was separated and the aqueous layer extracted with EtOAc (3×). Combined organic layers were washed with brine, dried ($MgSO_4$) and concentrated in vacuo. The crude material was used in the next step without further purification. A suspension of $NaBH_4$ (18 mg, 0.48 mmol) in TFA (850 μL) was stirred for 15 min. A solution of the crude material from the previous step in TFA (500 μL) was added dropwise at RT. After stirring for 2 hrs at RT, the mixture was cooled, diluted with water and 1 N NaOH was added until pH 7-8. After extraction with EtOAc (3×), the combined organic layers were washed with brine, dried ($MgSO_4$) and concentrated in vacuo. The desired material was purified with preparative TLC (EtOAc/MeOH=9/1) to afford Compound 3-2, {2-[3-(4-Fluoro-benzyl)-benzo[b]thiophen-2-yl]-ethyl}-dimethyl-amine, in quantitative yield; MS ($MH^+$)=313.9.

To a cooled solution (−10° C.) of Compound 3-1 (0.12 mmol) in THF (1 mL), MeMgBr (0.2 mL, 3M in ether) was added dropwise. The mixture was stirred until complete conversion was accomplished as monitored by TLC, added to ice and extracted with EtOAc (3×). The combined organic layers were washed with brine, dried ($MgSO_4$), filtered and concentrated in vacuo. The material was purified by preparative TLC (EtOAc/MeOH=9/1) to afford Compound 3-3,1-[2-(2-Dimethylamino-ethyl)-benzo[b]thiophen-3-yl]-1-(4-fluoro-phenyl)-ethanol (26 mg, 72% yield); MS ($MH^+$) 343.9.

A suspension of $NaBH_4$ (0.29 mmol) in TFA (500 μL) was stirred for 15 min. A solution of Compound 3-3 (0.073 mmol) in $CH_2Cl_2$ (200 μL) was added dropwise at RT. After stirring for 2 hrs at RT, another portion of $NaBH_4$ (20 mg, 0.53 mmol) was added and stirring continued for 12 hrs. The mixture was cooled, diluted with water and 1 N NaOH was added until pH 7-8 obtained. The desired material was extracted with EtOAc (3×), the combined organic layers were washed with brine, dried ($MgSO_4$) and concentrated in vacuo. The concentrate was purified with preparative TLC (EtOAc/MeOH=9/1) to afford Compound 3-4, (2-{3-[1-(4-Fluoro-phenyl)-ethyl]-benzo[b]thiophen-2-yl}-ethyl)-dimethyl-amine (18 mg, 76% yield); MS ($MH^+$) 328.2.

The compounds of Table 1 were prepared according to the procedures described in Example 3:

TABLE 1

| No. | $R_1$ | $L_1$ | MW | $MH^+$ | $t_R$ (method) |
|-----|-------|-------|-----|--------|----------------|
| 3-1 | 4-fluorophenyl | —C(O)— | 327.4 | 327.8 | 1.62 (1) |
| 3-2 | 4-fluorophenyl | —$CH_2$— | 313.4 | 313.9 | 1.67 (1) |
| 3-3 | 4-fluorophenyl | —$CCH_3(OH)$— | 343.5 | 343.9 | 1.69 (1) |
| 3-4 | 4-fluorophenyl | —$CHCH_3$— | 327.5 | 328.2 | 6.54 (3) |
| 3-5 | phenyl | —C(O)— | 309.4 | 309.9 | 1.59 (1) |
| 3-6 | 4-chlorophenyl | —$CH_2$— | 329.9 | 329.8 | 1.73 (1) |

Example 4

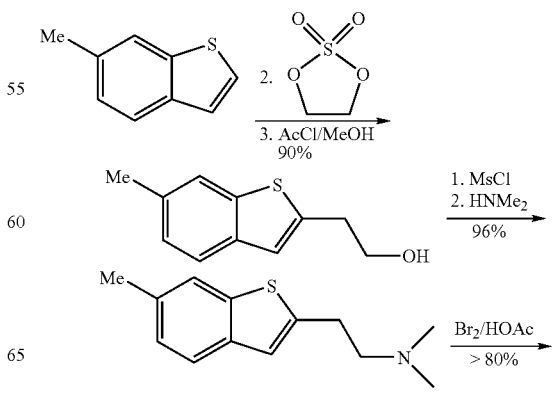

-continued

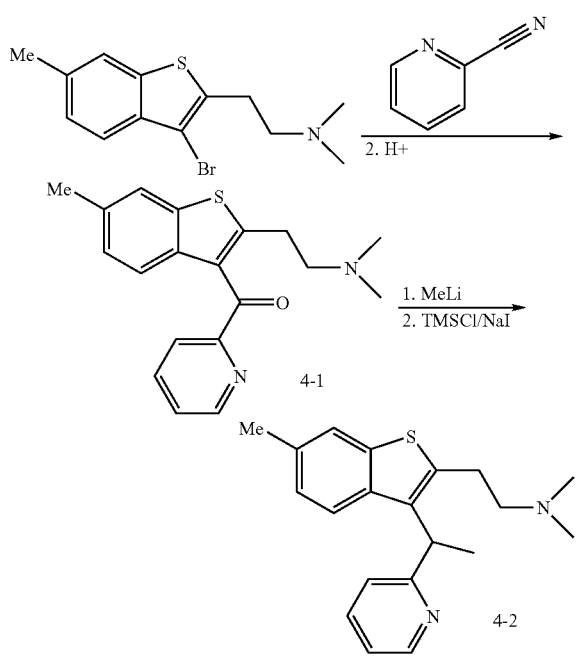

6-Methyl-benzo[b]thiophene was dissolved in anhydrous THF (75 mL) and cooled to −60° C. N-BuLi (11.4 mL, 18.2 mmol, 1.6M in hexanes) was added and the mixture was stirred for 45 min at −60° C. A solution of [1,3,2]Dioxathiolane 2,2-dioxide (2.26 g, 1.82 mmol) in THF (15 mL) was added dropwise and the temperature was allowed to slowly reach room temperature, while being stirred overnight. MeOH was added and the mixture was concentrated in vacuo.

In a separate vessel AcCl (15 mL) was slowly added to cooled (0° C.) MeOH (150 mL) and stirred for 15 min. This mixture was cannulated to the residue obtained as described above and stirred for 4 hrs at room temperature. After concentration, EtOAc was added and the mixture was washed with sat. NaHCO$_3$ and brine, dried (Na$_2$SO$_4$), filtered and concentrated in vacuo. Silica gel column chromatography (eluent: hexanes with gradient up to hexanes/EtOAc=4/1) afforded 2.83 g of 2-(6-methyl-benzo[b]thiophen-2-yl)-ethanol as a white solid in 89% yield.

To a cooled (0° C.) solution of 2-(6-methyl-benzo[b]thiophen-2-yl)-ethanol (3.22 g, 16.8) mmol) in dichloromethane (100 mL), methanesulfonylchloride (1.56 mL, 20.1 mmol) and DIEA (5.96 mL, 33.5 mmol) were added. The mixture was stirred for 15 min at 0° C. and then allowed to reach room temperature and stirred for an additional 2.5 hrs. It was washed with sat. NaHCO$_3$ (2×) and brine (1×), dried (Na$_2$SO$_4$), filtered and concentrated in vacuo. Methanesulfonic acid 2-(6-methyl-benzo[b]thiophen-2-yl)-ethyl ester was obtained as a solid and used without further purification.

In a closed pressure vessel methanesulfonic acid 2-(6-methyl-benzo[b]thiophen-2-yl)-ethyl ester from the previous step was taken up in MeOH (30 mL) and a 40% solution of dimethylamine in MeOH (30 mL) was added. The mixture was stirred for 2 hours at 90° C., cooled down to room temperature and concentrated in vacuo to afford 3.55 g of dimethyl-[2-(6-methyl-benzo[b]thiophen-2-yl)-ethyl]-amine (97%).

To a suspension of dimethyl-[2-(6-methyl-benzo[b]thiophen-2-yl)-ethyl]-amine (1.05 g, 4.78 mmol) in HOAc (5 mL) at 0° C., bromine was added slowly. The mixture was stirred overnight while it was allowed to slowly reach room temperature. MTBE (6 mL) was added and the solid was filtered, washed with MTBE and dried under vacuum. It was taken up in dichloromethane, washed with sat. NaHCO$_3$ and brine, dried (Na$_2$SO$_4$), filtered and concentrated in vacuo to give 1.1 g of [2-(3-bromo-6-methyl-benzo[b]thiophen-2-yl)-ethyl]-dimethyl-amine (77% yield).

[2-(3-Bromo-6-methyl-benzo[b]thiophen-2-yl)-ethyl]-dimethyl-amine (0.57 g, 1.91 mmol) was dissolved in 5 mL of anhydrous toluene. To the solution was added TMEDA (288 uL, 1.91 mmol) and the mixture was chilled to −78° C. To the mixture was carefully added sec-BuLi (1.6 mL, 2.04 mmol, 1.3M in cyclohexane) while keeping the internal temperature <−60° C. The mixture was stirred at −78° C. for 45 minutes. To the solution was added 2-cyanopyridine (184 mL, 1.91 mmol). The mixture was stirred at −78° C. for 40 minutes. The reaction was quenched by the careful dropwise addition of a mixture of 0.7 mL 6N HCl and 1.4 mL methanol. The mixture was allowed to warm to 0° C. and the organic phase was subsequently separated. The organic phase was extracted with 1N HCl. The combined aqueous phases were stirred at ambient temperature overnight. Following complete hydrolysis of the imine, the mixture was brought to pH 10 with the careful addition of 50% sodium hydroxide and extracted 3 times with ethyl acetate. The combined organic phases were dried over Na$_2$SO$_4$ and concentrated in vacuo. Silica gel chromatography (eluent: Dichloromethane/methanol=99/1 with gradient up to 92/8) generated 504 mg of [2-(2-Dimethylamino-ethyl)-6-methyl-benzo[b]thiophen-3-yl]-pyridin-2-yl-methanone (Compound 4-1) (81%).

To a cooled (−78° C.) solution of [2-(2-dimethylamino-ethyl)-6-methyl-benzo[b]thiophen-3-yl]-pyridin-2-yl-methanone (0.444 g, 1.50 mmol) in anhydrous toluene (5 mL), MeLi (1 mL, 1.6 mmol, 1.6 M in ether) was added and the mixture was stirred while the temperature was kept <−60° C. After 2 hours, an additional aliquot of MeLi (0.2 mL, 0.32 mmol) was added and stirring was continued for another 2 hours. The reaction was quenched with a mixture of 1.3 mL 6N HCl and 2.6 mL MeOH while keeping the temperature <−45° C. The mixture was allowed to warm to room temperature and the organic phase was separated. The organic phase was extracted with 500 mL of 1N HCl. The combined aqueous phases were neutralized with 50% sodium hydroxide and extracted 3 times with ethyl acetate. The combined organic phases were dried over Na$_2$SO$_4$, filtered and concentrated. Silica gel column chromatography (dichloromethane/MeOH=97/3 up to 85/15) afforded 1-[2-(2-dimethylamino-ethyl)-6-methyl-benzo[b]thiophen-3-yl]-1-pyridin-2-yl-ethanol in quantitative yield.

Sodium iodide (530 mg, 3.54 mmol) was taken up in acetonitrile and trimethylsilyl chloride (0.45 mL, 3.54 mmol) was added. After stirring for 5 min 1-[2-(2-dimethylamino-ethyl)-6-methyl-benzo[b]thiophen-3-yl]-1-pyridin-2-yl-ethanol (200 mg, 0.59 mmol) was added and the mixture was refluxed in a closed vessel for 6 hours. The reaction was cooled down to room temperature, diluted with EtOAc, washed with sat. NaHCO$_3$, Na$_2$S$_2$O$_3$ and brine respectively, dried (Na$_2$SO$_4$), filtered and concentrated in vacuo. A portion was purified by mass triggered preparative HPLC to generate dimethyl-{2-[6-methyl-3-(1-pyridin-2-yl-ethyl)-benzo[b]thiophen-2-yl]-ethyl}-amine (Compound 4-2). (MH$^+$=325.1, t$_R$=3.655, Method 2)

The enantiomers were separated using Chiral HPLC (Chiralpak AD-H column, eluent Hexanes: EtOH: diethylamine=95/5/0.1) to give dimethyl-{2-[6-methyl-3-((R)-1-pyridin-2-yl-ethyl)-benzo[b]thiophen-2-yl]-ethyl}-amine (Compound 4-3) (MH$^+$=325.0, $t_R$=3.269, Method 2) and dimethyl-{2-[6-methyl-3-((S)-1-pyridin-2-yl-ethyl)-benzo[b]thiophen-2-yl]-ethyl}-amine (Compound 4-4) (MH$^+$=325.0, $t_R$=3.211, Method 2).

To a cooled solution of 1-[2-(2-dimethylamino-ethyl)-6-methyl-benzo[b]thiophen-3-yl]-1-pyridin-2-yl-ethanol (Compound 4-5) (220 mg, 0.65 mmol) in TFA (2 mL), conc. sulfuric acid (500 uL) was added dropwise and the reaction was allowed to warm up to room temperature. After stirring for 4 hours the mixture was concentrated slightly, made basic with 1N NaOH and extracted with EtOAc (4 times). The combined organic layers were washed with brine, dried (Na$_2$SO$_4$), filtered and concentrated. Purification using mass triggered preparative HPLC afforded dimethyl-{2-[6-methyl-3-(1-pyridin-2-yl-vinyl)-benzo[b]thiophen-2-yl]-ethyl}-amine (Compound 4-6). (MH$^+$=323.0, $t_R$=40.15, Method 2)

Example 5

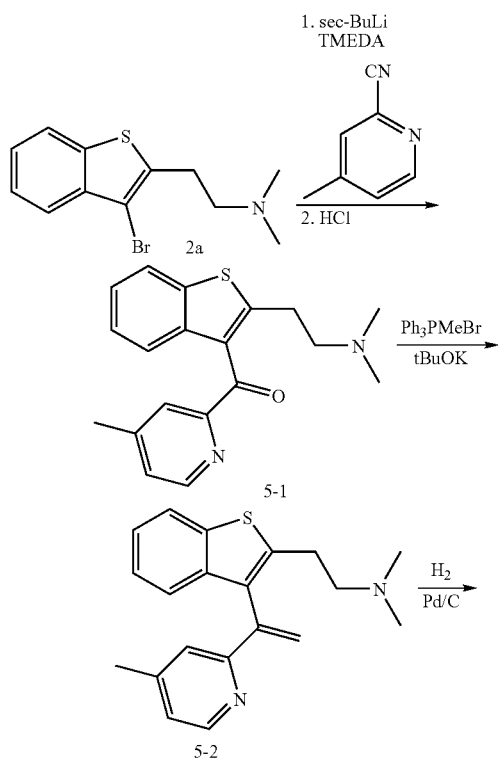

[2-(3-Bromo-benzo[b]thiophen-2-yl)-ethyl]-dimethyl-amine (0.36 g, 1.28 mmol) was dissolved in 3.5 mL of anhydrous toluene. To the solution was added TMEDA (192 uL, 1.28 mmol) and the mixture was chilled to –78° C. To the mixture was carefully added sec-BuLi (1.0 mL, 1.41 mmol, 1.4M in cyclohexane) while keeping the internal temperature <–60° C. The mixture was stirred at –78° C. for 30 minutes. To the solution was added 4-Methyl-pyridine-2-carbonitrile (150 mg, 1.28 mmol). The mixture was stirred at –78° C. for 30 minutes. The reaction was quenched by careful dropwise addition of a mixture of 1 mL 6N HCl and 2 mL methanol. The mixture was allowed to warm to 0° C. and the organic phase was subsequently separated. The organic phase was extracted with 1N HCl. The combined aqueous phases were stirred at ambient temperature overnight. Following complete hydrolysis of the imine, the mixture was brought to pH 10 with the careful addition of 50% sodium hydroxide and extracted 3 times with ethyl acetate. The combined organic phases were dried over Na$_2$SO$_4$ and concentrated in vacuo. Silica gel chromatography (eluent: dichloromethane/methanol=98/2 with 0.2% NH$_4$OH) generated 310 mg of [2-(2-Dimethylamino-ethyl)-benzo[b]thiophen-3-yl]-pyridin-2-yl-methanone (Compound 5-1) (78%).

Anhydrous THF (3 mL) was added to a mixture of potassium t-Butoxide (79 mg, 0.71 mmol) and methyltriphenylphosphonium bromide (0.25 g, 0.71 mmol) under N$_2$ atmosphere. The reaction was stirred for 30 min at room temperature. A solution of [2-(2-dimethylamino-ethyl)-benzo[b]thiophen-3-yl]-pyridin-2-yl-methanone (0.19 g, 0.59 mmol) in THF (2 mL) was added and the reaction was stirred at room temperature overnight. The THF was removed in vacuo, dichloromethane was added and the organic layer was washed with water, and concentrated in vacuo. Mass triggered preparative HPLC afforded 88 mg of dimethyl-(2-{3-[1-(4-methyl-pyridin-2-yl)-vinyl]-benzo[b]thiophen-2-yl}-ethyl)-amine (Compound 5-2) as a TFA salt.

The TFA salt of dimethyl-(2-{3-[1-(4-methyl-pyridin-2-yl)-vinyl]-benzo[b]thiophen-2-yl}-ethyl)-amine (88 mg, 0.2 mmol) was dissolved in EtOAc and DIEA (100 uL, 0.58 mmol) and palladium on carbon (10 mg, 10%) were added. The mixture was stirred under H$_2$ at 1 atm for 2 days, filtered over celite and purified by silica gel column chromatography (dichloromethane with 2% MeOH and 0.2% NH$_4$OH) to generate 58 mg of dimethyl-(2-{3-[1-(4-methyl-pyridin-2-yl)-ethyl]-benzo[b]thiophen-2-yl}-ethyl)-amine (Compound 5-3). (MH$^+$=325, $t_R$=2.96, Method 2)

The TFA salt of (2-{3-[1-(6-methoxy-pyridin-3-yl)-ethyl]-benzo[b]thiophen-2-yl}-ethyl)-dimethyl-amine (Compound 5-4) was made according to a similar procedure, but was purified by mass triggered preparative HPLC in the last step. (MH$^+$=341, $t_R$=4.72, Method 2)

Example 6

SYNTHESIS OF DIMETHYL-{2-[3-(1-PYRIDIN-2-YL-ETHYL)-BENZO[B]THIOPHEN-2-YL]-ETHYL}-AMINE

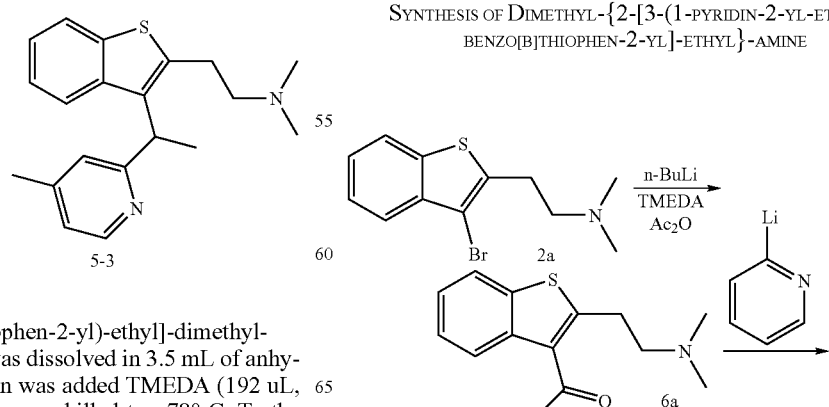

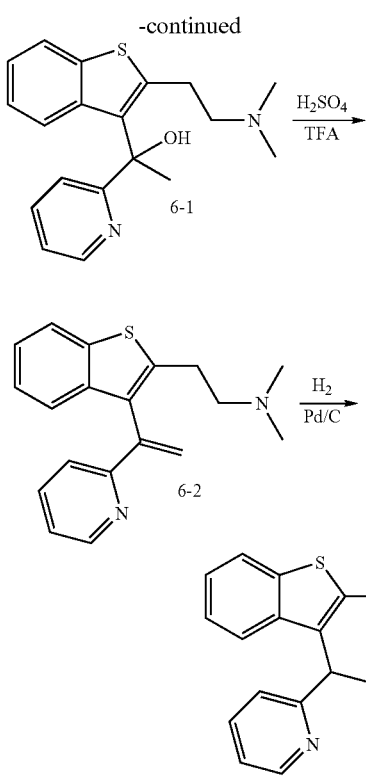

Compound 2a, [2-(3-bromo-benzo[b]thiophen-2-yl)-ethyl]-dimethyl-amine (17.5 mmol), was dissolved in anhydrous toluene (180 mL) and cooled to −78° C. Tetramethylethylenediamine (17.5 mmol) was added followed by n-BuLi (21.0 mmol, 1.6 M in hexanes). The mixture was stirred for 45 min at −78° C. Ac$_2$O (70 mmol) was added and the mixture was allowed to slowly reach RT and was stirred overnight. The mixture was quenched with sat. NH$_4$Cl, the pH of the aqueous layer was adjusted to 7-8 with sat. NaHCO$_3$, and the reaction mixture was extracted with EtOAc (4×). The combined organic layer was washed with brine, dried over MgSO$_4$, filtered and concentrated in vacuo. The crude material was purified by silica gel column chromatography in CH$_2$Cl$_2$ with a gradient up to CH$_2$Cl$_2$/MeOH=94/6 to afford Compound 6a, 1-[2-(2-dimethylamino-ethyl)-benzo[b]thiophen-3-yl]-ethanone (2.18 g, 50%); MS (MH$^+$)=248.1.

To a cooled solution (−78° C.) of 2-bromopyridine (17.8 mmol) in toluene (30 mL), n-BuLi (19.6 mmol, 1.6M in hexanes) was added dropwise. The mixture was stirred for 45 min. A solution of Compound 6a (4.45 mmol) in THF (15 mL) was added at −78° C. The mixture was slowly warmed to RT during a period of 16 hrs. The mixture was quenched in sat. NH$_4$Cl, the pH of the aqueous layer was adjusted to 7-8 with sat. NaHCO$_3$, and the mixture was extracted with EtOAc (4×.) The combined organic layer was washed with brine, dried over MgSO$_4$, filtered and concentrated in vacuo. The crude material was purified by silica gel column chromatography in EtOAc with a gradient up to EtOAc/MeOH=96/4 followed by a gradient of CH$_2$Cl$_2$/MeOH=95/5 up to CH$_2$Cl$_2$/MeOH=9/1 to afford Compound 6-1, 1-[2-(2-dimethylamino-ethyl)-benzo[b]thiophen-3-yl]-1-pyridin-2-yl-ethanol (0.35 g, 24%); MS (MH$^+$)=327.1.

Compound 6-1 (1.07 mmol) was dissolved in TFA (5 mL). Conc. H$_2$SO$_4$ (170 µL) was added in portions over 1.5 hrs. After stirring 1 additional hour at RT, the mixture was concentrated to a smaller volume in vacuo, neutralized with sat. NaHCO$_3$ and extracted with EtOAc (4×.) The combined organic layers were washed with brine, dried over MgSO$_4$, filtered and concentrated in vacuo. The crude material was purified by silica gel column chromatography in CH$_2$Cl$_2$ with a gradient up to CH$_2$Cl$_2$/MeOH=94/6 to afford Compound 6-2, dimethyl-{2-[3-(1-pyridin-2-yl-vinyl)-benzo[b]thiophen-2-yl]-ethyl}-amine (297 mg, 90%); MS (MH$^+$)= 309.1.

To a solution of Compound 6-2 (0.68 mmol) in MeOH (50 mL) was added a catalytic amount of palladium on activated carbon (10% Pd.) The mixture was stirred under atmospheric pressure of H$_2$ for 18 hrs, filtered over celite and concentrated in vacuo. The crude material was purified by silica gel column chromatography in CH$_2$Cl$_2$ with a gradient up to CH$_2$Cl$_2$/MeOH=94/6 to afford Compound 6-3, dimethyl-{2-[3-(1-pyridin-2-yl-ethyl)-benzo[b]thiophen-2-yl]-ethyl}-amine (140 mg, 66%); MS (MH$^+$)=311.1.

The compounds of Table 2 were prepared according to the procedures described in Example 6:

TABLE 2

| No. | R$_1$ | L$_1$ | MW | MH$^+$ | t$_R$ (method 2) |
|---|---|---|---|---|---|
| 6-1 | pyridin-2-yl | —C(OH)(CH$_3$)— | 326.5 | 327.1 | 3.389 |
| 6-2 | pyridin-2-yl | —C(=CH$_2$)— | 308.45 | 309.1 | 3.54 |
| 6-3 | pyridin-2-yl | —CH(CH$_3$)— | 310.46 | 311.1 | 1.653 |
| 6-4 | pyridin-3-yl | —C(=CH$_2$)— | 308.45 | 309.0 | 3.13 |
| 6-5 | pyridin-4-yl | —C(=CH$_2$)— | 308.45 | 309.0 | 2.90 |
| 6-6 | pyridin-3-yl | —CH(CH$_3$)— | 310.46 | 311.0 | 3.17 |
| 6-7 | pyridin-4-yl | —CH(CH$_3$)— | 310.46 | 310.9 | 2.67 |
| 6-8 | pyridin-3-yl | (R) —CH(CH$_3$)— | 310.46 | 310.8 | 2.965 |
| 6-9 | pyridin-3-yl | (S) —CH(CH$_3$)— | 310.46 | 310.8 | 2.93 |
| 6-10 | 3-methoxy-pyridin-2-yl | —CH(CH$_3$)— | 340 | 340.8 | 4.05 |
| 6-11 | 3-methoxy-pyridin-2-yl | (R) —CH(CH$_3$)— | 340 | 341.0 | 3.79 |
| 6-12 | 3-methoxy-pyridin-2-yl | (S) —CH(CH$_3$)— | 340 | 341.0 | 4.02 |

The enantiomers of Compound 6-10 (i.e., Compounds 6-11 and 6-12) were separated using chiral HPLC (column: chiralpak AD-H, eluent: Hexanes/iPrOH/diethylamine=95/5/0.1% diethylamine)

The enantiomers of compound 6-6 (i.e., Compounds 6-8 and 6-9) were separated using chiral HPLC (column: chiralpak AD-H, eluent hexanes/EtOH=85/15 with 0.1% diethylamine)

Example 7

Synthesis of (2-{3-[1-(5-Fluoro-pyridin-2-yl)-ethyl]-benzo[b]thiophen-2-yl}-ethyl)-dimethyl-amine

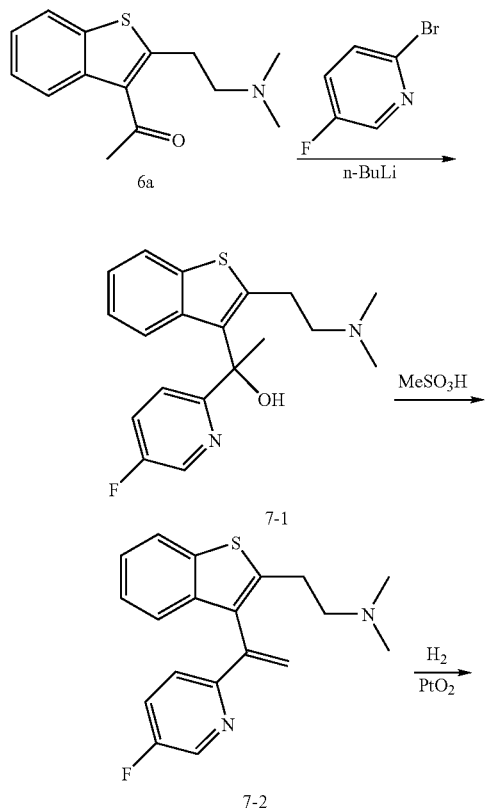

2-Bromo-5-fluoropyridine (5 g, 0.03 mol) was dissolved in methylene chloride (18 mL) and was cooled at −78° C. 1.6 M of n-butyllithium in hexane (18 mL) was added dropwise in 5 minutes and the reaction was stirred for 120 minutes at −78° C. Then a solution of 1-[2-(2-dimethylamino-ethyl)-benzo[b]thiophen-3-yl]-ethanone (1.75 g, 7.1 mmol) dissolved in methylene chloride (9 mL) and added dropwise and the mixture was allowed to warm to room temperature gradually overnight. The reaction was quenched with aq NH$_4$Cl, followed by water and ammonium hydroxide. The organic layer was extracted with Methylene chloride, and dried over sodium sulfate. Silica gel column chromatography (eluent: 9:1 DCM/MeOH) afforded 1.656 g of 1-[2-(2-dimethylamino-ethyl)-benzo[b]thiophen-3-yl]-1-(5-fluoro-pyridin-2-yl)-ethanol (Compound 7-1) (68%).

To a solution of 1-[2-(2-dimethylamino-ethyl)-benzo[b]thiophen-3-yl]-1-(5-fluoro-pyridin-2-yl)-ethanol in (1.65 g, 4.79 mmol) in methylene chloride (30 mL) at room temperature, methanesulfonic acid (310 uL, 4.8 mol) was added dropwise and the reaction was allowed to stir for 2 hours. Additional methanesulfonic acid (3.1 mL, 47.9 mmol) was added and the reaction was stirred for 2 more hours. The reaction was neutralized with aq NH$_4$OH and was extracted with methylene chloride. Organic layer was concentrated. The reaction mixture was chromatographed on silica gel with 9:1 DCM:MeOH as eluent to afford 923 mg of (2-{3-[1-(5-fluoro-pyridin-2-yl)-vinyl]-benzo[b]thiophen-2-yl}-ethyl)-dimethyl-amine (Compound 7-2) (59%).

To a solution of (2-{3-[1-(5-fluoro-pyridin-2-yl)-vinyl]-benzo[b]thiophen-2-yl}-ethyl)-dimethyl-amine (133 mg, 0.407 mmol) in ethanol (7 mL), platinum dioxide (50 mg, 0.2 mmol) was added. Reaction was shaken at 35 psi for 3 hours and at 40 psi for 3 hours under an atmosphere of hydrogen. The reaction mixture was filtered and washed with EtOH. Purification by mass triggered preparative HPLC afforded (2-{3-[1-(5-fluoro-pyridin-2-yl)-ethyl]-benzo[b]thiophen-2-yl}-ethyl)-dimethyl-amine (Compound 7-3). (MH$^+$=329, t$_R$=40.592, Method 2) The enantiomers (2-{3-[(R)-1-(5-fluoro-pyridin-2-yl)-ethyl]-benzo[b]thiophen-2-yl}-ethyl)-dimethyl-amine (Compound 7-4) (MH$^+$=329.0, t$_R$=4.617, Method 2) and (2-{3-[(S)-1-(5-fluoro-pyridin-2-yl)-ethyl]-benzo[b]thiophen-2-yl}-ethyl)-dimethyl-amine (Compound 7-5) (MH$^+$=329.0, t$_R$=4.554, Method 2) were separated using a chiral HPLC OJ-H column, Eluent: Hexanes:EtOH=90:10 with 0.1% DEA.

Example 8

Synthesis of Dimethyl-{2-[3-(1-thiazol-2-yl-ethyl)-benzo[b]thiophen-2-yl]-ethyl}-amine

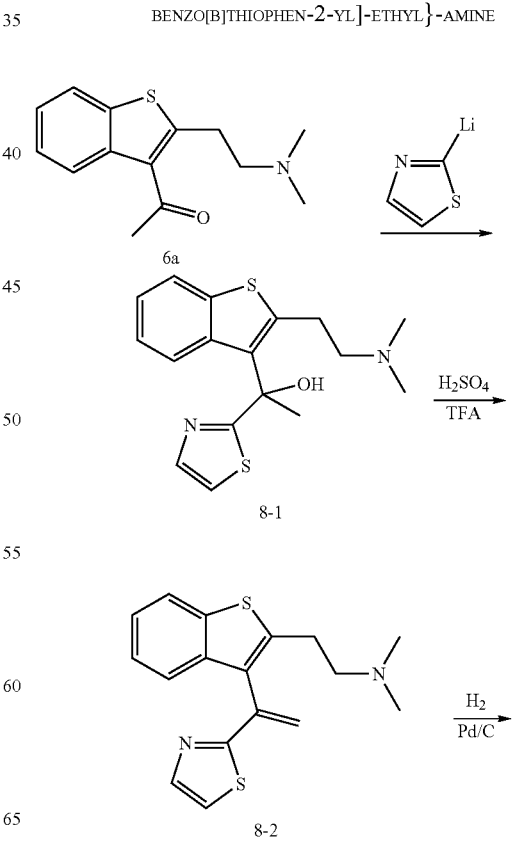

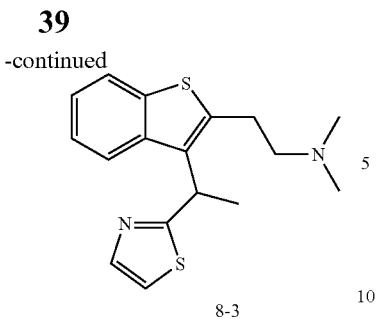

8-3

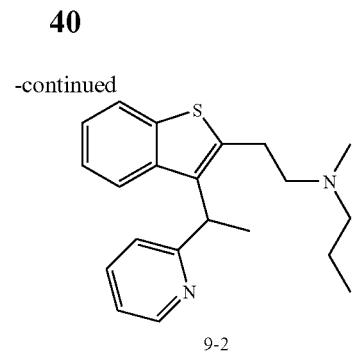

9-2

To a cooled solution (−78° C.) of thiazole (1.1 mmol) in THF (3 mL) was added n-BuLi (3.3 mmol, 1.6 M in hexanes) dropwise. The mixture was stirred for 30 min. A solution of ethanone Compound 6a (0.36 mmol) in THF (1.5 mL) was added at −78° C. The mixture was slowly warmed to 0° C. during a period of 5 hrs. The mixture was quenched with sat. NH$_4$Cl, the pH of the aqueous layer was adjusted to 7-8 with sat. NaHCO$_3$, and the mixture was extracted with EtOAc (4×.) The combined organic layer was washed with brine, dried over MgSO$_4$, filtered and concentrated in vacuo. The crude material was purified by silica gel column chromatography in CH$_2$Cl$_2$ followed by a gradient up to CH$_2$Cl$_2$/MeOH=98/2 to afford Compound 8-1, 1-[2-(2-dimethylamino-ethyl)-benzo[b]thiophen-3-yl]-1-thiazol-2-yl-ethanol (66 mg, 55%); MS(MH$^+$)=333.1.

Compound 8-2, dimethyl-{2-[3-(1-thiazol-2-yl-vinyl)-benzo[b]thiophen-2-yl]-ethyl}-amine, was prepared from Compound 8-1 as described in Step 6; MS (MH$^+$)=315.0

Compound 8-3, dimethyl-{2-[3-(1-thiazol-2-yl-ethyl)-benzo[b]thiophen-2-yl]-ethyl}-amine was prepared from Compound 8-2 by catalytic hydrogenation as described for Compound 6-3 in above Step 6. The desired compound was purified by mass triggered HPLC purification as a TFA salt (6 mg); MS(MH$^+$)=317.2.

Example 9

SYNTHESIS OF METHYL-PROPYL-{2-[3-(1-PYRIDIN-2-YL-ETHYL)-BENZO[B]THIOPHEN-2-YL]-ETHYL}-AMINE

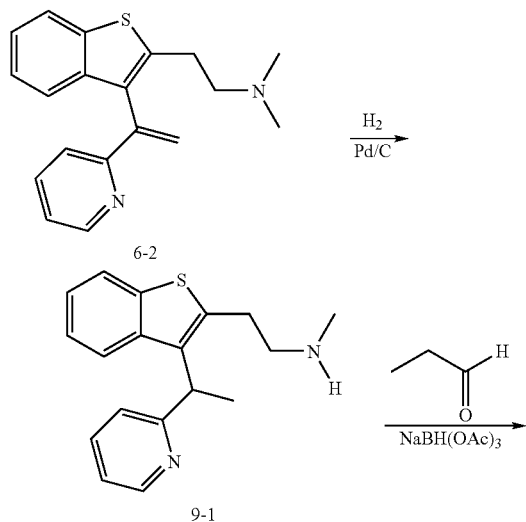

A catalytic amount of Pd on activated carbon (10% Pd) was added to a solution of Compound 6-2 (0.13 mmol) in MeOH (20 mL.) The mixture was stirred under atmospheric pressure of H$_2$ for 48 hrs. After filtration over Celite®, the mixture was concentrated in vacuo and purified by preparative TLC using CH$_2$Cl$_2$/MeOH=9:1 as eluent to afford 7 mg of Compound 9-1, methyl-{2-[3-(1-pyridin-2-yl-ethyl)-benzo[b]thiophen-2-yl]-ethyl}-amine; (MH$^+$=296.9, t$_R$=1.675, Method 1).

To a solution of Compound 9-1 (0.02 mmol) in DMA (300 μL) were added HOAc (3 μL), sodium triacetoxyborohydride (0.03 mmol) and propionaldehyde (0.097 mmol.) The mixture was stirred overnight, diluted with 100 μL DMSO and 100 μL MeOH and purified by preparative mass triggered HPLC to afford Compound 9-2, methyl-propyl-{2-[3-(1-pyridin-2-yl-ethyl)-benzo[b]thiophen-2-yl]-ethyl}-amine (4.3 mg); (MH$^+$=339.1, t$_R$=3.692, Method 2)

Example 10

SYNTHESIS OF DIMETHYL-(2-{3-[1-(6-METHYL-PYRIDIN-3-YL)-ETHYL]-BENZO[B]THIOPHEN-2-YL}-ETHYL)-AMINE

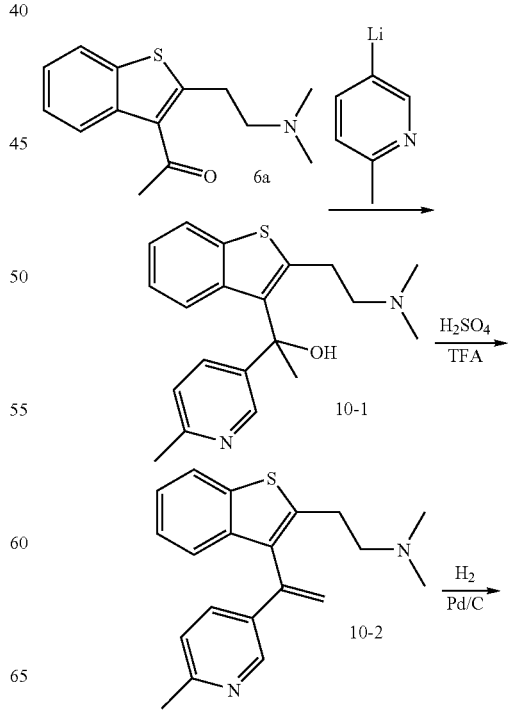

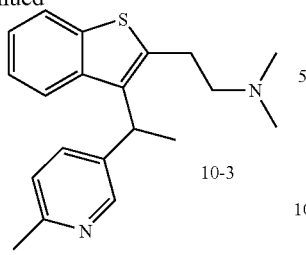

To a cooled solution (−100° C.) of 2-methyl-5-bromopyridine (4.8 mmol) in THF (10 mL) was added n-BuLi (3 mL, 4.8 mmol, 1.6M in hexanes) dropwise. The mixture was allowed to warm up to −78° C. and stirred for 10 minutes at this temperature. A solution of Compound 6a (1.2 mmol) in THF (3 mL) was then added and the mixture was slowly warmed to RT during a period of 16 hrs. The mixture was quenched in sat. NH$_4$Cl, the pH of the aqueous layer was adjusted to 7-8 with sat. NaHCO$_3$ and the mixture was extracted with EtOAc (3×.) The combined organic layers were washed with brine, dried over MgSO$_4$, filtered and concentrated in vacuo. The crude material was purified by silica gel column chromatography in CH$_2$Cl$_2$ with a gradient of CH$_2$Cl$_2$/MeOH=95/5 up to CH$_2$Cl$_2$/MeOH=90/10 to yield Compound 10-1, 1-[2-(2-dimethylamino-ethyl)-benzo[b]thiophen-3-yl]-1-(6-methyl-pyridin-3-yl)-ethanol (0.29 g, 71%); MS(MH$^+$)=341.

Compound 10-1 (0.59 mmol) was dissolved in TFA (2.5 mL). Conc. H$_2$SO$_4$ (55 µL) was added. After 1 hour of stirring at RT the mixture was concentrated to a smaller volume in vacuo, neutralized with sat. NaHCO$_3$ and extracted with EtOAc (3×.) The combined organic layers were washed with brine, dried over MgSO$_4$, filtered and concentrated in vacuo. The crude material was purified by silica gel column chromatography in CH$_2$Cl$_2$ with CH$_2$Cl$_2$/MeOH=95/5 to yield Compound 10-1, dimethyl-(2-{3-[1-(6-methyl-pyridin-3-yl)-vinyl]-benzo[b]thiophen-2-yl}-ethyl)-amine (0.1 g, 52%); (MH$^+$=323, $t_R$=30.52, Method 2).

To a solution of Compound 10-2 (90 mg, 0.28 mmol) in MeOH (5 mL) was added a catalytic amount (50 mg) of Palladium on activated carbon (10% Pd.) The mixture was stirred under atmospheric pressure of H$_2$ for 3 hrs, then four other portions of Pd/C were successively added with stirring under atmospheric pressure of H$_2$ for 2 hrs each time. The reaction was then filtered over celite and concentrated in vacuo. The crude material was purified by silica gel column chromatography in CH$_2$Cl$_2$ with a gradient from CH$_2$Cl$_2$/MeOH=95/5 up to CH$_2$Cl$_2$/MeOH=90/10 to yield Compound 10-3, dimethyl-(2-{3-[1-(6-methyl-pyridin-3-yl)-ethyl]-benzo[b]thiophen-2-yl}-ethyl)-amine (38 mg, 43%); (MH$^+$=325, $t_R$=3.35, Method 2)

Example 11

Synthesis of Dimethyl-{2-[3-(1-pyrazin-2-yl-ethyl)-benzo[b]thiophen-2-yl]-ethyl}-amine

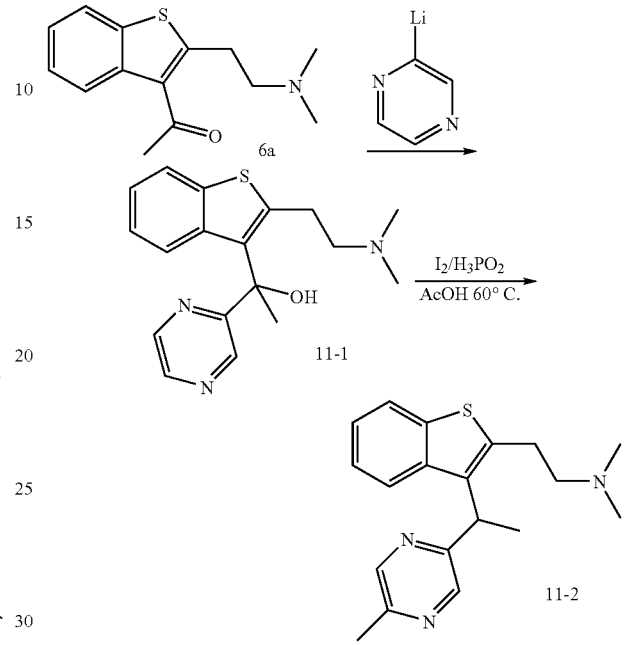

To a cooled solution (−78° C.) of iodopyrazine (4.8 mmol) in diethyl ether (10 mL) n-BuLi (3 mL, 4.8 mmol, 1.6M in hexanes) was added dropwise. The mixture was stirred at −78° C. for 2 hr. A solution of Compound 6a (1.2 mmol) in diethyl ether (3 mL) was added and the mixture was slowly warmed to RT during a period of 16 hrs. The mixture was quenched in sat. NH$_4$Cl, the pH of the aqueous layer was adjusted to 7-8 with sat. NaHCO$_3$ and the mixture was extracted with EtOAc (3×.) The combined organic layers were washed with brine, dried over MgSO$_4$, filtered and concentrated in vacuo. The crude material was purified by silica gel column chromatography in CH$_2$Cl$_2$ with a gradient of CH$_2$Cl$_2$/MeOH=95/5 up to CH$_2$Cl$_2$/MeOH=94/6 to afford Compound 11-1,1-[2-(2-Dimethylamino-ethyl)-benzo[b]thiophen-3-yl]-1-pyrazin-2-yl-ethanol (0.15 g, 38%); MS(MH$^+$)=328.0

Compound 11-1 (0.15 mmol) and iodine (1 eq.) were dissolved in acetic acid (1 mL). H$_3$PO$_2$ (75 µL of a 50% wt solution in water, 4.5 eq) was added at RT and the mixture was heated to reflux for 4 hr. The mixture was allowed to cool to RT and Na$_2$S$_2$O$_5$ solution was added. The pH of the aqueous layer of the mixture was adjusted to 7-8 with sat. NaHCO$_3$ and the mixture was extracted with EtOAc (3×). The combined organic layers were washed with brine, dried over MgSO$_4$, filtered and concentrated in vacuo. The crude material was purified by silica gel column chromatography in CH$_2$Cl$_2$ with CH$_2$Cl$_2$/MeOH=95/5 to afford Compound 11-2, dimethyl-{2-[3-(1-pyrazin-2-yl-ethyl)-benzo[b]thiophen-2-yl]-ethyl}-amine (13 mg, 27%); (MH$^+$=312.0, $t_R$=4.44, Method 2). The enantiomers were separated using chiral HPLC (Chiralpak AD-H, eluent: hexanes/EtOH=85/15) to give dimethyl-{2-[3-((R)-1-pyrazin-2-yl-ethyl)-benzo[b]thiophen-2-yl]-ethyl}-amine MH$^+$=312.0 (Compound 11-3)

(MH+=312.0, $t_R$=40.11, Method 2) and dimethyl-{2-[3-((S)-1-pyrazin-2-yl-ethyl)-benzo[b]thiophen-2-yl]-ethyl}-amine MH+=312.0 (Compound 11-4) (MH+=312.0, $t_R$=4.10, Method 2).

Example 12

CHIRAL RESOLUTION OF DIMETHYL-{2-[3-(1-PYRIDIN-2-YL-ETHYL)-BENZO[B]THIOPHEN-2-YL]-ETHYL}-AMINE

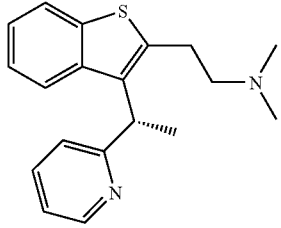

12-1

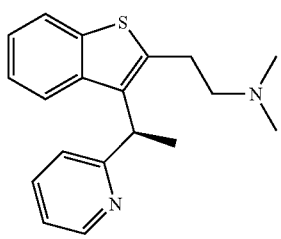

12-2

To a solution of racemic Compound 6-3 (4 mmol) in absolute EtOH (12 mL) was added a solution of D-tartaric acid (4.06 mmol). The mixture was allowed to stand at room temperature for 48 hrs. The crystalline material which formed was filtered off and washed with ether (>98% ee, $t_R$=9.78 min, [α]$_D$+82.3°, c=0.01, MeOH). The enantiomeric excess was determined using chiral HPLC (Chiralcel OD-H, 0.5 ml/min, hexane:EtOH=95:5 with 0.1% diethylamine.) By crystal structure analysis this was determined to be (S)-(+)-dimethyl-{2-[3-(1-pyridin-2-yl-ethyl)-benzo[b]thiophen-2-yl]-ethyl}-amine (Compound 12-1). The combined filtrates were concentrated in vacuo, dissolved in EtOAc, washed with saturated NaHCO₃ and brine, dried (MgSO₄) and concentrated in vacuo. The oily residue (1.84 mmol) was dissolved in absolute EtOH (6 mL) and a solution of L-tartaric acid (1.87 mmol) in EtOH (3 mL) was added. The mixture was allowed to stand at room temperature for 48 hrs. The crystalline material which formed was filtered off, washed with ether and subsequently lyophilized to afford (R)-(-)-dimethyl-{2-[3-(1-pyridin-2-yl-ethyl)-benzo[b]thiophen-2-yl]-ethyl}-amine (Compound 12-2) (655 mg, 96% ee, $t_R$=10.3 min using column conditions as described above, [α]$_D$-124° (c=0.01, MeOH).

Example 13

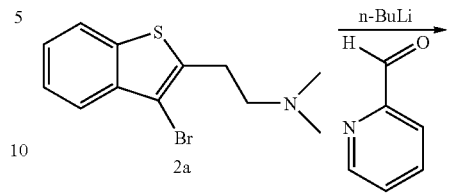

2a

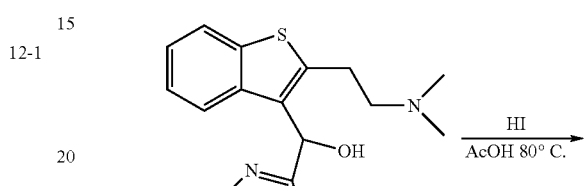

13-1

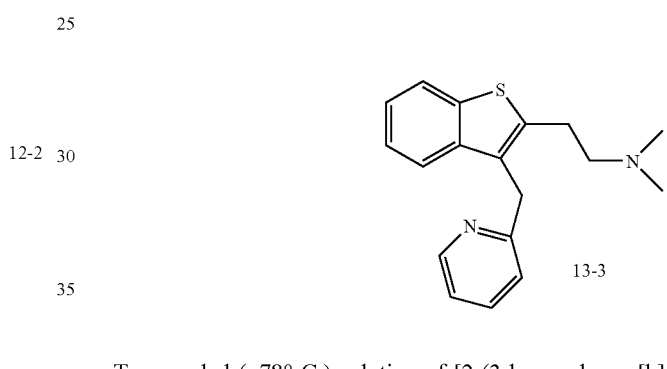

13-3

To a cooled (-78° C.) solution of [2-(3-bromo-benzo[b]thiophen-2-yl)-ethyl]-dimethyl-amine (800 mg, 2.8 mmol) in anhydrous toluene (30 mL), TMEDA (420 uL, 2.8 mmol) was added followed by nBuLi (2.1 mL, 2.6 mmol, 1.6M in hexanes). The mixture was stirred for 40 min at -78° C. and pyridine-2-carbaldehyde (800 uL, 8.4 mmol) was added. The mixture was stirred for 6 hrs during which the temperature reached 0° C., quenched with sat NH₄Cl/NaHCO₃ and extracted with EtOAc (3×). The combined organic layers were dried (Na₂SO₄), concentrated and purified by silical gel column chromatography (gradient of DCM/MeOH=98/2 up to 94/6) to afford [2-(2-dimethylamino-ethyl)-benzo[b]thiophen-3-yl]-pyridin-2-yl-methanol (Compound 13-1) (721 mg) in 82% yield. MH+=313.0, $t_R$=2.49 min (Method 2).

In a similar procedure [2-(2-dimethylamino-ethyl)-benzo[b]thiophen-3-yl]-pyrimidin-5-yl-methanol (Compound 13-2) was prepared. MH+=314.0, $t_R$=3.2 min (Method 2).

[2-(2-Dimethylamino-ethyl)-benzo[b]thiophen-3-yl]-pyridin-2-yl-methanol (12 mg, 0.038 mmol) was dissolved in HOAc (100 mL) and HI (100 uL). After stirring for 2 hours at room temperature the mixture was heated at 80° C. for 16 hrs. The mixture was concentrated in vacuo, diluted with EtOAc, washed with 1M Na₂S₂O₃ and sat NaHCO₃, brine, dried (Na₂SO₄), filtered and concentrated in vacuo to generate dimethyl-[2-(3-pyridin-2-ylmethyl-benzo[b]thiophen-2-yl)-ethyl]-amine (Compound 13-3) in quantitative yield as a solid.

The compounds of Table 3 were prepared according to the procedures described in Example 13:

TABLE 3

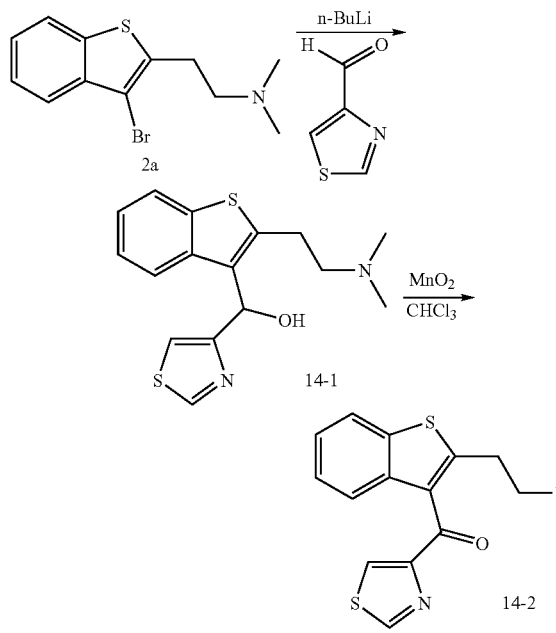

| No. | R | MW | MH+ | $t_R$ (Method 2) |
|---|---|---|---|---|
| 13-3 | pyridin-2-yl | 296.4 | 297 | 2.67 |
| 13-4 | pyrimidin-5-yl | 297.4 | 298.0 | 3.82 |
| 13-5 | thiazol-2-yl | 302.5 | 302.9 | 4.06 |
| 13-6 | thiazol-4-yl | 302.5 | 302.9 | 4.09 |
| 13-7 | 3-methoxy-pyridin-2-yl | 326.5 | 327.0 | 3.57 |
| 13-8 | 6-hydroxy-pyridin-2-yl | 312.4 | 313.0 | 3.46 |
| 13-9 | pyrazin-2-yl | 297.4 | 297.8 | 3.58 |
| 13-10 | furan-2-yl | 285.4 | 285.8 | 3.74 |
| 13-11 | 3-methyl-3H-imidazol-4-yl | 299.4 | 299.8 | 2.42 |
| 13-12 | [1,2,3]thiadiazol-5-yl | 303.4 | 303.8 | 3.95 |
| 13-13 | 2,5-dimethyl-2H-pyrazol-3-yl | 313.5 | 313.8 | 3.89 |
| 13-14 | 4-chloro-1-methyl-1H-pyrazol-3-yl | 333.9 | 333.0 | 4.82 |
| 13-15 | 1-methyl-1H-imidazol-2-yl | 299.4 | 299.8 | 1.71 |

Example 14

To a cooled (−78° C.) solution of [2-(3-bromo-benzo[b]thiophen-2-yl)-ethyl]-dimethyl-amine (200 mg, 0.7 mmol) in anhydrous toluene (8 mL), TMEDA (110 uL, 0.7 mmol) was added followed by nBuLi (0.47 mL, 0.75 mmol, 1.6M in hexanes). The mixture was stirred for 40 min at −78° C. and a solution of thiazole-4-carbaldehyde (0.32 g, 2.8 mmol) in dichloromethane (1 mL) was added. The mixture was stirred for 16 hrs during which the temperature reached room temperature. The reaction was quenched with water, the resulting mixture was basified by the addition of NH₄OH and extracted with EtOAc. The combined organic layers were concentrated and subjected to mass triggered preparative HPLC to afford [2-(2-dimethylamino-ethyl)-benzo[b]thiophen-3-yl]-thiazol-4-yl-methanol (Compound 14-1) (200 mg). MH+=318.8.

[2-(2-Dimethylamino-ethyl)-benzo[b]thiophen-3-yl]-thiazol-4-yl-methanol (200 mg, 0.42 mmol) was dissolved in CHCl₃ (10 mL) and MnO₂ (0.54 g, 3.1 mmol) was added. The reaction mixture was stirred overnight, filtered over celite and washed with dichloromethane and MeOH. Purification by preparative HPLC afforded [2-(2-dimethylamino-ethyl)-benzo[b]thiophen-3-yl]-thiazol-4-yl-methanone (Compound 14-2) (113 mg) as a TFA salt. MH+=316.7

In a similar procedure [2-(2-Pyrrolidin-1-yl-ethyl)-benzo[b]thiophen-3-yl]-thiazol-4-yl-methanone (Compound 14-3) was prepared from 1-[2-(3-bromo-benzo[b]thiophen-2-yl)-ethyl]-pyrrolidine in 63% overall yield.

The compounds of Table 4 were prepared according to the procedures described in Example 14:

TABLE 4

| No | Hetaryl | MW | MH+ | $t_R$ (Method 1) |
|---|---|---|---|---|
| 14-4 | thiazol-5-yl | 316.1 | 317.0 | 2.03 |
| 14-5 | 2-methoxy-pyridin-3-yl | 340.1 | 341.0 | 2.14 |
| 14-6 | 2-fluoro-pyridin-3-yl | 328.1 | 329.0 | 2.07 |
| 14-7 | 2-methoxy-pyridin-6-yl | 340.1 | 341.0 | 2.23 |
| 14-8 | 2-fluoro-pyridin-6-yl | 328.1 | 329.0 | 2.14 |
| 14-9 | 4-methoxy-pyridin-3-yl | 340.1 | 341.0 | 1.80 |
| 14-10 | 3-fluoro-pyridin-2-yl | 328.1 | 329.0 | 2.03 |

Example 15

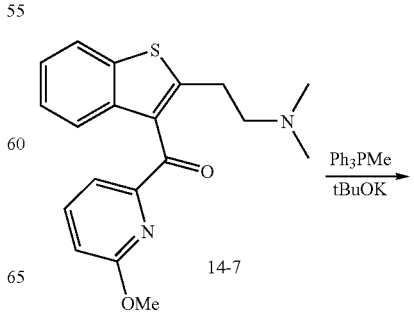

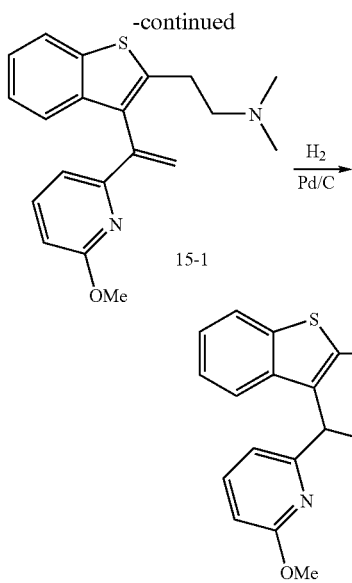

Anhydrous THF (8 mL) was added to a mixture of potassium t-butoxide (140 mg, 1.27 mmol) and methyltriphenylphosphonium bromide (0.45 g, 1.27 mmol) under $N_2$ atmosphere. The reaction was stirred for 30 min at room temperature. A solution of [2-(2-dimethylamino-ethyl)-benzo[b]thiophen-3-yl]-(6-methoxy-pyridin-2-yl)-methanone (0.29 g, 0.85 mmol) in THF (8 mL) was added and the reaction was stirred for 1 hour at room temperature. The reaction was quenched by the addition of 0.1N HCl until the pH was <3 and extracted with 0.1N HCl. The aqueous layers were made basic with $NH_4OH$ and extracted with EtOAc. The organic layers were washed with water and concentrated in vacuo. Mass triggered preparative HPLC afforded 190 mg of (2-{3-[1-(6-methoxy-pyridin-2-yl)-vinyl]-benzo[b]thiophen-2-yl}-ethyl)-dimethyl-amine (Compound 15-1) as a TFA salt.

The TFA salt of (2-{3-[1-(6-methoxy-pyridin-2-yl)-vinyl]-benzo[b]thiophen-2-yl}-ethyl)-dimethyl-amine (190 mg, mmol) was dissolved in MeOH (12 mL) and a catalytic amount of 10% Pd/C was added. The reaction was stirred under 1 Atm of $H_2$ for 2.5 hours, filtered over celite, washed with dichloromethane, concentrated in vacuo and purified by mass triggered preparative HPLC to give (2-{3-[1-(6-methoxy-pyridin-2-yl)-ethyl]-benzo[b]thiophen-2-yl}-ethyl)-dimethyl-amine (Compound 15-2). $MH^+=341.0$, $t_R=5.2$ min.

The compounds of Table 5 were prepared according to the procedures described in Example 15:

TABLE 5

| No | $R_1$ | $R_2$ | MW | $MH^+$ | $t_R$ (Method) |
|---|---|---|---|---|---|
| 15-2 | 6-methoxy-pyridin-2-yl | Me | 340.5 | 341.0 | 5.2 (2) |
| 15-3 | 6-fluoro-pyridin-2-yl | Me | 328.4 | 329.0 | 4.99 (2) |
| 15-4 | 2-methoxy-pyridin-3-yl | Me | 340.5 | 341.1 | 17.4 (4) |
| 15-5 | 2-methoxy-pyridin-3-yl | (R)Me | 340.5 | 341.0 | 4.94 (2) |
| 15-6 | 2-methoxy-pyridin-3-yl | (S)Me | 340.5 | 341.0 | 4.92 (2) |
| 15-7 | 2-fluoro-pyridin-3-yl | Me | 328.4 | 329.0 | 4.63 (2) |
| 15-8 | 2-fluoro-pyridin-3-yl | (R)Me | 328.4 | 329.0 | 4.65 (2) |
| 15-9 | 2-fluoro-pyridin-3-yl | (S)Me | 328.4 | 329.0 | 4.70 (2) |

The enantiomers of Compound 15-3 (i.e., Compound 15-4 and 15-5) were separated using chiral HPLC (Chiralpak OD-H, eluent: hexanes/iPrOH/diethylamine=99/1/0.1).

The enantiomers of Compound 15-6 (i.e., Compound 15-7 and 15-8) were separated using chiral HPLC (Chiralpak AD-H, eluent: hexanes/EtOH/diethylamine=95/5/0.1).

Example 16

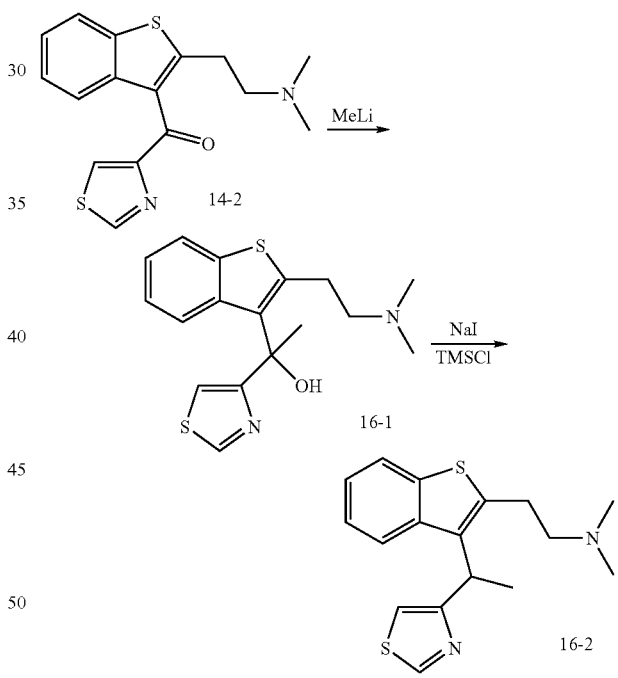

[2-(2-Dimethylamino-ethyl)-benzo[b]thiophen-3-yl]-thiazol-4-yl-methanone (Compound 14-2) (0.11 g, 0.35 mmol) was dissolved in THF (2 mL) and cooled to −78° C. MeLi (4.3 mL, 1.6 M, 7 mmol) was added slowly and the reaction was stirred at −78° C. for 2 hrs. The reaction was quenched with water and $NH_4OH$ was added until pH was ~9 and extracted with EtOAc, dried ($Na_2SO_4$), filtered and concentrated in vacuo. The crude material was purified by preparative HPLC, generating 13 mg of 1-[2-(2-dimethylamino-ethyl)-benzo[b]thiophen-3-yl]-1-thiazol-4-yl-ethanol (Compound 16-1). $MH^+=316.8$, $t_R=4.44$ (Method 2).

To a solution of NaI (34 mg, 0.22 mmol) in ACN (0.3 mL) TMSCl (29 uL, 0.23 mmol) was added. After stirring for 5 min, a solution of 1-[2-(2-dimethylamino-ethyl)-benzo[b]thiophen-3-yl]-1-thiazol-4-yl-ethanol (13 mg, 0.04 mmol) in acetonitrile (0.3 mL) was added and the mixture was refluxed in a closed vessel for 2 hrs. The mixture was quenched with water and NH$_4$OH was added until the pH was ~9, the mixture was subsequently extracted with EtOAc. The combined organic layers were concentrated in vacuo and subjected to preparative HPLC to generate 5 mg of dimethyl-{2-[3-(1-thiazol-4-yl-ethyl)-benzo[b]thiophen-2-yl]-ethyl}-amine (Compound 16-2) as a TFA salt. MH$^+$=316.8.

The enantiomers of dimethyl-{2-[3-(1-thiazol-4-yl-ethyl)-benzo[b]thiophen-2-yl]-ethyl}-amine, dimethyl-{2-[3-((R)-1-thiazol-4-yl-ethyl)-benzo[b]thiophen-2-yl]-ethyl}-amine (Compound 16-3) and dimethyl-{2-[3-((R)-1-thiazol-4-yl-ethyl)-benzo[b]thiophen-2-yl]-ethyl}-amine (Compound 16-4), were separated by chiral chromatography using (column chiralcel OJ-H; eluent: Hexanes/EtOH=7/3 and 0.1% diethylamine.

In a similar procedure {2-[3-(4-methoxy-pyridin-3-yl)-benzo[b]thiophen-2-yl]-ethyl}-dimethyl-amine (Compound 16-5) was prepared. 3-{1-[2-(2-dimethylamino-ethyl)-benzo[b]thiophen-3-yl]-ethyl}-pyridin-4-ol (Compound 16-6) was generated as a side product in the last step.

The compounds of Table 6 were prepared according to the procedures described in Example 16:

TABLE 6

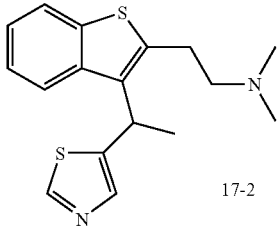

| No | R$_1$ | R$_2$ | MW | MH$^+$ | t$_R$ (method) |
|---|---|---|---|---|---|
| 16-2 | thiazol-4-yl | Me | 316.5 | 316.8 | 4.44 (2) |
| 16-3 | thiazol-4-yl | (R)Me | 316.5 | 317.0 | 4.52 (2) |
| 16-4 | thiazol-4-yl | (S)Me | 316.5 | 317.0 | 4.46 (2) |
| 16-5 | 4-methoxy-pyridin-3-yl | Me | 340.5 | 341.0 | 2.95 (2) |
| 16-6 | 4-methoxy-pyridin-3-yl | Me | 326.5 | 327.1 | 9.26 (4) |

Example 17

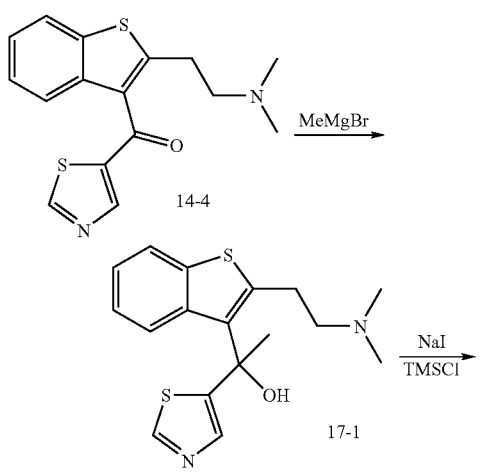

To a cooled (−78° C.) solution of [2-(2-dimethylamino-ethyl)-benzo[b]thiophen-3-yl]-thiazol-5-yl-methanone (35 mg, 0.11 mmol) in anhydrous THF (2 mL), MeMgBr (0.4 mL, 0.55 mmol, 3M in ether) was added. The mixture was stirred for 1 hour at −78° C., an additional batch of MeMgBr (10 mL, 14 mmol) was added and the temperature was allowed to slowly increase to room temperature. The reaction was quenched with diluted NH$_4$OH until pH ~8, extracted with EtOAc and concentrated. The residue was purified by mass triggered preparative HPLC to give 3 mg of 1-[2-(2-dimethylamino-ethyl)-benzo[b]thiophen-3-yl]-1-thiazol-5-yl-ethanol (Compound 17-1) as a TFA salt.

A mixture of NaI (24 mg, 0.16 mmol)) and TMSCl (20 uL, 0.16 mmol) in acetonitrile (0.5 mL) was stirred for 15 min at room temperature. A solution of 1-[2-(2-dimethylamino-ethyl)-benzo[b]thiophen-3-yl]-1-thiazol-5-yl-ethanol (Compound 17-1) (3 mg, 0.01 mmol) in dichloromethane (1.3 mL) was added and the reaction was stirred in a sealed vial at 100° C. for 3 hrs. The mixture was quenched with 1M Na$_2$S$_2$O$_3$ until colorless and diluted NH$_4$OH was added until pH ~8. The product was extracted with EtOAc and the combined organic layers were washed with diluted NH$_4$OH, concentrated and subjected to mass triggered preparative HPLC purification to afford dimethyl-{2-[3-(1-thiazol-5-yl-ethyl)-benzo[b]thiophen-2-yl]-ethyl}-amine (Compound 17-2). MH$^+$=317.0, t$_R$=4.24 min, (Method 2).

The enantiomers, dimethyl-{2-[3-((R)-1-thiazol-5-yl-ethyl)-benzo[b]thiophen-2-yl]-ethyl}-amine (Compound 17-3) (MH$^+$=317.0, t$_R$=4.40, Method 2) and dimethyl-{2-[3-((S)-1-thiazol-5-yl-ethyl)-benzo[b]thiophen-2-yl]-ethyl}-amine (Compound 17-4) (MH$^+$=317.0, t$_R$=4.39, Method 2), were separated using a chiral HPLC OJ-H column, Eluent: Hexanes:EtOH=85:15 with 0.1% DEA Example 18

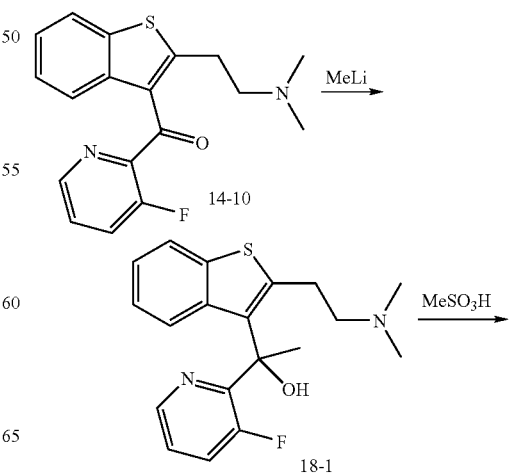

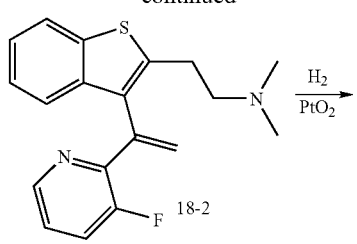

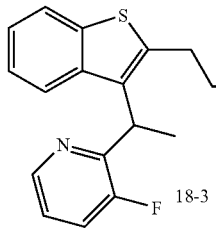

[2-(2-Dimethylamino-ethyl)-benzo[b]thiophen-3-yl]-(3-fluoro-pyridin-2-yl)-methanone (37 mg, 0.11 mmol) was dissolved in tetrahydrofuran (1 mL) and was cooled at −78° C. and methyllithium in hexane (0.070 mL, 0.11 mmol, 1.6 M in hexanes) was added dropwise. The reaction was stirred at −78° C. for 90 minutes and monitored by LC/MS. Additional methyllithium (0.14 mL, 0.22 mmol, 1.6 M in hexane) was added and stirring was continued for 60 minutes. The reaction was quenched with water and ammonium hydroxide and extracted with EtOAc. The combined organic layers were concentrated in vacuo and used for the next step without further purification.

1-[2-(2-Dimethylamino-ethyl)-benzo[b]thiophen-3-yl]-1-(3-fluoro-pyridin-2-yl)-ethanol (Compound 18-1) (39 mg, 0.11 mmol) was dissolved in methylene chloride (6 mL) and was stirred at room temperature. Methanesulfonic acid (70 uL, 1 mmol) was added dropwise and the reaction was allowed to stir for 2 hours. An additional aliquot of methanesulfonic acid (77 uL, 1.1 mmol) was added and stirring was continued for 2 more hours. The reaction was neutralized with aq NH$_4$OH and was extracted with methylene chloride. The organic layer was concentrated and the crude material was used for the next step without further purification.

To a solution of (2-{3-[1-(3-fluoro-pyridin-2-yl)-vinyl]-benzo[b]thiophen-2-yl}-ethyl)-dimethyl-amine (Compound 18-2) (26 mg, 0.080 mmol) in ethanol (1 mL), platinum dioxide (9 mg, 0.04 mol) was added. The reaction was shaken at 30 psi for 4 hours under H$_2$ atmosphere and monitored by LC/MS. The reaction was filtered and washed with EtOH and subsequently purified by mass triggered preparative HPLC to afford (2-{3-[1-(3-fluoro-pyridin-2-yl)-ethyl]-benzo[b]thiophen-2-yl}-ethyl)-dimethyl-amine (Compound 18-3). MH$^+$=329. t$_R$=4.7 min (Method 2).

The enantiomers, (2-{3-[(R)-1-(3-fluoro-pyridin-2-yl)-ethyl]-benzo[b]thiophen-2-yl}-ethyl)-dimethyl-amine (Compound 18-4) (MH$^+$=329.0, t$_R$=40.366, Method 2) and (2-{3-[(S)-1-(3-fluoro-pyridin-2-yl)-ethyl]-benzo[b]thiophen-2-yl}-ethyl)-dimethyl-amine (Compound 18-5) (MH$^+$=329.0, t$_R$=4.251, Method 2), were separated by SFC CHIRALPAK AD-H column, hexanes/iPrOH/diethylamine=99/1/0.1 @50 ML/MIN. 100 bar and 35 degrees.

Example 19

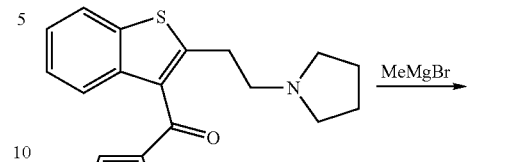

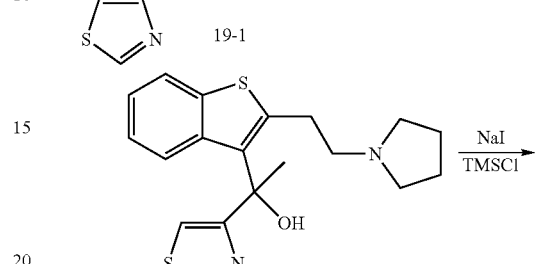

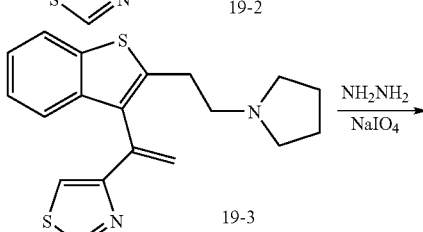

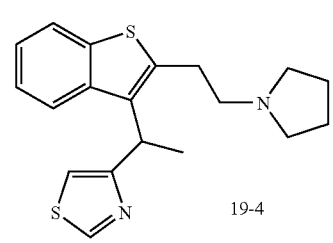

To a cooled solution (−78° C.) of [2-(2-pyrrolidin-1-yl-ethyl)-benzo[b]thiophen-3-yl]-thiazol-4-yl-methanone (Compound 19-1) (1.71 g, 5 mmol) in anhydrous THF (90 mL), MeMgBr (5 mL, 15 mmol, 3M in ether) was added and the mixture was stirred overnight and allowed to reach room temperature. The reaction was quenched with water and ammonia and extracted with EtOAc. The organic layers were dried over Na$_2$SO$_4$, filtered and concentrated to generate 1.42 g of 1-[2-(2-pyrrolidin-1-yl-ethyl)-benzo[b]thiophen-3-yl]-1-thiazol-4-yl-ethanol (Compound 19-2) in 79% yield.

NaI was taken up in acetonitrile (30 mL) under N$_2$ and trimethylsilyl chloride was slowly added (2.97 mL, 24 mmol). The mixture was stirred for 15 min after which a solution of 1-[2-(2-pyrrolidin-1-yl-ethyl)-benzo[b]thiophen-3-yl]-1-thiazol-4-yl-ethanol (1.4 g, 3.91 mmol) in acetonitrile (30 mL) and dichloromethane (10 mL) was added. The reaction was heated in a closed vessel to 100° C. for 3 hrs. After cooling to room temperature 1M sodium thiosulfate was added followed by NH$_4$OH until pH ~9. After extraction with EtOAc, drying (MgSO$_4$), filtering, concentration in vacuo and subsequently purification by mass triggered preparative HPLC, 4-{1-[2-(2-pyrrolidin-1-yl-ethyl)-benzo[b]thiophen-3-yl]-vinyl}-thiazole (Compound 19-3) was isolated MH$^+$=341.

To a mixture of EtOH (7 mL) and water (2 mL), sodium periodate (1.4 g, 6.62 mmol), 4-{1-[2-(2-pyrrolidin-1-yl-ethyl)-benzo[b]thiophen-3-yl]-vinyl}-thiazole (225 mg, 0.66 mmol) and hydrazine (880 uL, 27 mmol) were added. The reaction was refluxed for 90 min, cooled down to room temperature and additional hydrazine (880 uL, 27 mmol) and sodium periodate (1.4 g, 6.6 mmol) were added. The reaction was refluxed for an additional hour, cooled down and additional aliquots of hydrazine (880 uL, 27 mmol) and sodium periodate (1.4 g, 6.6 mmol) were added. After refluxing overnight, water and ammonia were added (pH ~9), which was followed by extraction with EtOAc, drying (MgSO$_4$), filtration, and concentration in vacuo. Mass triggered preparative HPLC afforded 4-{1-[2-(2-pyrrolidin-1-yl-ethyl)-benzo[b]thiophen-3-yl]-ethyl}-thiazole (Compound 19-4). MH$^+$=343.

The use of chiral preparative HPLC (chiralcel OJ-H; eluent hexanes/EtOH/diethylamine=95/5/0.1) afforded 4-{(R)-1-[2-(2-pyrrolidin-1-yl-ethyl)-benzo[b]thiophen-3-yl]-ethyl}-thiazole (Compound 19-5) (MH$^+$=343, $t_R$=40.58, Method 2) and 4-{(S)-1-[2-(2-pyrrolidin-1-yl-ethyl)-benzo[b]thiophen-3-yl]-ethyl}-thiazole (Compound 19-6) (MH$^+$=343, $t_R$=40.55, Method 2).

Example 20

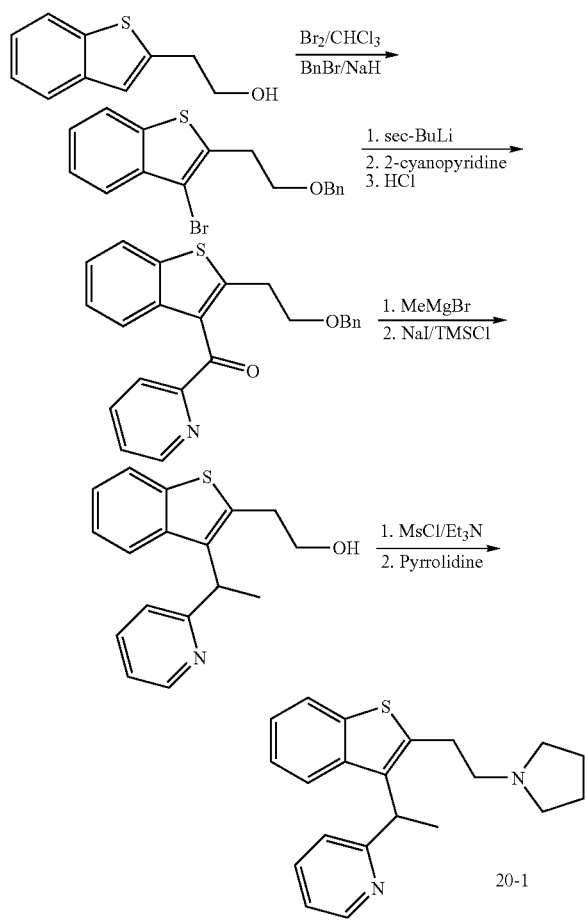

To a cooled solution (0° C.) of 2-benzo[b]thiophen-2-yl-ethanol (5 g, 28.1 mmol) in CHCl$_3$ (30 mL), bromine (1.73 mL, 33.7 mmol) was added dropwise. The reaction was stirred overnight while gradually being warmed to room temperature. Saturated NaHCO$_3$ was added and the organic layer was separated. The aqueous layer was subsequently extracted with dichloromethane and the combined organic layers were dried (Na$_2$SO$_4$) and concentrated in vacuo to afford 2-(3-bromo-benzo[b]thiophen-2-yl)-ethanol in quantitative yield.

To a cooled solution (0° C.) of 2-(3-bromo-benzo[b]thiophen-2-yl)-ethanol (7.7 g, 29.9 mmol) in DMF (40 mL), NaH (1.44 g, 59.8 mmol, 95%) was added and the mixture was stirred for 20 min at 0° C. Subsequently benzylbromide (5.3 mL, 45 mmol) was added and the mixture was stirred overnight while the temperature gradually reached room temperature. After quenching with MeOH, the mixture was concentrated in vacuo, dissolved in EtOAc, washed with sat NaHCO$_3$, brine, dried (Na$_2$SO$_4$) and concentrated in vacuo. Purification by silica gel column chromatography (eluent: EtOAc/Hexanes=1/1) afforded 9.1 g of 2-(2-benzyloxy-ethyl)-3-bromo-benzo[b]thiophene (87% yield).

To a cooled solution (−78° C.) of 2-(2-benzyloxy-ethyl)-3-bromo-benzo[b]thiophene (9.6 g, 27.6 mmol) in anhydrous THF (200 mL), TMEDA (4.14 mL, 27.6 mmol) was added and the mixture was stirred for 5 min. After dropwise addition of sec-BuLi (23.3 mL, 30.3 mmol), while keeping the temperature below −60° C., the mixture was stirred for an additional 30 min at −78° C. A solution of 2-cyanopyridine (3.16 g, 30.34 mmol) in toluene (30 mL) was added and after stirring for 30 min at −78° C. the reaction was quenched by dropwise addition of 6N HCl (66 mL) in MeOH (134 mL), while keeping the temperature below −60° C. After stirring overnight while allowing the mixture to reach room temperature, the mixture was concentrated in vacuo. The residue was dissolved in dichloromethane (100 mL) and NH$_4$OH (100 mL) was added. The organic layer was separated and the aqueous layer was further extracted with dichloromethane. The combined organic layers were dried (Na$_2$SO$_4$), concentrated and subjected to silica gel column chromatography (eluent: EtOAc/Hex=1/4 up to EtOAc/Hex=1/1) to afford 4.2 g of [2-(2-benzyloxy-ethyl)-benzo[b]thiophen-3-yl]-pyridin-2-yl-methanone (41% yield).

To a solution of [2-(2-benzyloxy-ethyl)-benzo[b]thiophen-3-yl]-pyridin-2-yl-methanone (4.2 g, 11.3 mmol) in toluene (30 mL) at room temperature, methylmagnesium bromide (4.5 mL, 3 M in ether) was added and the mixture was stirred for 30 min at room temperature. Water was added to quench the reaction, followed by extraction with EtOAc. The combined organic layers were dried (Na$_2$SO$_4$) and concentrated in vacuo to generate 4.2 g of 1-[2-(2-benzyloxy-ethyl)-benzo[b]thiophen-3-yl]-1-pyridin-2-yl-ethanol, which was used for the next step without further purification.

To a solution of NaI (2.29 g, 15.4 mmol) in acetonitrile (45 mL) at room temperature, trimethylsilyl chloride (1.96 mL, 15.4 mmol) was added and the mixture was stirred for 5 min. 1-[2-(2-benzyloxy-ethyl)-benzo[b]thiophen-3-yl]-1-pyridin-2-yl-ethanol (2 g, 5.14 mmol) was added and the mixture was refluxed for 4 hours. An additional aliquot of trimethylsilyl chloride (2.6 mL, 20.5 mmol) and NaI (3.06 g, 20.6 mmol) was added and refluxing was continued for another 6 hours. Sat. NaHCO$_3$ and EtOAc were added and the organic layer was separated. After extraction of the aqueous layers with EtOAc, the combined organic layers were dried (Na$_2$SO$_4$) and concentrated. Silica gel column chromatography (eluent: hexanes up to EtOAc/hexanes=1/1) afforded 2-[3-(1-pyridin-2-yl-ethyl)-benzo[b]thiophen-2-yl]-ethanol in 20% yield.

To a solution of 2-[3-(1-pyridin-2-yl-ethyl)-benzo[b]thiophen-2-yl]-ethanol (282 mg, 1.0 mmol) in dichloroethane (5 mL), triethylamine (208 uL, 1.5 mmol) and methanesulfonyl chloride (85 uL, 1,1 mmol) were added at 0° C. The mixture was allowed to warm to room temperature overnight, concentrated in vacuo and used in the next step without further purification.

A mixture of methanesulfonic acid, 2-[3-(1-pyridin-2-yl-ethyl)-benzo[b]thiophen-2-yl]-ethyl ester (60 mg, 0.166 mmol) and pyrrolidine (56 uL, 0.66 mmol) in isopropanol (1 mL) was heated at 85° C. overnight. Once cooled to room temperature, the mixture was subjected to mass triggered preparative HPLC to generate 2-{1-[2-(2-pyrrolidin-1-yl-ethyl)-benzo[b]thiophen-3-yl]-ethyl}-pyridine (Compound 20-1) as a TFA salt. (MH$^+$=337, $t_R$=3.43, Method 2).

The enantiomers, 2-{(S)-1-[2-(2-pyrrolidin-1-yl-ethyl)-benzo[b]thiophen-3-yl]-ethyl}-pyridine (Compound 20-2) (MH$^+$=337, $t_R$=3.18, Method 2) and 2-{(R)-1-[2-(2-pyrrolidin-1-yl-ethyl)-benzo[b]thiophen-3-yl]-ethyl}-pyridine (Compound 20-3) (MH$^+$=337, $t_R$=3.13, Method 2), were separated using chiral HPLC (column: Chiralcel OJ-H, eluent: Hexanes/EtOH=95/5 and 0.1% DIEA).

The enantiomers, 2-{(R)-1-[2-(2-azetidin-1-yl-ethyl)-benzo[b]thiophen-3-yl]-ethyl}-pyridine (Compound 20-8) (MH$^+$=323, $t_R$=3.01, Method 2) and 2-{(S)-1-[2-(2-azetidin-1-yl-ethyl)-benzo[b]thiophen-3-yl]-ethyl}-pyridine (Compound 20-9) (MH$^+$=323, $t_R$=3.07, Method 2), were separated using chiral HPLC (column: ChiralPak AD-H, eluent: Hexanes/EtOH=90/10 and 0.1% DIEA)

The compounds of Table 7 were prepared according to the procedures described in Example 20:

TABLE 7

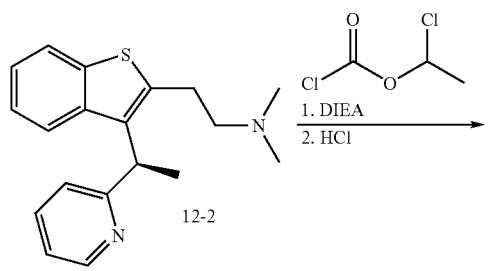

| No | R$_1$ | R$_2$ | MW | MH$^+$ | $t_R$ (method 2) |
|---|---|---|---|---|---|
| 20-1 | pyrrolidin-1-yl | Me | 336.5 | 337 | 3.306 |
| 20-2 | pyrrolidin-1-yl | (S)Me | 336.5 | 337 | 3.18 |
| 20-3 | pyrrolidin-1-yl | (R)Me | 336.5 | 337 | 3.13 |
| 20-4 | 2,5-dihydro-pyrrol-1-yl | Me | 334.5 | 335 | 3.165 |
| 20-5 | morpholin-4-yl | Me | 353 | 353 | 3.196 |
| 20-6 | 3-hydroxy-pyrrolidin-1-yl | Me | 352.5 | 353 | 3.165 |
| 20-7 | azetidin-1-yl | Me | 322.5 | 323 | 3.175 |
| 20-8 | azetidin-1-yl | (R)Me | 322.5 | 323 | 3.01 |
| 20-9 | azetidin-1-yl | (S)Me | 322.5 | 323 | 3.07 |

Example 21

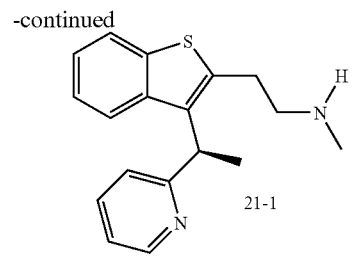

To a solution of dimethyl-{2-[3-((R)-1-pyridin-2-yl-ethyl)-benzo[b]thiophen-2-yl]-ethyl}-amine (Compound 12-2) (0.305 mg, 0.98 mmol) in dichloromethane (3 mL), DIEA (1 mL, 5.8 mmol) and 1-chloroethyl chloroformate (0.32 mL, 2.95 mmol) were added. The mixture was stirred for 1 hour at 40° C. The solvent was removed in vacuo and 1N HCl was added to the residue. The mixture was stirred at 40° C. for an additional hour and cooled to ambient temperature. After neutralization with NH$_4$OH the product was extracted with dichloromethane. The organic layer was dried (MgSO$_4$), filtered and concentrated in vacuo to give 300 mg of crude product, which was purified by mass triggered HPLC to give methyl-{2-[3-((R)-1-pyridin-2-yl-ethyl)-benzo[b]thiophen-2-yl]-ethyl}-amine (Compound 21-1). (MH$^+$=297, $t_R$=1.675, Method 4)

Example 22

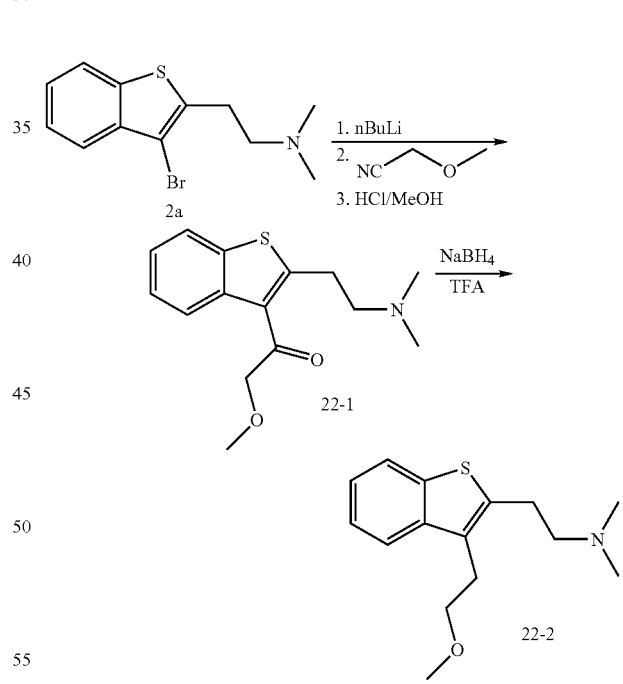

To a cooled (−78° C.) solution of [2-(3-bromo-benzo[b]thiophen-2-yl)-ethyl]-dimethyl-amine (0.1 g, 0.35 mmol) in toluene (4 mL), TMEDA (55 uL, 0.36 mmol) was added followed by n-BuLi (0.26 mL, 0.4 mmol, 1.6M). The mixture was stirred for 40 min at −78° C. Methoxy-acetonitrile (0.1 mL, 1.4 mmol) was added and the mixture was stirred for 48 hrs while the temperature was allowed to increase to ambient temperature. The reaction was quenched with a mixture of 20% HCl (0.6 mL) and MeOH (1.2 mL) and concentrated in vacuo. EtOAc was added followed by NH$_4$OH until pH was approximately 9. The organic layer was separated and the aqueous layer was extracted with EtOAc. The combined organic layers were concentrated and subjected to mass triggered preparative HPLC to generate 1-[2-(2-dimethylamino-ethyl)-benzo[b]thiophen-3-yl]-2-methoxy-ethanone (Compound 22-1).

Sodium borohydride (16 mg, 0.42 mmol) was added to a cooled (0° C.) solution of TFA (0.6 mL). The mixture was stirred for 30 min at room temperature. A solution of 1-[2-(2-dimethylamino-ethyl)-benzo[b]thiophen-3-yl]-2-methoxy-ethanone (10 mg, 0.036 mmol) in dichloromethane ((0.6 mL) was added and the mixture was heated at reflux for 1 hour. An additional batch of sodium borohydride (10 mg) was added and the reaction was stirred overnight at rt. Diluted $NH_4OH$ was added until the pH of the mixture was approximately 9. The product was extracted with dichloromethane, the organic layer was concentrated and purified by mass triggered preparative HPLC to afford {2-[3-(2-methoxy-ethyl)-benzo[b]thiophen-2-yl]-ethyl}-dimethyl-amine (Compound 22-2). ($MH^+$=263.9, $t_R$=4.07, Method 2).

Example 23

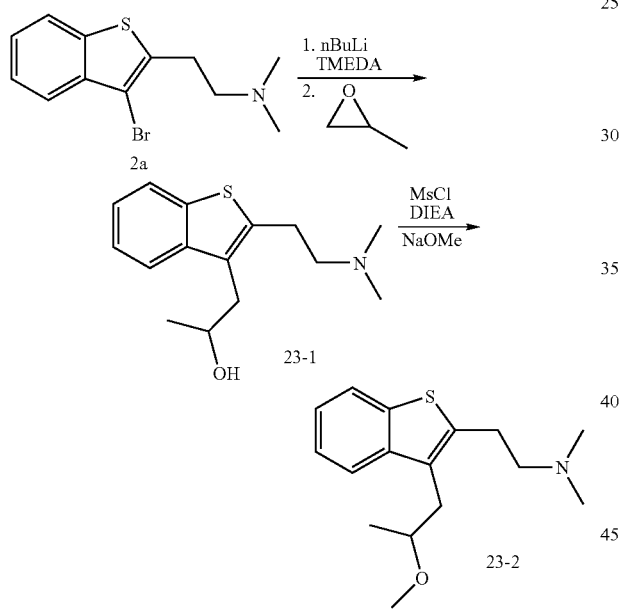

A solution of [2-(3-bromo-benzo[b]thiophen-2-yl)-ethyl]-dimethyl-amine (285 mg, 1 mmol) and TMEDA (181 uL, 1.2 mmol) in toluene (12 mL) was cooled to −78° C. n-BuLi (750 uL, 1.2 mmol, 1.6M in hexanes) was added and the reaction was stirred at −78° C. for 45 min. 2-Methyl-oxirane (280 uL, 4 mmol) was added at −78° C. and the reaction was allowed to slowly reach room temperature, while being stirred overnight. The reaction was quenched with $NH_4Cl$, pH was adjusted with sat. $NaHCO_3$ until pH ~9, followed by an extraction with EtOAc (4x). The combined organic layers were washed with brine, dried ($MgSO_4$) and concentrated. Silica gel column chromatography (eluent: dichloromethane with gradient up to dichloromethane/MeOH=97/3) afforded 46 mg of 1-[2-(2-dimethylamino-ethyl)-benzo[b]thiophen-3-yl]-propan-2-ol (Compound 23-1).

To a cooled (−10° C.) solution of 1-[2-(2-dimethylamino-ethyl)-benzo[b]thiophen-3-yl]-propan-2-ol (25 mg, 0.095 mmol) in dichloromethane (1 mL), DIEA (25 μL, 0.14 mmol) was added followed by mesylchloride (9 μL, 0.1 mmol), the reaction was allowed to stir at room temperature. After 1 hour an additional portion of mesylchloride (10 μL, 0.11 mmol) was added and stirring was continued for another hour. Sodium methoxide (0.15 mL, 0.66 mmol, 25% wt solution in MeOH) was added and the mixture was stirred overnight at room temperature. It was quenched with diluted ammonia until pH ~9 and extracted with dichloromethane. The combined organic layers were dried and subjected to mass triggered preparative HPLC to afford the TFA salt of {2-[3-(2-methoxy-propyl)-benzo[b]thiophen-2-yl]-ethyl}-dimethyl-amine (Compound 23-2). ($MH^+$=278.0, $t_R$=4.18, Method 2)

Example 24

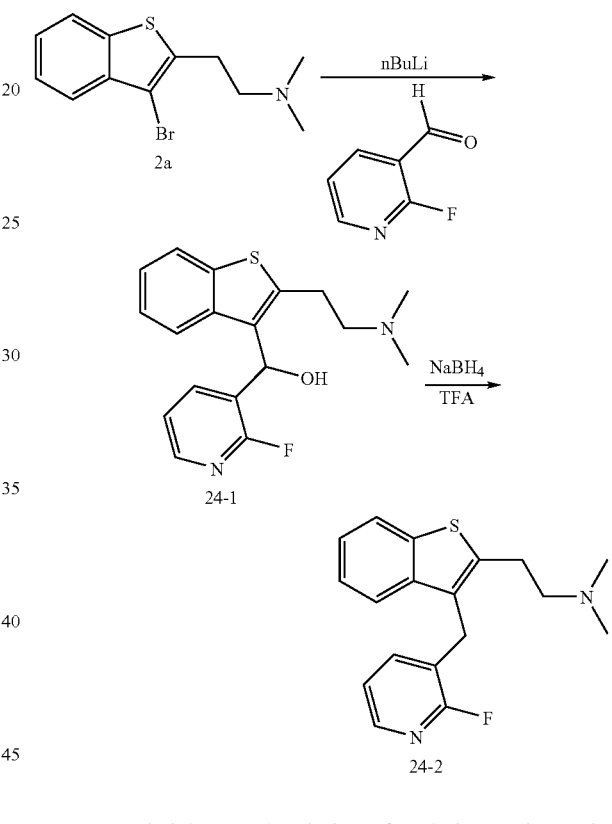

To a cooled (−78° C.) solution of [2-(3-bromo-benzo[b]thiophen-2-yl)-ethyl]-dimethyl-amine (400 mg, 1.4 mmol) in anhydrous toluene (16 mL), TMEDA (240 uL, 2.8 mmol) was added followed by nBuLi (1.0 mL, 1.7 mmol, 1.6M in hexanes). The mixture was stirred for 40 min at −78° C. and 2-fluoro-3-pyridine-carbaldehyde (0.70 g, 5.6 mmol) was added. The mixture was stirred for 12 hrs during which the mixture warmed up to room temperature, quenched with 1M HCl (2 mL) and extracted with EtOAc (3x). The combined organic layers were dried ($Na_2SO_4$), concentrated and purified by silical gel column chromatography (gradient of DCM/MeOH=98/2 up to 90/10) to afford [2-(2-dimethylamino-ethyl)-benzo[b]thiophen-3-yl]-(2-fluoro-pyridin-3-yl)-methanol (Compound 24-1) (0.12 g) in 26% yield. $MH^+$=331.0.

A suspension of $NaBH_4$ (0.11 g, 2.9 mmol) in 7 mL TFA was stirred at room temperature for 15 minutes. A solution of [2-(2-dimethylamino-ethyl)-benzo[b]thiophen-3-yl]-(2-fluoro-pyridin-3-yl)-methanol (0.12 g, 0.36 mmol) in 6 mL TFA was added slowly. The mixture was stirred at room temperature for 48 h. The solvent was evaporated and water and ammonium hydroxide were added at 0° C. until pH=9. The solution was extracted with EtOAc (3×) and washed with water/ammonium hydroxide (30/1 v/v). The combined organic layers were concentrated and 0.12 g of crude material was obtained. Purification by Mass triggered HPLC afforded 32 mg of {2-[3-(2-fluoro-pyridin-3-ylmethyl)-benzo[b]thiophen-2-yl]-ethyl}-dimethyl-amine (Compound 24-2) (MH$^+$=315.0, $t_R$=4.50, Method 2).

Example 25

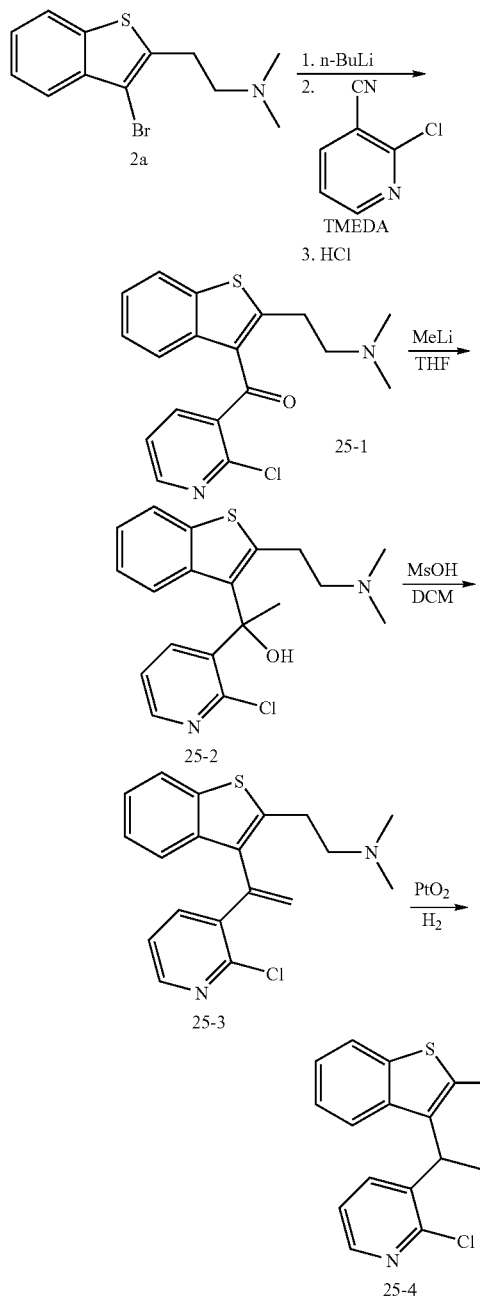

To a solution of [2-(3-bromo-benzo[b]thiophen-2-yl)-ethyl]-dimethyl-amine (1.00 g, 3.52 mol) and N,N,N',N'-tetramethylethylenediamine (0.53 mL, 3.52 mol) in toluene (40 mL) at −78° C. 1.6 M of n-butyllithium in hexane (2.6 mL) was added. The reaction was stirred for 45 minutes at −78° C. A solution of 2-chloro-3-nitrile pyridine (1.46 g, 10.6 mol) in 10 mL THF was added slowly and the reaction was stirred for 45 minutes at −78° C. The reaction was quenched with 1 M of HCl in water (4 mL) and the mixture was warmed up to room temperature. The mixture was concentrated in vacuo and 15 mL ethanol was added followed by a solution of 1 M of HCl in water (4 mL). The mixture was stirred at room temperature for 30 minutes and an additional batch of 38 mL 1 N HCl and 20 mL of EtOH was added in portions. After 2 h the mixture was concentrated in vacuo. Water and ammonium hydroxide were added to the crude mixture until the pH was basic. The solution was extracted with EtOAc (3×30 mL) and washed with water/ammonium hydroxide (30/1 v/v). The combined organic layers were concentrated and 2.14 g of crude material was obtained. Purification by silica gel column chromatography (eluent: 3% MeOH in DCM) afforded 0.57 g of (2-chloro-pyridin-3-yl)-[2-(2-dimethylamino-ethyl)-benzo[b]thiophen-3-yl]-methanone (Compound 25-1) in 47% yield.

Chloro-pyridin-3-yl)-[2-(2-dimethylamino-ethyl)-benzo[b]thiophen-3-yl]-methanone was transformed to (2-{3-[1-(2-chloro-pyridin-3-yl)-ethyl]-benzo[b]thiophen-2-yl}-ethyl)-dimethyl-amine (Compound 25-4) according to the procedure described Example 7, with the following modifications: hydrogenation in the last step was performed under 40 psi for 40 hours under H$_2$ atmosphere, and purification was accomplished by silica gel column chromatography (eluent: DCM/MeOH=9/1). MH$^+$=345.1 ($t_R$=16.32 min, Method 4)

The enantiomers, (2-{3-[(R)-1-(2-chloro-pyridin-3-yl)-ethyl]-benzo[b]thiophen-2-yl}-ethyl)-dimethyl-amine (Compound 25-5) (MH$^+$=345.0, $t_R$=4.74, Method 2) and (2-{3-[(S)-1-(2-chloro-pyridin-3-yl)-ethyl]-benzo[b]thiophen-2-yl}-ethyl)-dimethyl-amine (Compound 25-6) (MH$^+$=345.0, $t_R$=4.72, Method 2) were separated using chiral HPLC (Chiralpak OD-H, eluent: hexanes/EtOH=90/10 w/0.1% DEA, 15 mL/min).

Example 26

HUMAN HISTAMINE H$_1$ RECEPTOR BINDING ASSAY

Compounds of the present invention may be evaluated for binding to the histamine H$_1$ receptor by a standard binding assay. Crude membranes are prepared from CHO cells transfected with human H$_1$ receptor expression construct by resuspending cells in lysis buffer (50 mM Tris-HCl pH 7.4, 5 mM EDTA, 10 mM MgCl$_2$ and disrupting under N$_2$ at a pressure of 900 psi (Parr Cell disruption bomb, cat. 4639) for 30 min on ice followed by differential centrifugation. The resulting crude membrane pellet is resuspended in assay buffer (50 mM Tris HCl pH 7.4, 100 mM NaCl, 2 mM MgCl$_2$). Membrane protein concentration is adjusted to 1 mg/ml and aliquots were stored at −80° C. An aliquot of membranes (10-20 μg of protein) is incubated for 90 min with 1.5 nM [pyridinyl-5-$^3$H] Pyrilamine (~30 Ci/mmol, Amersham TRK608) in the presence of varying concentrations of competing ligand. Non-specific binding is determined in the presence of excess (1 μM) doxepin. Bound and free ligand are separated by rapid vacuum filtration using a Packard 96-well cell harvester onto UniFilter GF/C filter plates (PerkinElmer) that has been pre-treated with 1% polyethyleneimine. The filter plates are then washed with 600 μl phosphate buffered saline containing 0.01% (v/v) Triton-X100. Bound radioligand is determined by scintillation counting using a TopCount-NXT (Packard).

Binding data is analyzed by nonlinear, least-squares curve fitting algorithms using GraphPad Prism (GraphPad Software, Inc. San Diego, Calif.) or ActivityBase (IDBS, Guildford, Surrey, UK). $K_i$ values are calculated from $IC_{50}$ values using the Cheng-Prusoff equation (*Biochem. Pharm.* 22:3099-3108, 1973).

The following compounds of this invention were screened according to the foregoing method and were found to have $K_i$ values of 1 µM or less:

---

3-2, 3-3, 3-4, 3-6
4-2, 4-3, 4-6
5-3
6-1, 6-2, 6-3, 6-4, 6-5, 6-6, 6-7, 6-8, 6-9, 6-10, 6-11
7-3, 7-4, 7-5
8-3
9-1, 9-2
10-3
11-2
12-1, 12-2
13-3, 13-4, 13-5, 13-6, 13-7, 13-8, 13-9, 13-11, 13-12, 13-13, 13-14, 13-15
15-2, 15-3, 15-4, 15-5, 15-6, 15-7, 15-8, 15-9
16-2, 16-3, 16-4
17-2, 17-3, 17-4
18-3, 18-4, 18-5
19-4, 19-5, 19-6
20-1, 20-2, 20-3, 20-6, 20-7, 20-8, 20-9
21-1
24-2
25-4

---

Example 27

EEG STUDIES

Adult, male Wistar rats (Charles River Laboratories, 275 g) are anesthetized with inhaled isoflurane and restrained in a stereotaxic device. Using aseptic technique, a sterile 6-lead telemetry-based electroencephalographic/electromyographic recording unit (Transdoma/lDataSciences Incorporated) is attached to the rat. Pairs of electroencephalographic leads are placed onto the dura in the frontal and occipital cortices. The EMG leads are sutured into nuchal trapezoidal muscles. An additional lead attached to the muscle layer serves as a ground. Leads are affixed to the skull with dental acrylic. The leads and the attached transmitter are enclosed into a subcutaneous pocket between the scapulae. Rats recover for 7-14 days prior to study.

Rats are individually housed in standard cages with filter top covers and ad libitum food and water in an isolated room with a 24-hour light (12 hours)/dark (12 hours) cycle and controlled humidity. Rats are placed on their individual telemetry receivers and assess to the recording room is restricted 24 hours prior to the baseline recording. Baseline recordings began 6 hours after lights off, 24 hours prior to dosing.

Recordings are made using DataSciences telemetric receivers and compiled with DataSciences ART-GOLD 2.3 software at a sampling frequency of 100 Hz. Recordings from one pair of bilateral EEG leads and from the EMG leads are used to divide the vigilance state of rats into Wake and Sleep (NREM and REM). Power spectra of the EEG signal during individual vigilance states are computed from fast-Fourier transforms generated at 512 Hz.

Sedative effects of test compounds are monitored in male Wistar rats after oral administration of test compounds and vehicle control (0.25% methylcellulose). Compounds are administered during the activity portion of the diurnal cycle, 6 hours after lights-off.

It will be appreciated that, although specific embodiments of the invention have been described herein for purposes of illustration, various modifications may be made without departing from the spirit and scope of the invention. Accordingly, the invention is not limited except as by the appended claims.

What is claimed is:

1. A compound having the following structure:

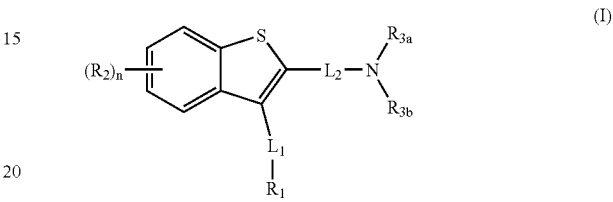

or a stereoisomer, prodrug or pharmaceutically acceptable salt, ester or solvate thereof,
wherein:
$R_1$ is aryl, substituted aryl, heterocycle, substituted heterocycle, alkyl, substituted alkyl, —O-(alkyl) or —O-(substituted alkyl);
$L_1$ and $L_2$ are the same or different and are independently alkanediyl or substituted alkanediyl;
$R_2$ is, at each occurrence, the same or different and independently alkyl, substituted alkyl, alkoxy, substituted alkoxy, cyano, halogen, hydroxyl or —$NR_{4a}R_{4b}$;
n is 0, 1 or 2 and represents the number of $R_2$ groups;
$R_{3a}$ and $R_{3b}$ are the same or different and are independently hydrogen, alkyl or substituted alkyl, or
$R_{3a}$ and $R_{3b}$ together with the nitrogen to which they are attached form a heterocycle or a substituted heterocycle; and
$R_{4a}$ and $R_{4b}$ are the same or different and are independently hydrogen, alkyl or substituted alkyl.

2. A compound according to claim 1, wherein $L_1$ is alkanediyl.

3. A compound according to claim 1, wherein $L_1$ is selected from the group of

—CH$_2$—, —CH(CH$_3$)—, —CH$_2$CH$_2$—,
—CH$_2$CH$_2$CH$_2$—, —CH(CH$_3$)CH$_2$—,
cyclopentanediyl, cyclohexanediyl, cycloheptanediyl,
—CH(OH)—, —C(OH)CH$_3$—, —C(=CH$_2$)—,
—CH=CH—, —CH=CHCH$_2$—,

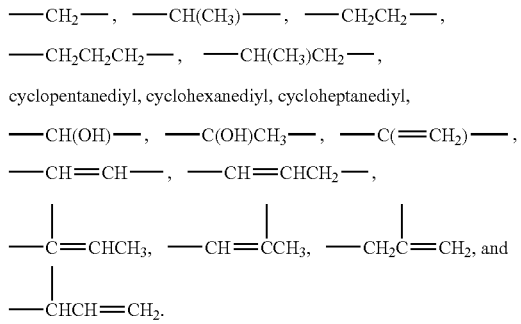

4. A compound according to claim 3, wherein $R_1$ is heterocycle or substituted heterocycle.

5. A compound according to claim 4, wherein $R_1$ is heteroaryl or substituted heteroaryl.

6. A compound according to claim 3, wherein $L_1$ is —CH(CH$_3$)—.

7. A compound according to claim 3, wherein L₁ is —CH₂—.

8. A compound according to claim 3, wherein L₂ is —CH₂CH₂—.

9. A compound according to claim 3, wherein n is zero.

10. A compound according to claim 3, wherein R$_{3a}$ and R$_{3b}$ are both methyl.

11. A compound according to claim 3, wherein R₂ is, at each occurrence, the same or different and independently methyl, methoxy, cyano, halogen, hydroxyl, substituted alkyl or —NR$_{4a}$R$_{4b}$.

12. A compound according to claim 5, wherein R₁ is pyridine or substituted pyridine.

13. A compound according to claim 5, wherein R₁ is thiazole or substituted thiazole.

14. A compound according to claim 1, wherein the compound is selected from the group of:

[2-(2-Dimethylamino-ethyl)-benzo[b]thiophen-3-yl]-(4-fluoro-phenyl)-methanone;
{2-[3-(4-Fluoro-benzyl)-benzo[b]thiophen-2-yl]-ethyl}-dimethyl-amine;
1-[2-(2-Dimethylamino-ethyl)-benzo[b]thiophen-3-yl]-1-(4-fluoro-phenyl)-ethanol;
(2-{3-[1-(4-Fluoro-phenyl)-ethyl]-benzo[b]thiophen-2-yl}-ethyl)-dimethyl-amine;
[2-(2-Dimethylamino-ethyl)-benzo[b]thiophen-3-yl]-phenyl-methanone;
Dimethyl-{2-[3-(4-methyl-benzyl)-benzo[b]thiophen-2-yl]-ethyl}-amine;
[2-(2-Dimethylamino-ethyl)-6-methyl-benzo[b]thiophen-3-yl]-pyridin-2-yl-methanone;
Dimethyl-{2-[6-methyl-3-(1-pyridin-2-yl-ethyl)-benzo[b]thiophen-2-yl]-ethyl}-amine;
Dimethyl-{2-[6-methyl-3-((R)-1-pyridin-2-yl-ethyl)-benzo[b]thiophen-2-yl]-ethyl}-amine;
Dimethyl-{2-[6-methyl-3-((S)-1-pyridin-2-yl-ethyl)-benzo[b]thiophen-2-yl]-ethyl}-amine;
1-[2-(2-Dimethylamino-ethyl)-6-methyl-benzo[b]thiophen-3-yl]-1-pyridin-2-yl-ethanol;
Dimethyl-{2-[6-methyl-3-(1-pyridin-2-yl-vinyl)-benzo[b]thiophen-2-yl]-ethyl}-amine;
[2-(2-Dimethylamino-ethyl)-benzo[b]thiophen-3-yl]-pyridin-2-yl-methanone;
Dimethyl-(2-{3-[1-(4-methyl-pyridin-2-yl)-vinyl]-benzo[b]thiophen-2-yl}-ethyl)-amine;
Dimethyl-(2-{3-[1-(4-methyl-pyridin-2-yl)-ethyl]-benzo[b]thiophen-2-yl}-ethyl)-amine;
1-[2-(2-Dimethylamino-ethyl)-benzo[b]thiophen-3-yl]-1-pyridin-2-yl-ethanol;
Dimethyl-{2-[3-(1-pyridin-2-yl-vinyl)-benzo[b]thiophen-2-yl]-ethyl}-amine;
Dimethyl-{2-[3-(1-pyridin-2-yl-ethyl)-benzo[b]thiophen-2-yl]-ethyl}-amine;
Dimethyl-{2-[3-(1-pyridin-3-yl-vinyl)-benzo[b]thiophen-2-yl]-ethyl}-amine;
Dimethyl-{2-[3-(1-pyridin-4-yl-vinyl)-benzo[b]thiophen-2-yl]-ethyl}-amine;
Dimethyl-{2-[3-(1-pyridin-3-yl-ethyl)-benzo[b]thiophen-2-yl]-ethyl}-amine;
Dimethyl-{2-[3-(1-pyridin-4-yl-ethyl)-benzo[b]thiophen-2-yl]-ethyl}-amine;
Dimethyl-{2-[3-((R)-1-pyridin-3-yl-ethyl)-benzo[b]thiophen-2-yl]-ethyl}-amine;
Dimethyl-{2-[3-((S)-1-pyridin-3-yl-ethyl)-benzo[b]thiophen-2-yl]-ethyl}-amine;
Dimethyl-(2-{3-[1-(3-methoxy-pyridin-2-yl)-ethyl]-benzo[b]thiophen-2-yl}-ethyl)-amine;
Dimethyl-(2-{3-[(R)-1-(3-methyl-pyridin-2-yl)-ethyl]-benzo[b]thiophen-2-yl}-ethyl)-amine;
Dimethyl-(2-{3-[(S)-1-(3-methyl-pyridin-2-yl)-ethyl]-benzo[b]thiophen-2-yl}-ethyl)-amine;
1-[2-(2-Dimethylamino-ethyl)-benzo[b]thiophen-3-yl]-1-(5-fluoro-pyridin-2-yl)-ethanol;
(2-{3-[1-(5-Fluoro-pyridin-2-yl)-vinyl]-benzo[b]thiophen-2-yl}-ethyl)-dimethyl-amine;
(2-{3-[1-(5-Fluoro-pyridin-2-yl)-ethyl]-benzo[b]thiophen-2-yl}-ethyl)-dimethyl-amine;
(2-{3-[(R)-1-(5-Fluoro-pyridin-2-yl)-ethyl]-benzo[b]thiophen-2-yl}-ethyl)-dimethyl-amine;
(2-{3-[(S)-1-(5-Fluoro-pyridin-2-yl)-ethyl]-benzo[b]thiophen-2-yl}-ethyl)-dimethyl-amine;
1-[2-(2-Dimethylamino-ethyl)-benzo[b]thiophen-3-yl]-1-thiazol-2-yl-ethanol;
Dimethyl-{2-[3-(1-thiazol-2-yl-vinyl)-benzo[b]thiophen-2-yl]-ethyl}-amine;
Dimethyl-{2-[3-(1-thiazol-2-yl-ethyl)-benzo[b]thiophen-2-yl]-ethyl}-amine;
Methyl-{2-[3-(1-pyridin-2-yl-ethyl)-benzo[b]thiophen-2-yl]-ethyl}-amine;
Methyl-propyl-{2-[3-(1-pyridin-2-yl-ethyl)-benzo[b]thiophen-2-yl]-ethyl}-amine;
1-[2-(2-Dimethylamino-ethyl)-benzo[b]thiophen-3-yl]-1-(6-methyl-pyridin-3-yl)-ethanol;
Dimethyl-(2-{3-[1-(6-methyl-pyridin-3-yl)-vinyl]-benzo[b]thiophen-2-yl}-ethyl)-amine;
Dimethyl-(2-{3-[1-(6-methyl-pyridin-3-yl)-ethyl]-benzo[b]thiophen-2-yl}-ethyl)-amine;
1-[2-(2-Dimethylamino-ethyl)-benzo[b]thiophen-3-yl]-1-pyrazin-2-yl-ethanol;
Dimethyl-{2-[3-(1-pyrazin-2-yl-ethyl)-benzo[b]thiophen-2-yl]-ethyl}-amine;
Dimethyl-{2-[3-((R)-1-pyrazin-2-yl-ethyl)-benzo[b]thiophen-2-yl]-ethyl}-amine;
Dimethyl-{2-[3-((S)-1-pyrazin-2-yl-ethyl)-benzo[b]thiophen-2-yl]-ethyl}-amine;
Dimethyl-{2-[3-((S)-1-pyridin-2-yl-ethyl)-benzo[b]thiophen-2-yl]-ethyl}-amine;
Dimethyl-{2-[3-((R)-1-pyridin-2-yl-ethyl)-benzo[b]thiophen-2-yl]-ethyl}-amine;
[2-(2-Dimethylamino-ethyl)-benzo[b]thiophen-3-yl]-pyridin-2-yl-methanol;
[2-(2-Dimethylamino-ethyl)-benzo[b]thiophen-3-yl]-pyrimidin-5-yl-methanol;
Dimethyl-[2-(3-pyridin-2-ylmethyl-benzo[b]thiophen-2-yl)-ethyl]-amine;
Dimethyl-[2-(3-pyrimidin-5-ylmethyl-benzo[b]thiophen-2-yl)-ethyl]-amine;
Dimethyl-[2-(3-thiazol-2-ylmethyl-benzo[b]thiophen-2-yl)-ethyl]-amine;
Dimethyl-[2-(3-thiazol-4-ylmethyl-benzo[b]thiophen-2-yl)-ethyl]-amine;
{2-[3-(3-Methoxy-pyridin-2-ylmethyl)-benzo[b]thiophen-2-yl]-ethyl}-dimethyl-amine;
6-[2-(2-Dimethylamino-ethyl)-benzo[b]thiophen-3-ylmethyl]-pyridin-2-ol;
Dimethyl-[2-(3-pyrazin-2-ylmethyl-benzo[b]thiophen-2-yl)-ethyl]-amine;
[2-(3-Furan-2-ylmethyl-benzo[b]thiophen-2-yl)-ethyl]-dimethyl-amine;
Dimethyl-{2-[3-(3-methyl-3H-imidazol-4-ylmethyl)-benzo[b]thiophen-2-yl]-ethyl}-amine;
Dimethyl-[2-(3-[1,2,3]thiadiazol-5-ylmethyl-benzo[b]thiophen-2-yl)-ethyl]-amine;

{2-[3-(2,5-Dimethyl-2H-pyrazol-3-ylmethyl)-benzo[b]thiophen-2-yl]-ethyl}-dimethyl-amine;
{2-[3-(4-Chloro-1-methyl-1H-pyrazol-3-ylmethyl)-benzo[b]thiophen-2-yl]-ethyl}-dimethyl-amine;
Dimethyl-{2-[3-(1-methyl-1H-imidazol-2-ylmethyl)-benzo[b]thiophen-2-yl]-ethyl}-amine;
[2-(2-Dimethylamino-ethyl)-benzo[b]thiophen-3-yl]-thiazol-4-yl-methanol;
[2-(2-Dimethylamino-ethyl)-benzo[b]thiophen-3-yl]-thiazol-4-yl-methanone;
[2-(2-Pyrrolidin-1-yl-ethyl)-benzo[b]thiophen-3-yl]-thiazol-4-yl-methanone;
[2-(2-Dimethylamino-ethyl)-benzo[b]thiophen-3-yl]-thiazol-5-yl-methanone;
2-(2-Dimethylamino-ethyl)-benzo[b]thiophen-3-yl]-2-methoxy-pyridin-3-yl-methanone;
2-(2-Dimethylamino-ethyl)-benzo[b]thiophen-3-yl]-2-fluoro-pyridin-3-yl-methanone;
2-(2-Dimethylamino-ethyl)-benzo[b]thiophen-3-yl]-2-methoxy-pyridin-6-yl-methanone;
2-(2-Dimethylamino-ethyl)-benzo[b]thiophen-3-yl]-2-fluoro-pyridin-6-yl-methanone;
2-(2-Dimethylamino-ethyl)-benzo[b]thiophen-3-yl]-4-methoxy-pyridin-3-yl-methanone;
2-(2-Dimethylamino-ethyl)-benzo[b]thiophen-3-yl]-3-fluoro-pyridin-2-yl-methanone;
(2-{3-[1-(6-Methoxy-pyridin-2-yl)-vinyl]-benzo[b]thiophen-2-yl}-ethyl)-dimethyl-amine;
(2-{3-[1-(6-Methoxy-pyridin-2-yl)-ethyl]-benzo[b]thiophen-2-yl}-ethyl)-dimethyl-amine;
(2-{3-[1-(6-fluoro-pyridin-2-yl)-vinyl]-benzo[b]thiophen-2-yl}-ethyl)-dimethyl-amine;
Dimethyl-(2-{3-[1-(2-methoxy-pyridin-3-yl)-ethyl]-benzo[b]thiophen-2-yl}-ethyl)-amine;
Dimethyl-(2-{3-[(R)-1-(2-methoxy-pyridin-3-yl)-ethyl]-benzo[b]thiophen-2-yl}-ethyl)-amine;
Dimethyl-(2-{3-[(S)-1-(2-methoxy-pyridin-3-yl)-ethyl]-benzo[b]thiophen-2-yl}-ethyl)-amine;
Dimethyl-(2-{3-[1-(2-fluoro-pyridin-3-yl)-ethyl]-benzo[b]thiophen-2-yl}-ethyl)-amine;
Dimethyl-(2-{3-[(R)-1-(2-fluoro-pyridin-3-yl)-ethyl]-benzo[b]thiophen-2-yl}-ethyl)-amine;
Dimethyl-(2-{3-[(S)-1-(2-fluoro-pyridin-3-yl)-ethyl]-benzo[b]thiophen-2-yl}-ethyl)-amine;
1-[2-(2-Dimethylamino-ethyl)-benzo[b]thiophen-3-yl]-1-thiazol-4-yl-ethanol;
Dimethyl-{2-[3-(1-thiazol-4-yl-ethyl)-benzo[b]thiophen-2-yl]-ethyl}-amine;
Dimethyl-{2-[3-((R)-1-thiazol-4-yl-ethyl)-benzo[b]thiophen-2-yl]-ethyl}-amine;
Dimethyl-{2-[3-((R)-1-thiazol-4-yl-ethyl)-benzo[b]thiophen-2-yl]-ethyl}-amine;
(2-{3-[1-(4-Methoxy-pyridin-3-yl)-ethyl]-benzo[b]thiophen-2-yl}-ethyl)-dimethyl-amine;
(2-{3-[1-(4-Hydroxy-pyridin-3-yl)-ethyl]-benzo[b]thiophen-2-yl}-ethyl)-dimethyl-amine;
1-[2-(2-Dimethylamino-ethyl)-benzo[b]thiophen-3-yl]-1-thiazol-5-yl-ethanol;
Dimethyl-{2-[3-(1-thiazol-5-yl-ethyl)-benzo[b]thiophen-2-yl]-ethyl}-amine;
Dimethyl-{2-[3-((R)-1-thiazol-5-yl-ethyl)-benzo[b]thiophen-2-yl]-ethyl}-amine;
Dimethyl-{2-[3-((S)-1-thiazol-5-yl-ethyl)-benzo[b]thiophen-2-yl]-ethyl}-amine;
1-[2-(2-Dimethylamino-ethyl)-benzo[b]thiophen-3-yl]-1-(3-fluoro-pyridin-2-yl)-ethanol;
(2-{3-[1-(3-Fluoro-pyridin-2-yl)-vinyl]-benzo[b]thiophen-2-yl}-ethyl)-dimethyl-amine;
(2-{3-[1-(3-Fluoro-pyridin-2-yl)-ethyl]-benzo[b]thiophen-2-yl}-ethyl)-dimethyl-amine;
(2-{3-[(R)-1-(3-Fluoro-pyridin-2-yl)-ethyl]-benzo[b]thiophen-2-yl}-ethyl)-dimethyl-amine;
(2-{3-[(S)-1-(3-Fluoro-pyridin-2-yl)-ethyl]-benzo[b]thiophen-2-yl}-ethyl)-dimethyl-amine; [2-(2-Pyrrolidin-1-yl-ethyl)-benzo[b]thiophen-3-yl]-thiazol-4-yl-methanone;
1-[2-(2-Pyrrolidin-1-yl-ethyl)-benzo[b]thiophen-3-yl]-1-thiazol-4-yl-ethanol;
4-{1-[2-(2-Pyrrolidin-1-yl-ethyl)-benzo[b]thiophen-3-yl]-vinyl}-thiazole;
4-{1-[2-(2-Pyrrolidin-1-yl-ethyl)-benzo[b]thiophen-3-yl]-ethyl}-thiazole;
4-{(R)-1-[2-(2-Pyrrolidin-1-yl-ethyl)-benzo[b]thiophen-3-yl]-ethyl}-thiazole;
4-{(S)-1-[2-(2-Pyrrolidin-1-yl-ethyl)-benzo[b]thiophen-3-yl]-ethyl}-thiazole;
2-{1-[2-(2-Pyrrolidin-1-yl-ethyl)-benzo[b]thiophen-3-yl]-ethyl}-pyridine;
2-{(S)-1-[2-(2-Pyrrolidin-1-yl-ethyl)-benzo[b]thiophen-3-yl]-ethyl}-pyridine;
2-{(R)-1-[2-(2-Pyrrolidin-1-yl-ethyl)-benzo[b]thiophen-3-yl]-ethyl}-pyridine;
2-(1-{2-[2-(2,5-Dihydro-pyrrol-1-yl)-ethyl]-benzo[b]thiophen-3-yl}-ethyl)-pyridine;
4-{2-[3-(1-Pyridin-2-yl-ethyl)-benzo[b]thiophen-2-yl]-ethyl}-morpholine;
1-{2-[3-(1-Pyridin-2-yl-ethyl)-benzo[b]thiophen-2-yl]-ethyl}-pyrrolidin-3-ol;
2-{1-[2-(2-Azetidin-1-yl-ethyl)-benzo[b]thiophen-3-yl]-ethyl}-pyridine;
2-{(R)-1-[2-(2-Azetidin-1-yl-ethyl)-benzo[b]thiophen-3-yl]-ethyl}-pyridine;
2-{(S)-1-[2-(2-Azetidin-1-yl-ethyl)-benzo[b]thiophen-3-yl]-ethyl}-pyridine;
Methyl-{2-[3-((R)-1-pyridin-2-yl-ethyl)-benzo[b]thiophen-2-yl]-ethyl}-amine;
1-[2-(2-Dimethylamino-ethyl)-benzo[b]thiophen-3-yl]-2-methoxy-ethanone;
{2-[3-(2-Methoxy-ethyl)-benzo[b]thiophen-2-yl]-ethyl}-dimethyl-amine;
1-[2-(2-Dimethylamino-ethyl)-benzo[b]thiophen-3-yl]-propan-2-ol;
{2-[3-(2-Methoxy-propyl)-benzo[b]thiophen-2-yl]-ethyl}-dimethyl-amine;
[2-(2-Dimethylamino-ethyl)-benzo[b]thiophen-3-yl]-(2-fluoro-pyridin-3-yl)-methanol;
{2-[3-(2-Fluoro-pyridin-3-ylmethyl)-benzo[b]thiophen-2-yl]-ethyl}-dimethyl-amine;
(2-Chloro-pyridin-3-yl)-[2-(2-dimethylamino-ethyl)-benzo[b]thiophen-3-yl]-methanone;
1-(2-Chloro-pyridin-3-yl)-1-[2-(2-dimethylamino-ethyl)-benzo[b]thiophen-3-yl]-ethanol;
(2-{3-[1-(2-Chloro-pyridin-3-yl)-vinyl]-benzo[b]thiophen-2-yl}-ethyl)-dimethyl-amine;
(2-{3-[1-(2-Chloro-pyridin-3-yl)-ethyl]-benzo[b]thiophen-2-yl}-ethyl)-dimethyl-amine;
(2-{3-[(R)-1-(2-Chloro-pyridin-3-yl)-ethyl]-benzo[b]thiophen-2-yl}-ethyl)-dimethyl-amine; and
(2-{3-[(S)-1-(2-Chloro-pyridin-3-yl)-ethyl]-benzo[b]thiophen-2-yl}-ethyl)-dimethyl-amine.

15. A compound according to claim 1, wherein the compound is selected from the group of:

Dimethyl-(2-{3-[(R)-1-(3-methyl-pyridin-2-yl)-ethyl]-benzo[b]thiophen-2-yl}-ethyl)-amine;

(R)-(−)-dimethyl-{2-[3-(1-pyridin-2-yl-ethyl)-benzo[b]thiophen-2-yl]-ethyl}-amine;

Dimethyl-(2-{3-[(S)-1-(2-methoxy-pyridin-3-yl)-ethyl]-benzo[b]thiophen-2-yl}-ethyl)-amine;

Dimethyl-(2-{3-[1-(2-fluoro-pyridin-3-yl)-ethyl]-benzo[b]thiophen-2-yl}-ethyl)-amine;

Dimethyl-(2-{3-[(R)-1-(2-fluoro-pyridin-3-yl)-ethyl]-benzo[b]thiophen-2-yl}-ethyl)-amine;

Dimethyl-(2-{3-[(S)-1-(2-fluoro-pyridin-3-yl)-ethyl]-benzo[b]thiophen-2-yl}-ethyl)-amine;

1-[2-(2-Dimethylamino-ethyl)-benzo[b]thiophen-3-yl]-1-thiazol-4-yl-ethanol;

Dimethyl-{2-[3-(1-thiazol-4-yl-ethyl)-benzo[b]thiophen-2-yl]-ethyl}-amine;

Dimethyl-{2-[3-((R)-1-thiazol-4-yl-ethyl)-benzo[b]thiophen-2-yl]-ethyl}-amine;

Dimethyl-{2-[3-((R)-1-thiazol-4-yl-ethyl)-benzo[b]thiophen-2-yl]-ethyl}-amine;

(2-{3-[1-(4-Methoxy-pyridin-3-yl)-ethyl]-benzo[b]thiophen-2-yl}-ethyl)-dimethyl-amine; and (2-{3-[1-(4-Hydroxy-pyridin-3-yl)-ethyl]-benzo[b]thiophen-2-yl}-ethyl)-dimethyl-amine.

16. A pharmaceutical composition comprising a compound of claim 3 in combination with a pharmaceutically acceptable carrier or diluent.

* * * * *